US011433092B2

(12) United States Patent
Baker et al.

(10) Patent No.: US 11,433,092 B2
(45) Date of Patent: Sep. 6, 2022

(54) COMPOSITIONS AND METHODS OF USE FOR WOUND HEALING

(71) Applicant: SYNEDGEN, INC., Claremont, CA (US)

(72) Inventors: Shenda M. Baker, Upland, CA (US); William P. Wiesmann, Washington, DC (US); Stacy M. Townsend, Rancho Cucamonga, CA (US)

(73) Assignee: SYNEDGEN, INC., Claremont, CA (US)

( * ) Notice: Subject to any disclaimer, the term of this patent is extended or adjusted under 35 U.S.C. 154(b) by 0 days.

(21) Appl. No.: 14/776,084

(22) PCT Filed: Mar. 14, 2014

(86) PCT No.: PCT/US2014/028120
§ 371 (c)(1),
(2) Date: Sep. 14, 2015

(87) PCT Pub. No.: WO2014/172040
PCT Pub. Date: Oct. 23, 2014

(65) Prior Publication Data
US 2016/0022730 A1   Jan. 28, 2016

Related U.S. Application Data

(60) Provisional application No. 61/799,751, filed on Mar. 15, 2013.

(51) Int. Cl.
*A61K 31/7072* (2006.01)
*A61K 9/14* (2006.01)
*A61K 9/20* (2006.01)
*A61K 31/726* (2006.01)
*A61K 9/00* (2006.01)

(52) U.S. Cl.
CPC .......... *A61K 31/726* (2013.01); *A61K 9/0014* (2013.01); *A61K 9/0017* (2013.01)

(58) Field of Classification Search
CPC ... A61K 9/0014; A61K 9/0017; A61K 31/726

USPC ........................................................... 514/54
See application file for complete search history.

(56) References Cited

U.S. PATENT DOCUMENTS

| 5,427,778 | A | 6/1995 | Finkenaur et al. |
| 6,958,325 | B2 | 10/2005 | Domb |
| 8,916,542 | B2 * | 12/2014 | Baker ............... A61K 31/722 435/252.1 |
| 9,012,429 | B2 * | 4/2015 | Baker ............... A61K 31/722 514/55 |
| 9,029,351 | B2 * | 5/2015 | Baker ................. A61L 2/232 514/55 |
| 9,439,925 | B2 * | 9/2016 | Baker ............... A61K 31/722 |
| 2010/0130443 | A1 | 5/2010 | Baker et al. |
| 2012/0149659 | A1 | 6/2012 | Haggard et al. |
| 2012/0329753 | A1 | 12/2012 | Baker et al. |

FOREIGN PATENT DOCUMENTS

| JP | S62254763 A | 11/1987 | |
| WO | 2011127144 A1 | 10/2011 | |
| WO | WO 2011/127144 A1 * | 10/2011 | ............... A61K 9/66 |

OTHER PUBLICATIONS

Ghosal et al, Der Pharmacia Sinica, 2011, 2(2), 152-168.*
Dai, et al., "Topical Antimicrobials for Burn Wound Infections", Rencent Pat Antinfect Drug Discov. 5(2): 124-151, Jun. 1, 2010.
International Search Report and the Written Opinion for PCT/US2014/028120 dated Jul. 30, 2014.
Mikusová, V.; Ferková, J.; Zigrayová, D.; Krchnák, D.; Mikus, P. Comparative Study of Polysaccharide-Based Hydrogels: Rheological and Texture Properties and Ibuprofen Release. Gels 2022, 8, 168. https://doi.org/10.3390/gels8030168.

* cited by examiner

*Primary Examiner* — Ganapathy Krishnan
(74) *Attorney, Agent, or Firm* — Goodwin Procter LLP

(57) ABSTRACT

Described herein are a solution, composition, and kit of poly (acetyl, arginyl) glucosamine (PAAG), methods of making the solution, and method of treating wounds with the solution, the method comprising administering to a subject an effective amount of a solution comprising PAAG, wherein the PAAG when administered topically contacts the wound, thereby treating the wound.

18 Claims, 33 Drawing Sheets

Figure 1:
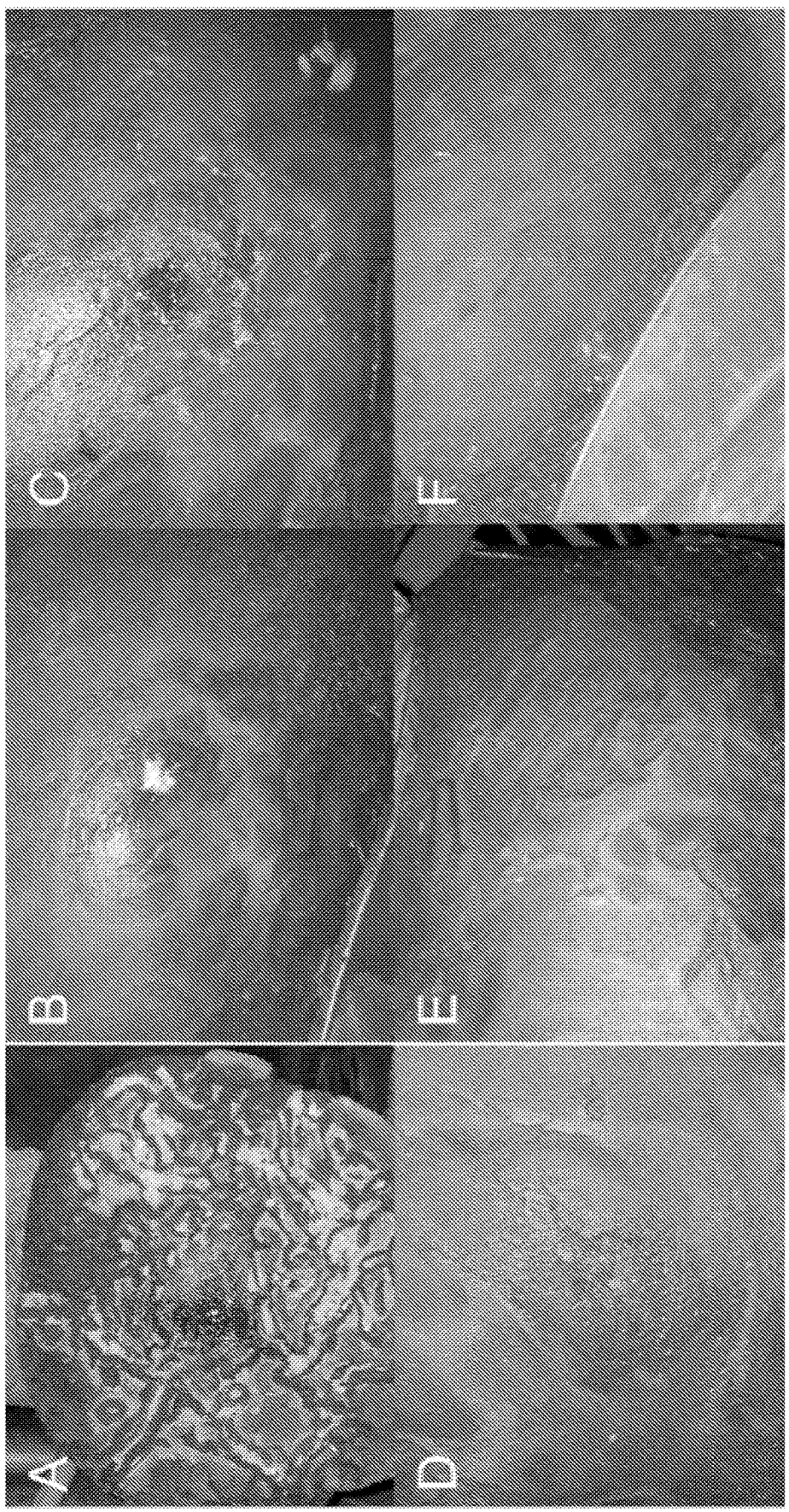

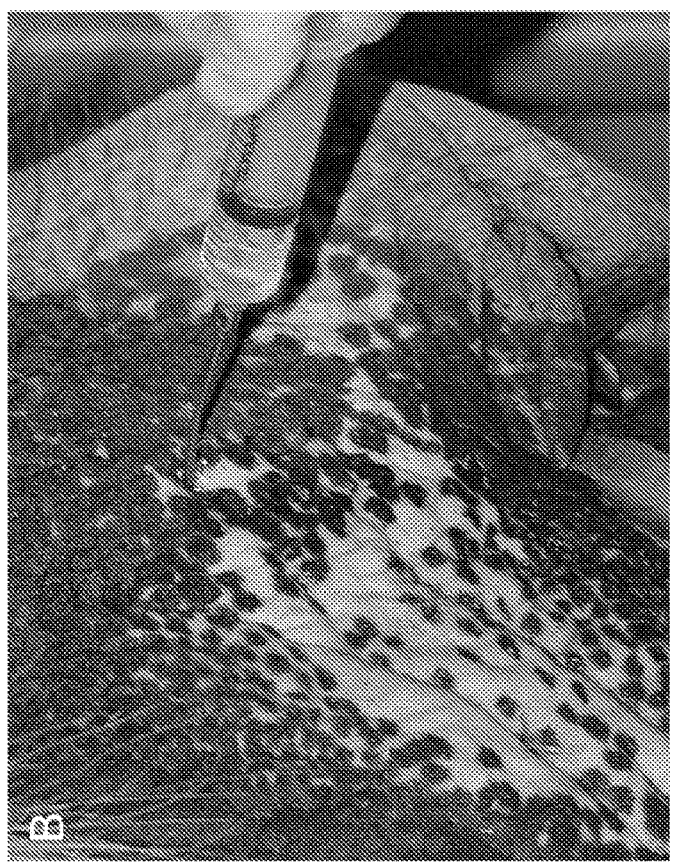
FIG. 3

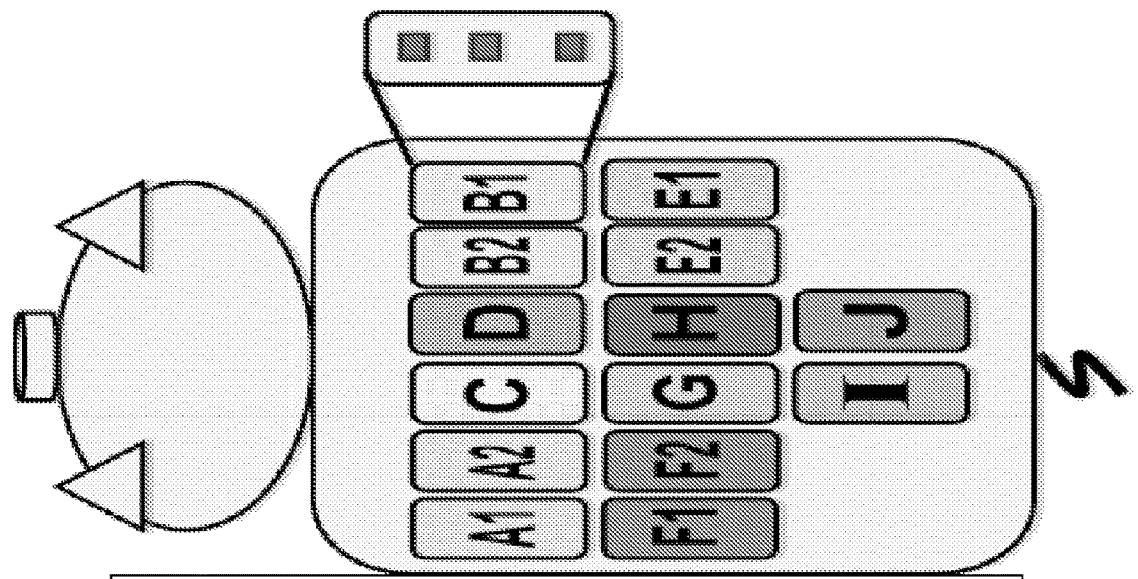

Treatment Groups
A1. Rinse Active A (Irrigation x2 10ml syringes)
(Wound A1-1 without pressure needle)
(Wounds A1 – 2 and A1 – 3 with pressure needle 21G 1.5")
A2. Wipe w/ sterile saline (3ml) gauze twice
(Wound A2 – 4 Wipe w/ sterile saline (3ml) gauze twice)
(Wounds A2 – 5 and A2 – 6 Wipe w/ sterile saline (3ml) gauze twice +
Rinse Active A irrigation x2 10ml syringes with pressure needles 21G 1.5")
B1. Rinse Active A (Irrigation x4 10ml syringes with pressure needles 21G 1.5")
B2. Wipe w/ sterile saline (3ml) gauze twice + Rinse Active A (Irrigation x4 10ml
syringes with 21G 1.5" pressure needles)
C. Gel Vehicle 200μl* recovered 24 hours after Rx application.
D. Untreated wounds recovered 24 hours after Rx application.
E1. Rinse Vehicle for Active A (Irrigation x2 10ml syringes with 21G 1.5" pressure
needles)
E2. Wipe w/ sterile saline (3ml) gauze twice + Rinse Vehicle for Active A (Irrigation x2
10ml syringes with 21G 1.5" pressure needles)
F1. Rinse Vehicle for Active A (Irrigation x4 10ml syringes with 21G 1.5" pressure
needles)
F2. Wipe w/ sterile saline (3ml) gauze twice +
Rinse Vehicle for Active A (Irrigation x4 10ml syringes with 21G 1.5" pressure
needles)
G. Gel Active Dose X 200μl* recovered 24 hours after Rx application.
H. Gel Active Dose Y 200μl* recovered 24 hours after Rx application.
I. Wipe w/ sterile saline (3ml) gauze twice +
Rinse Active A (Irrigation x2 10ml syringes with 21G 1.5" pressure needles) +
Gel Active Dose Y 200μl* recovered 24 hours after Rx application.
J. Untreated wounds recovered on day of Rx application.

FIG. 9

FIG. 21

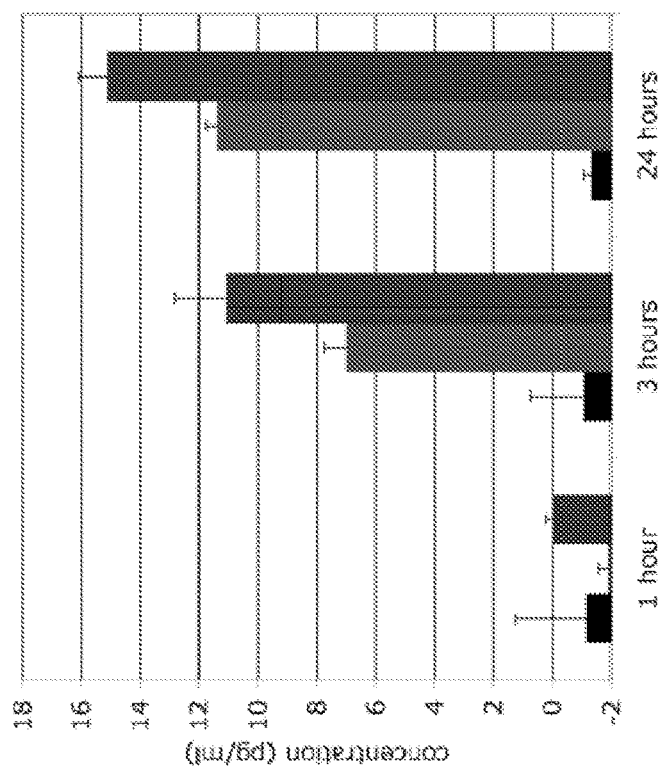
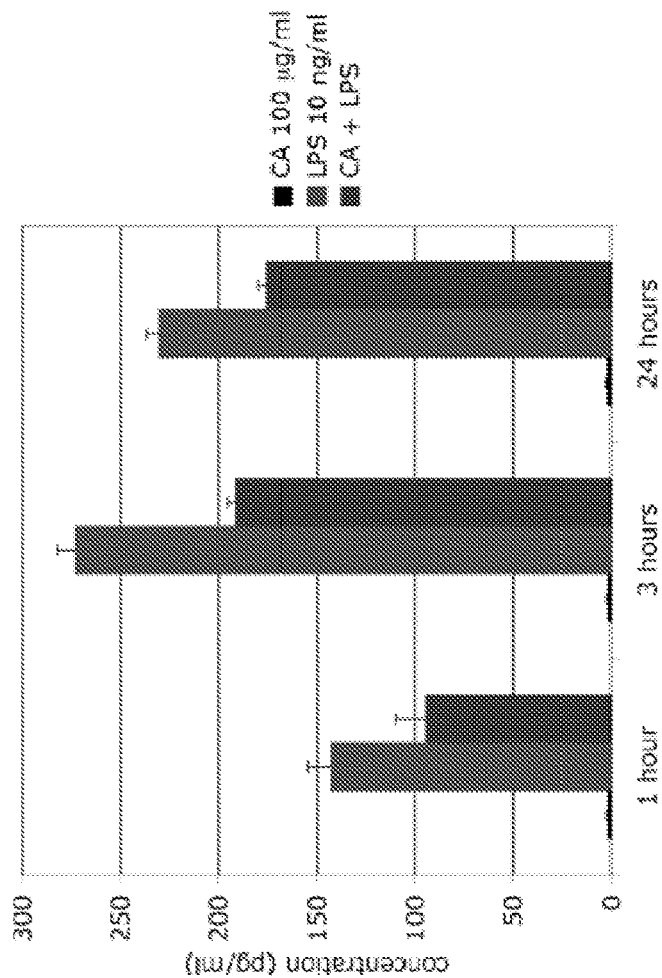
FIG. 27

COMPOSITIONS AND METHODS OF USE FOR WOUND HEALING

CLAIM OF PRIORITY

The present application is a national stage application under 35 U.S.C. § 371 of International Application No. PCT/US2014/028120, filed Mar. 14, 2014, published as International Publication No. WO2014/172040 on Oct. 23, 2014, which claims priority under 35 U.S.C. § 119(e) to U.S. provisional patent application U.S. Ser. No. 61/799,751, filed Mar. 15, 2013, each of which is incorporated herein by reference.

FIELD OF THE INVENTION

The invention relates to compositions and methods comprising water soluble polyglucosamine and derivatized polyglucosamine and their use to treat a wound in a subject.

BACKGROUND OF INVENTION

Wounds can cast severe physical, emotional and financial burdens on patients. In humans and other animals, wound injury triggers a series of intricate biological events towards wound healing. Poor wound healing can increase the morbidity and mortality rate, for example, in subjects with chronic disease. Bacterial infections in both acute and chronic wounds are an increasing concern because they reduce healing, increase patient cost and are often untreatable due to the rise in antibiotic resistance.

SUMMARY OF INVENTION

The present invention provides methods of treating a wound, e.g., a topical wound, e.g., a wound of the skin, in a subject, wherein the method comprises topically administering to the wound an aqueous composition comprising a polyglucosamine or a derivatized polyglucosamine such as PAAG, to thereby treat the wound in the subject, e.g., a human subject. In some embodiments, the present invention provides methods of treating the wound with an aqueous composition of PAAG at specified concentrations, e,g, at a concentration of about 50 to about 1000 µg/mL (or ppm) (e.g., from about 100 to about 800 µg/mL (or ppm), about 100 to about 600 µg/mL (or ppm)). In some embodiments, the concentration is about 50 µg/mL (or ppm) to about 400 µg/mL (or ppm), about 100 µg/mL (or ppm) to about 300 µg/mL (or ppm), e.g., about 150 µg/mL (or ppm) to about 250 µg/mL (or ppm), e.g., about 200 µg/mL (or ppm). In some embodiments, the concentration is about 200 µg/mL (or ppm). In some embodiments, the concentration is about 300 µg/mL (or ppm) to about 800 µg/mL (or ppm), about 350 µg/mL (or ppm) to about 750 µg/mL (or ppm), about 400 µg/mL (or ppm) to about 700 µg/mL (or ppm), about 450 µg/mL (or ppm) to about 650 µg/mL (or ppm), e.g., about 500 µg/mL (or ppm). In some embodiments, the concentration is about 500 µg/mL (or ppm).

In another aspect, the present invention provides methods of treating an infected wound, e.g., a topical wound, e.g., an infected wound of the skin with a higher concentration of PAAG. In some embodiments, the higher concentration is about 300 µg/mL (or ppm) to about 800 µg/mL (or ppm), about 350 µg/mL (or ppm) to about 750 µg/mL (or ppm), about 400 µg/mL (or ppm) to about 700 µg/mL (or ppm), about 450 µg/mL (or ppm) to about 650 µg/mL (or ppm), e.g., about 500 µg/mL (or ppm). In some embodiments, the concentration is about 500 µg/mL (or ppm).

In some embodiments, the infected wound is a chronic wound. In some embodiments, the infected wound is an acute wound.

In another aspect, the present invention provides methods of treating a non-infected wound, e.g., a topical wound, e.g., a non-infected wound of the skin with a lower concentration of PAAG. In some embodiments, the concentration is about 50 µg/mL (or ppm) to about 400 µg/mL (or ppm), about 100 µg/mL (or ppm) to about 300 µg/mL (or ppm), e.g., about 150 µg/mL (or ppm) to about 250 µg/mL (or ppm), e.g., about 200 µg/mL (or ppm). In some embodiments, the concentration is about 200 µg/mL (or ppm). In some embodiments, the non-infected wound is a chronic wound. In some embodiments, the non-infected wound is an acute wound.

Compositions comprising water soluble polyglucosamine or a derivatized polyglucosamine such as poly (acetyl, arginyl) glucosamine or PAAG and related methods of use are described herein. Exemplary methods using the compositions described herein include, for example, methods of treating a wound (e.g., a topical wound (e.g., a wound of the foot or dermis)) in a subject (e.g., in humans, in domesticated animals or pets, in large animals, e.g., pachyderms, e.g., elephants, rhinoceros, tapirs). In some embodiments, the wound in a subject is caused by a chronic disease (e.g., chronic foot disease, e.g., cracked nails, abscesses, lesions, ulcers, fissures), chronic non-healing dermal or subdermal wounds, (e.g., caused by chronic inflammation, pressure, damage, or a bacterial species), a wound comprising e.g., a cracked nail, abscess, lesion, ulcer, pressure sore, or fissure, a burn, a surgical wound, chronic dermal lesion, a wound caused by e.g., a traumatic injury, puncture, abrasion, laceration, incision, scrape, excision, a wound caused by e.g., pressure, stasis, venous, or diabetic ulceration.

The wound can be treated topically, for example, using an aqueous solution of a water soluble polyglucosamine or a derivatized polyglucosamine such as a polyglucosamine compound described herein. In some embodiments, the wound being treated is not infected (e.g., chronic non-infected, acute non-infected) or is infected by bacterial species (e.g. chronic infected, acute infected). In some embodiments, the composition described herein can result in a synergistic effect when the composition is used to treat a wound in a subject in combination with a second agent. Wound dressings and medical devices comprising soluble polyglucosamine or a derivatized polyglucosamine such as poly (acetyl, arginyl) glucosamine or PAAG and related methods of use are also described herein.

In one aspect, the invention features a method of treating a wound (e.g., a topical wound (e.g., a wound of the foot or dermis)) in a subject, the method comprising topically administering to the wound an aqueous solution comprising (e.g., consisting essentially of or consisting of) PAAG and sterile water, thereby treating the wound in the subject.

In some embodiments, the subject is a human.

In some embodiments, the subject is immunocompromised.

In some embodiments, the subject is allergic to one or more antibiotics or antiseptics (e.g., the subject has antibiotic-resistant bacteria).

In some embodiments, the subject is in the family Elephantidae, Rhinocerotidae, or tapirs.

In some embodiments, the subject is a domesticated animal or pet (e.g., horse, dog, cow, sheep, or cat).

In some embodiments, the solution is administered in a volume sufficient to moisten the wound. In some embodiments, the solution is administered in a volume sufficient to wash the wound (e.g., rinse substance from the wound).

In some embodiments, the concentration of the PAAG in the solution is from about 50 to about 1000 µg/mL (or ppm) (e.g., from about 100 to about 800 µg/mL (or ppm), about 100 to about 600 µg/mL (or ppm)).

In some embodiments, the wound is caused by a chronic disease (e.g., a chronic foot disease or chronic infection). In some embodiments, the wound is a chronic and non-healing dermal or subdermal wound (e.g., caused by chronic inflammation, pressure, damage, or a bacterial species). In some aspects of these embodiments, the wound comprises a cracked nail, abscess, lesion, ulcer, pressure sore, or fissure. In some aspects of these embodiments, the wound is a chronic dermal lesion.

In some embodiments, the wound is a burn. In some embodiments, the wound is a surgical wound.

In some embodiments, the wound is caused by a traumatic injury.

In some embodiments, the wound is a puncture, abrasion, laceration, incision, scrape, or excision.

In some embodiments, the wound is a pressure, stasis, venous, or diabetic ulceration. In some embodiments, the wound is infected with bacteria. In some aspects of these embodiments, the bacteria is *E. coli*, MRSA, *Kelbsiella pneumonia*, VRE, Mupirocin resistant MRSA, *Staphylococcus aureus* or *Pseudomonas aeruginosa* or combination thereof.

In some embodiments, the wound is an infected wound. In some aspects of these embodiments, the wound is a chronic wound. In some aspects of these embodiments, the wound is an acute wound. In some aspects of these embodiments, the concentration of the PAAG in the solution is from about 50 to about 1000 µg/mL (or ppm) (e.g., from about 100 to about 800 µg/mL (or ppm), about 150 to about 550 µg/mL (or ppm), or about 500 µg/mL (or ppm)). In some aspects of these embodiments, the solution is administered daily. In some aspects of these embodiments, the solution is administered 1, 2, or 3 times a day. In some aspects of these embodiments, the solution is administered every second or third day. In some aspects of these embodiments, the subject is treated until the wound is healed or closed. In some aspects of these embodiments, the subject is treated for about 2 to about 5 weeks. In some aspects of these embodiments, the subject is treated for about 6 to about 12 weeks. In some aspects of these embodiments, subject is treated for about 1 week. In some aspects of these embodiments, the subject is treated for about 1 week to around 2 weeks. In some aspects of these embodiments, the method comprises administration of a second therapy. In some aspects of these embodiments, the second wound therapy is selected from the group consisting of an antibiotic or antibacterial use, a steroidal or non-steroidal anti-inflammatory drug, debridement, irrigation, negative pressure wound therapy, warming, oxygenation, moist wound healing, removing mechanical stress, and adding cells to secrete or enhance levels of healing factors. In some aspects of these embodiments, the second therapy is a systemic antibiotic or steroidal treatment. In some aspects of these embodiments, the method does not comprise administration of a second therapy.

In some embodiments, the wound is a non-infected wound. In some aspects of these embodiments, the wound is a chronic wound. In some aspects of these embodiments, the wound is an acute wound. In some aspects of these embodiments, the concentration of the PAAG in the solution is from about 50 to about 800 µg/mL (or ppm) (e.g., from about 50 to about 500 µg/mL (or ppm), about 100 to about 350 µg/mL (or ppm), or about 200 µg/mL (or ppm)). In some aspects of these embodiments, the solution is administered daily. In some aspects of these embodiments, the solution is administered 1, 2, or 3 times a day. In some aspects of these embodiments, the subject is treated until the wound is healed or closed. In some aspects of these embodiments, the subject is treated for about 2 weeks to about 5 weeks. In some aspects of these embodiments, the subject is treated for about 6 weeks to about 12 weeks. In some aspects of these embodiments, the subject is treated for about 1 week. In some aspects of these embodiments, the subject is treated for about 1 week to around 2 weeks. In some aspects of these embodiments, the method comprises administration of a second therapy.

In some embodiments, the method comprises administration of the PAAG at a concentration in the solution from about 50 to about 1000 µg/mL (or ppm) (e.g., from about 100 to about 800 µg/mL (or ppm), about 150 to about 550 µg/mL (or ppm), or about 500 µg/mL (or ppm)) for 1 week or 2 weeks, further comprising administration of the PAAG at a concentration in the solution from about 50 to about 800 µg/mL (or ppm) (e.g., from about 50 to about 500 µg/mL (or ppm), about 150 to about 400 µg/mL (or ppm), or about 300 µg/mL (or ppm)). until the wound is healed or closed. In some aspects of these embodiments, the method comprises administration of a second therapy. In some aspects of these embodiments, the second wound therapy is selected from the group consisting of an antibiotic or antibacterial use, a steroidal or non-steroidal anti-inflammatory drug, debridement, irrigation, negative pressure wound therapy, warming, oxygenation, moist wound healing, removing mechanical stress, and adding cells to secrete or enhance levels of healing factors. In some aspects of these embodiments, the second therapy is a systemic antibiotic or steroidal treatment. In some aspects of these embodiments, the method does not comprise administration of a second therapy.

In some embodiments, the method further comprises irrigating the wound.

In some embodiments, the method further comprises wound debridement (e.g., removing necrotic and or infected tissue).

In some embodiments, the method further comprises covering the wound.

In some embodiments, the method further comprises negative pressure therapy.

In some embodiments, the method reduces the healing time or increases the healing rate of the wound, for example, relative to a control (e.g., wherein the control is an untreated wound, a wound treated with a systemic antibiotic in the absence of PAAG, and/or a wound treated with a bandage in the absence of PAAG). In some aspects of these embodiments, the healing time of the wound is reduced by at least about 10% (e.g., at least about 20%, at least about 30%, at least about 40%, at least about 50%) compared to the healing time of the wound that has not been contacted with the solution. In some aspects of these embodiments, wherein the wound healing rate is increased by 1 day, 2 days, 3 days, 4 days, 5 day, 6 days, 1 week, or 1 month, compared to the healing rate of the wound that has not been contacted with the solution.

In some embodiments, the wound is inflamed, and the method decreases inflammation associated with the wound, for example, relative to a control (e.g., wherein the control is an untreated wound, a wound treated with a systemic antibiotic in the absence of PAAG, and/or a wound treated with a bandage in the absence of PAAG).

In some embodiments, the method improves the healing of the wound, wherein healing of the wound results in inflammation, and wherein the inflammation resulting from the healing of the wound is reduced, for example, relative to a control (e.g., wherein the control is an untreated wound, a wound treated with a systemic antibiotic in the absence of PAAG, and/or a wound treated with a bandage in the absence of PAAG).

In some embodiments, the method decreases the magnitude or extent of scarring, for example, relative to a control (e.g., wherein the control is an untreated wound, a wound treated with a systemic antibiotic in the absence of PAAG, and/or a wound treated with a bandage in the absence of PAAG).

In some embodiments, the wound, upon treatment, has a reduced bacterial load, for example, relative to a control (e.g., wherein the control is an untreated wound, a wound treated with a systemic antibiotic in the absence of PAAG, and/or a wound treated with a bandage in the absence of PAAG).

In some embodiments, the method physically removes bacteria from the wound.

In some embodiments, the method comprises rinsing the wound to provide a covering of the wound with a thin layer of PAAG, wherein the thin layer of PAAG reduces the ability of bacteria to bind to the wound relative to a control (e.g., wherein the control is an untreated wound, a wound treated with a systemic antibiotic in the absence of PAAG, and/or a wound treated with a bandage in the absence of PAAG). In some aspects of these embodiments, the thin layer of PAAG remains on the wound for 3 hrs, 6 hrs, or 12 hours. In some aspects of these embodiments, the thin layer of PAAG reduces the ability of bacteria to bind the wound for 3 hrs, 6 hrs, or 12 hours. In some aspects of these embodiments, the thin layer of PAAG reduces the ability of bacteria to infect the wound for 3 hrs, 6 hrs, or 12 hours. In some aspects of these embodiments, the thin layer of PAAG reduces the ability of bacteria to colonize the wound for 3 hrs, 6 hrs, or 12 hours.

In some embodiments, the method is not harmful to the environment.

In some embodiments, the method does not result in the selection of bacteria that are resistant to one or more antibiotics (e.g., the method does not result in selective killing of bacteria such that the subject is left with bacteria that are resistant to one or more antibiotics). In some embodiments, the method does not contribute to antibiotic resistance.

In some embodiments, the method further comprises monitoring the subject (e.g., for bacterial cleaniness, for an indication of successful wound healing). In some aspects of these embodiments, the monitoring the subject comprises measuring the abundance and type of bacterium present in the subject. In some aspects of these embodiments, the monitoring the subject comprises measuring CFUs of bacteria. In some aspects of these embodiments, the monitoring the subject determines the length of treatment.

In one aspect, the invention features a method of promoting wound healing in a subject, the method comprising topically administering to the wound an aqueous solution comprising (e.g., consisting essentially of or consisting of) PAAG and sterile water, thereby promoting wound healing.

In one aspect, the invention features a solution comprising (e.g., consisting essentially of, consisting of) a poly (acetyl, arginyl) glucosamine (PAAG) and sterile water, wherein the solution is substantially free of impurities.

In some embodiments, PAAG comprises the following formula (I):

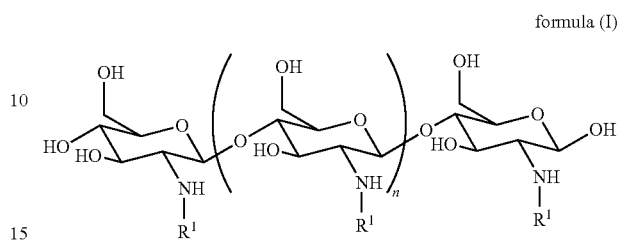

formula (I)

wherein:
n is an integer between 20 and 6000; and
each $R^1$ is independently selected for each occurrence from hydrogen, acetyl,

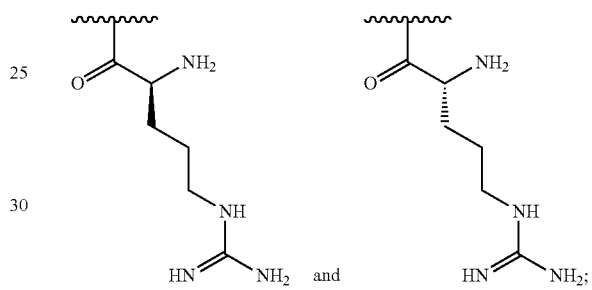

and wherein at least 25% of $R^1$ substituents are H, at least 1% of $R^1$ substituents are acetyl, and at least 2% of $R^1$ substituents are

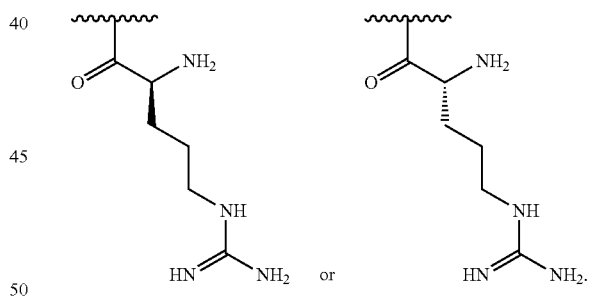

or

In some aspects of these embodiments, the molecular weight of the PAAG is from 20 to 150 kDa. In some aspects of these embodiments, the molecular weight of the PAAG is from 20 to 120 kDa. In some aspects of these embodiments, the molecular weight of the PAAG is from 30 to 120 kDa. In some aspects of these embodiments, the molecular weight of the PAAG is from 50 to 100 kDa. In some aspects of these embodiments, the molecular weight of the PAAG is from 20 to 80 kDa.

In some aspects of these embodiments, the polydispersity index of the PAAG is from 1.0 to 2.5.

In some aspects of these embodiments, the pH is about 7 to about 8.

In some aspects of these embodiments, the PAAG is arginine functionalized (i.e., arginine-functionalized) at least 18%. In some aspects of these embodiments, the PAAG is functionalized (i.e., arginine-functionalized) at between 18% and 30%. In some aspects of these embodiments, the PAAG is greater than 18% functionalized (i.e., arginine-functionalized).

In one aspect, the invention features a method of making a solution of PAAG, wherein the method comprises adding an aqueous vehicle to and dissolving a composition of PAAG.

In some embodiments, the aqueous vehicle is sterile water. In some aspects of these embodiments, the method further comprises adding a non-active agent (e.g., a wetting agent, thickening agent).

In some embodiments, the composition of PAAG is dissolved in a volume sufficient to moisten a wound.

In some embodiments, the solution is administered in a volume sufficient to wash the wound (e.g., rinse substance from the wound).

In one aspect, the invention features a kit comprising a composition of PAAG and instructions for preparing a solution of PAAG.

In some embodiments, the kit is for use in treating a wound.

In some embodiments, the composition of PAAG is provided in a bottle (e.g., amber glass bottle).

BRIEF DESCRIPTIONS OF THE DRAWINGS

FIG. 1 Elephant #1 foot pad wound healing progression over a months treatment with 200 µg/mL PAAG Active Rinse. A) Initial injury Oct. 17, 2009, B) 7 days post treatment Mar. 20, 2010, C) 14 days treatment Mar. 27, 2010, D) 24 days treatment Apr. 10, 2010, E) 66 days treatment May 22, 2010, F) Healed foot pad Jul. 17, 2010.

Figure 2:

FIG. 2 Elephant #2 treated daily with 200 µg/mL PAAG Active Rinse for chronic lesion on left front nail #4. All images are of the lesion post-debridement (trimmed) A) Lesion prior to treatment with PAAG Active Rinse Nov. 28, 2009, B) Lesion, 2 weeks daily chitosan-arginine treatment May 15, 2010, C) Lesion, 5 weeks daily treatment Jun. 5, 2010, D) Lesion, 7 weeks daily treatment Jun. 17, 2010, E) Lesion, 11 weeks daily treatment Jul. 17, 2010, F) Current resolution.

FIG. 3 Impacted temporal gland of elephant #2 treated with 200 µg/mL PAAG Active Rinse wound rinse. A) Demonstrates the wound spray administration via hand held pump. B) Demonstrates the wound irrigation using a syringe.

Figure 4:

FIG. 4 Elephant #3 with a chronic ulcer on the bottom of her left rear #4 nail (A). Panels B and C show the progressive wound healing following twice daily treatment with PAAG Active Rinse at 500 µg/mL for 9 months.

Figure 5:
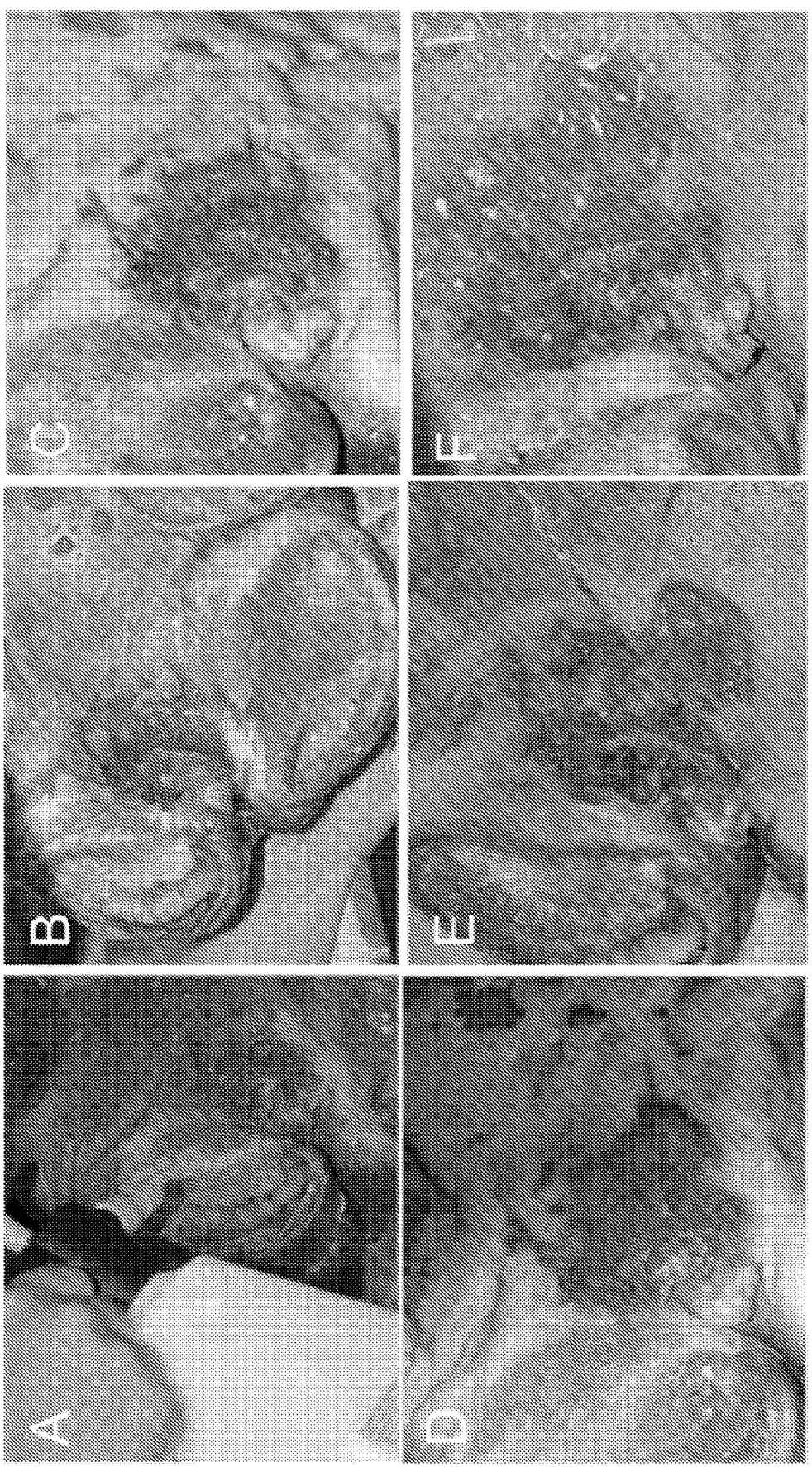

FIG. 5 Rhinoceros (female 34 years-old) with deep abscess on the bottom of the left foot. This panel of images show the progression of healing observed upon daily treatment with PAAG Active Rinse wound rinse. A) First treatment Jul. 16, 2010, B) 1 week after treatment Jul. 23, 2020, C) 3 weeks after treatment Aug. 6, 2010, D) 5 weeks after treatment Aug. 17, 2010, E) 7 weeks after treatment, F) 14 weeks after treatment wound resolved.

Figure 6:

FIG. 6 Rhinoceros (female 34 years-old) with pressure ulcer located on hips (left hip depicted above). This panel of images shows the weekly progression of wound healing observed upon daily treatment with PAAG Active Rinse wound rinse. A) Sep. 30, 2010, B) Oct. 5, 2010, C) Oct. 12, 2010, D) Oct. 19, 2010, and E) Nov. 2, 2010.

Figure 7:
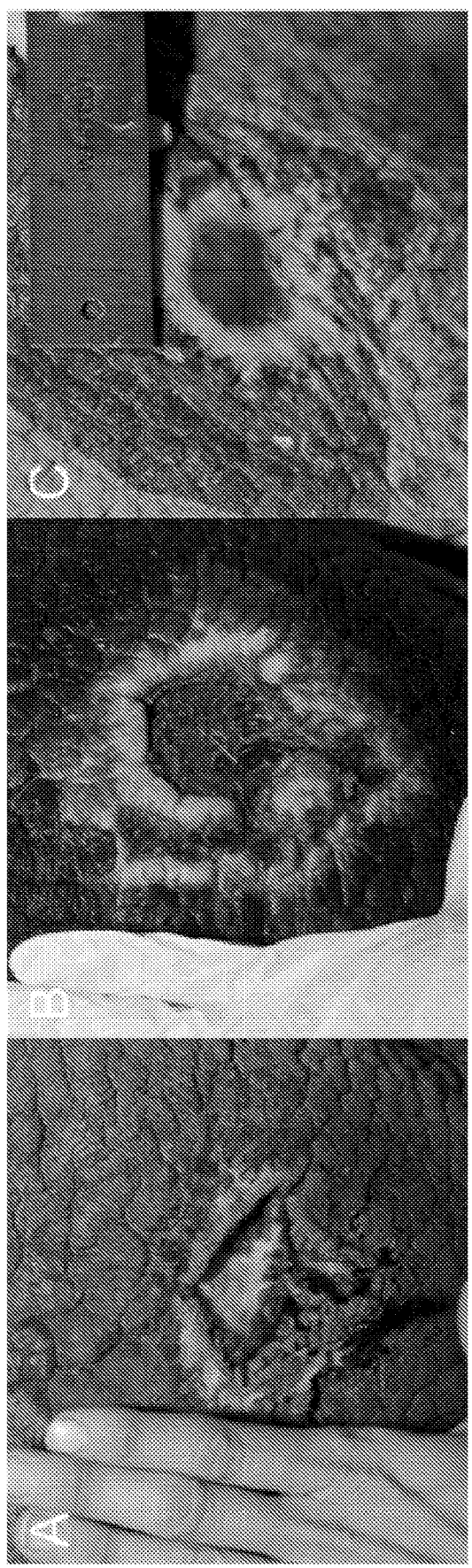

FIG. 7 Rhinoceros #1 with a chronic pressure ulcer on her left hip that developed a MRSA infection. Panels A-C show the progressive wound healing following twice daily treatment with PAAG Active Rinse at 500 µg/mL for six weeks. PAAG Active Gel was applied daily beginning Dec. 2, 2010. A) Nov. 9, 2010, B) Nov. 23, 2010, and C) Dec. 14, 2010.

Figure 8:
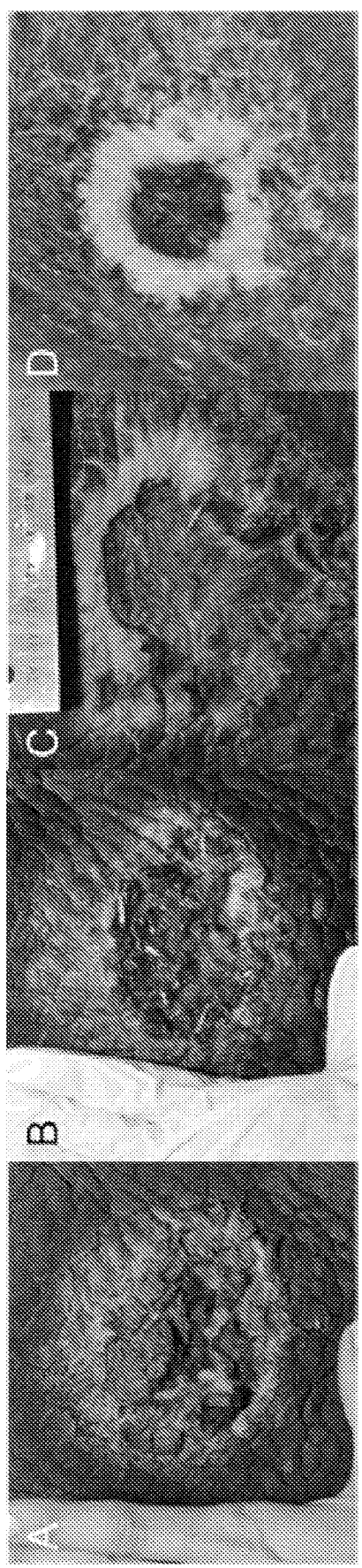

FIG. 8 Rhinoceros #1 with a chronic pressure ulcer on her right hip that developed a MRSA infection. Panels A-D show the progressive wound healing following twice daily treatment with PAAG Active Rinse (37.0 kDa, 22.8% functionalized PAAG) rinse at 500 µg/mL for six weeks. PAAG Active Gel was applied daily beginning Dec. 2, 2010. A) Nov. 9, 2010, B) Nov. 23, 2010, C) Dec. 14, 2010, and D) Dec. 21, 2010.

FIG. 9 Experimental study design of porcine partial thickness wound model.

Figure 10:
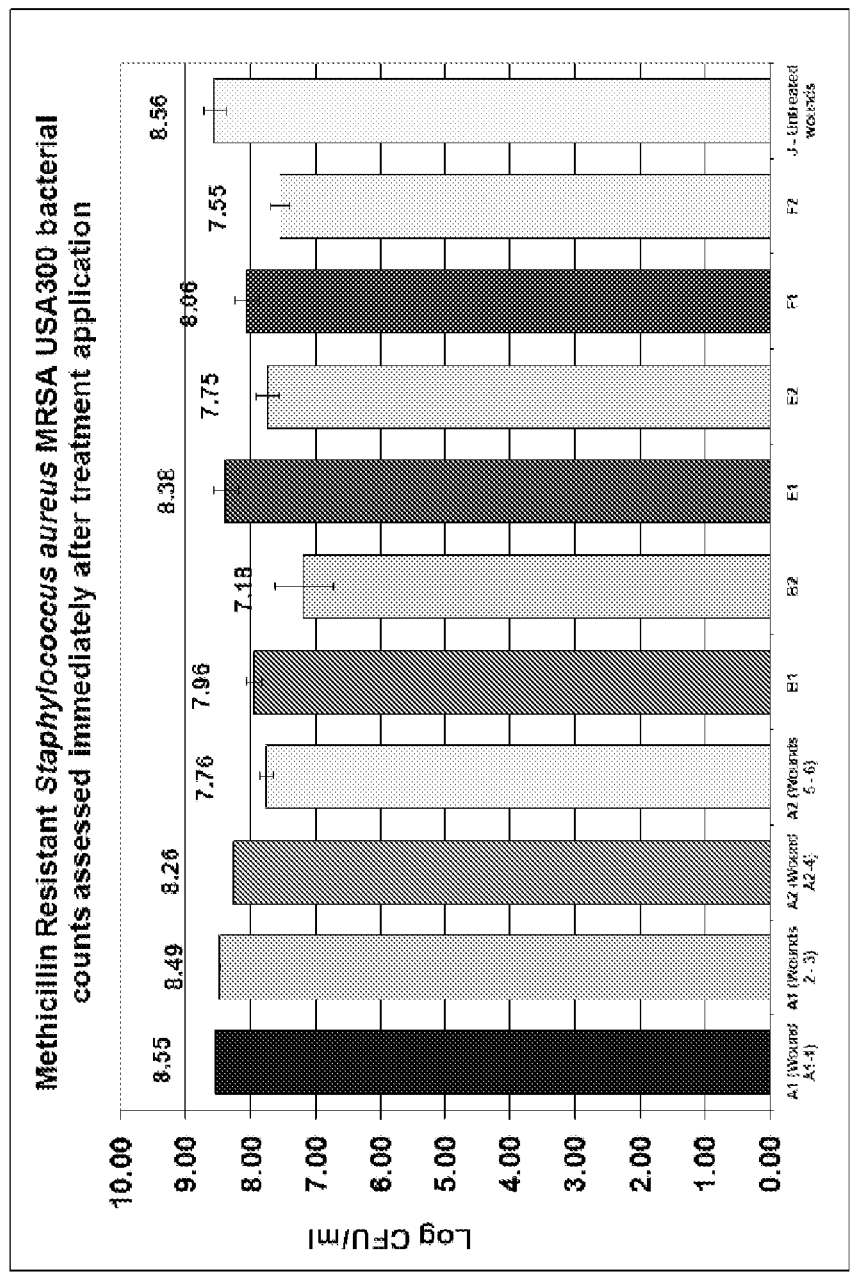

FIG. 10 MRSA examined immediately after PAAG treatment (rinse application).

Figure 11:
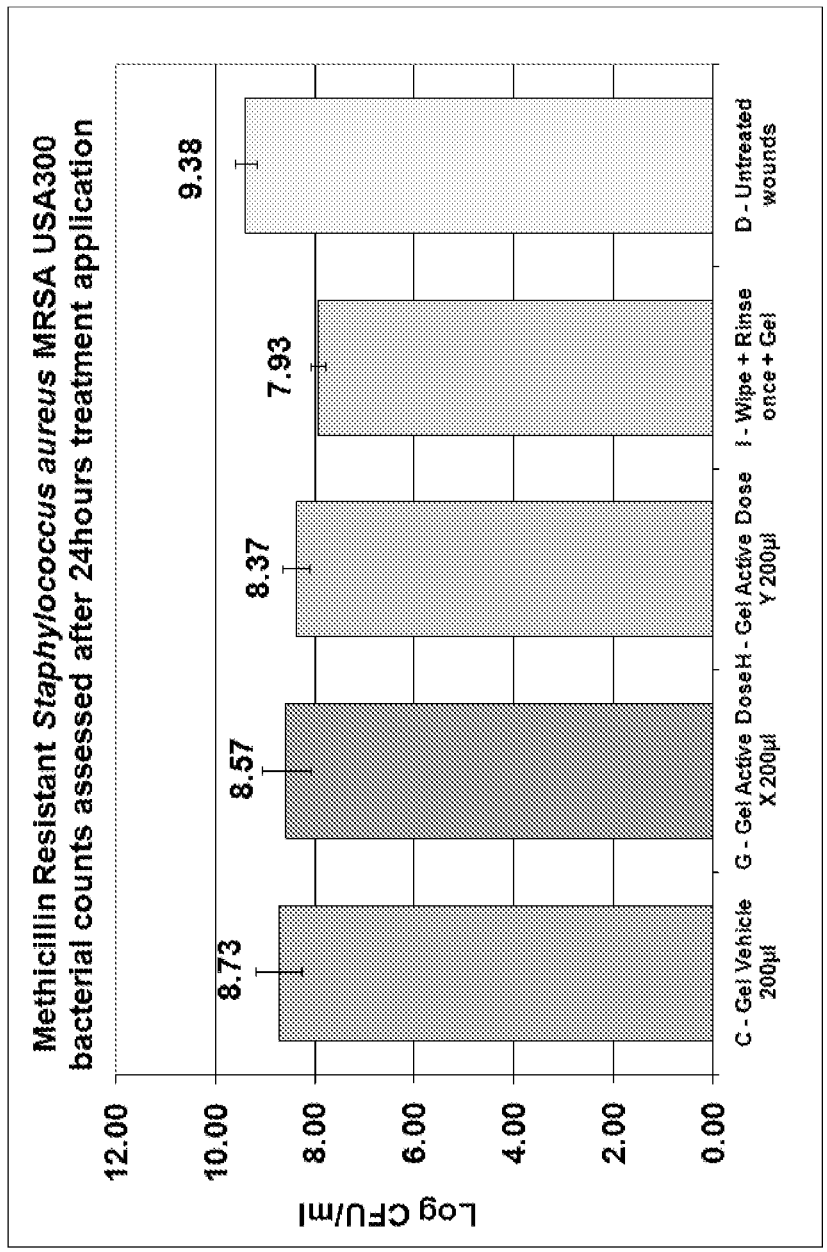

FIG. 11 MRSA examined 24 hours after PAAG treatment (rinse application).

Figure 12:
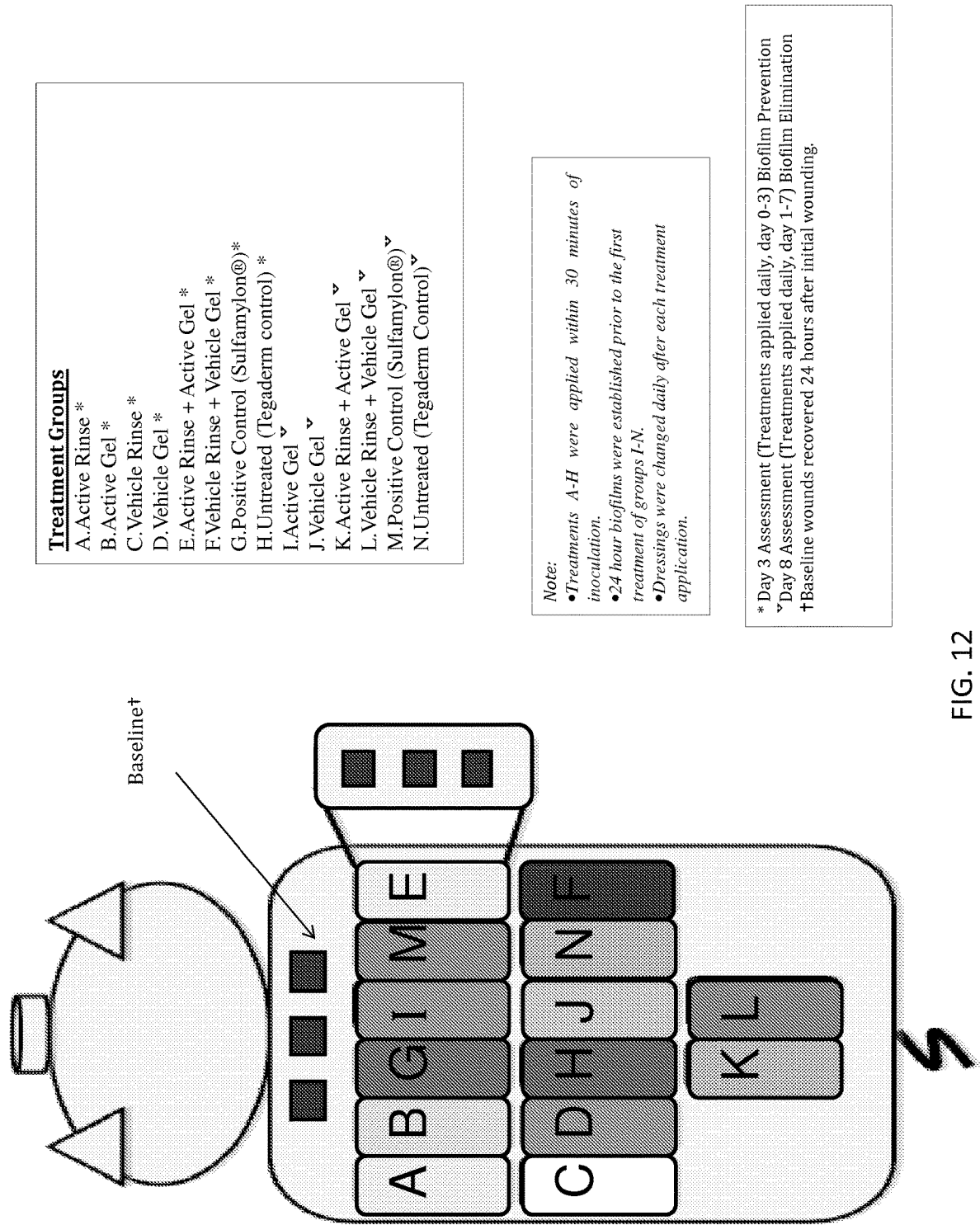

FIG. 12 Experimental study design of porcine partial thickness wound model.

Figure 13:
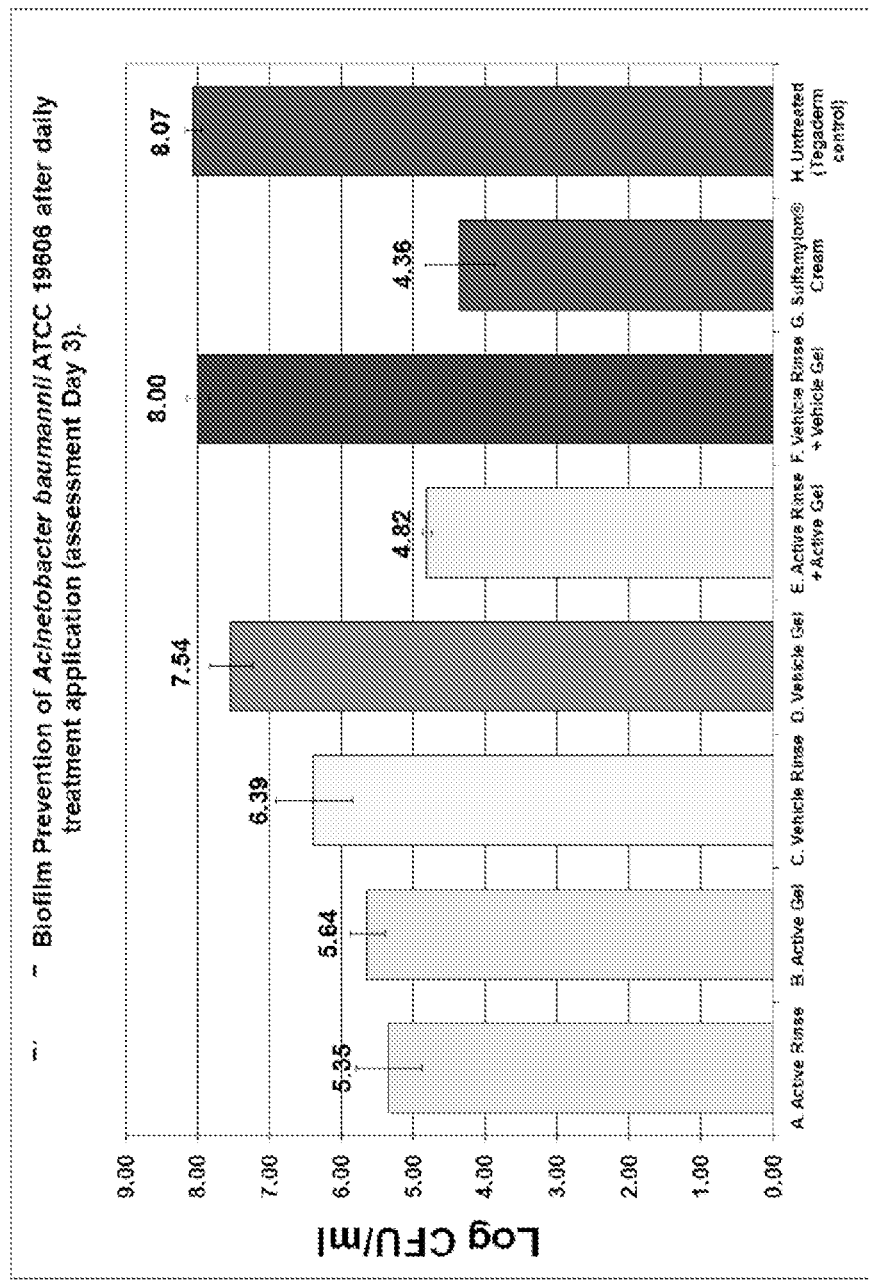

FIG. 13 Porcine partial thickness wound model using *Acinetobacter baumannii* examined after 3 of days treatment with different formulations of PAAG.

Figure 14:
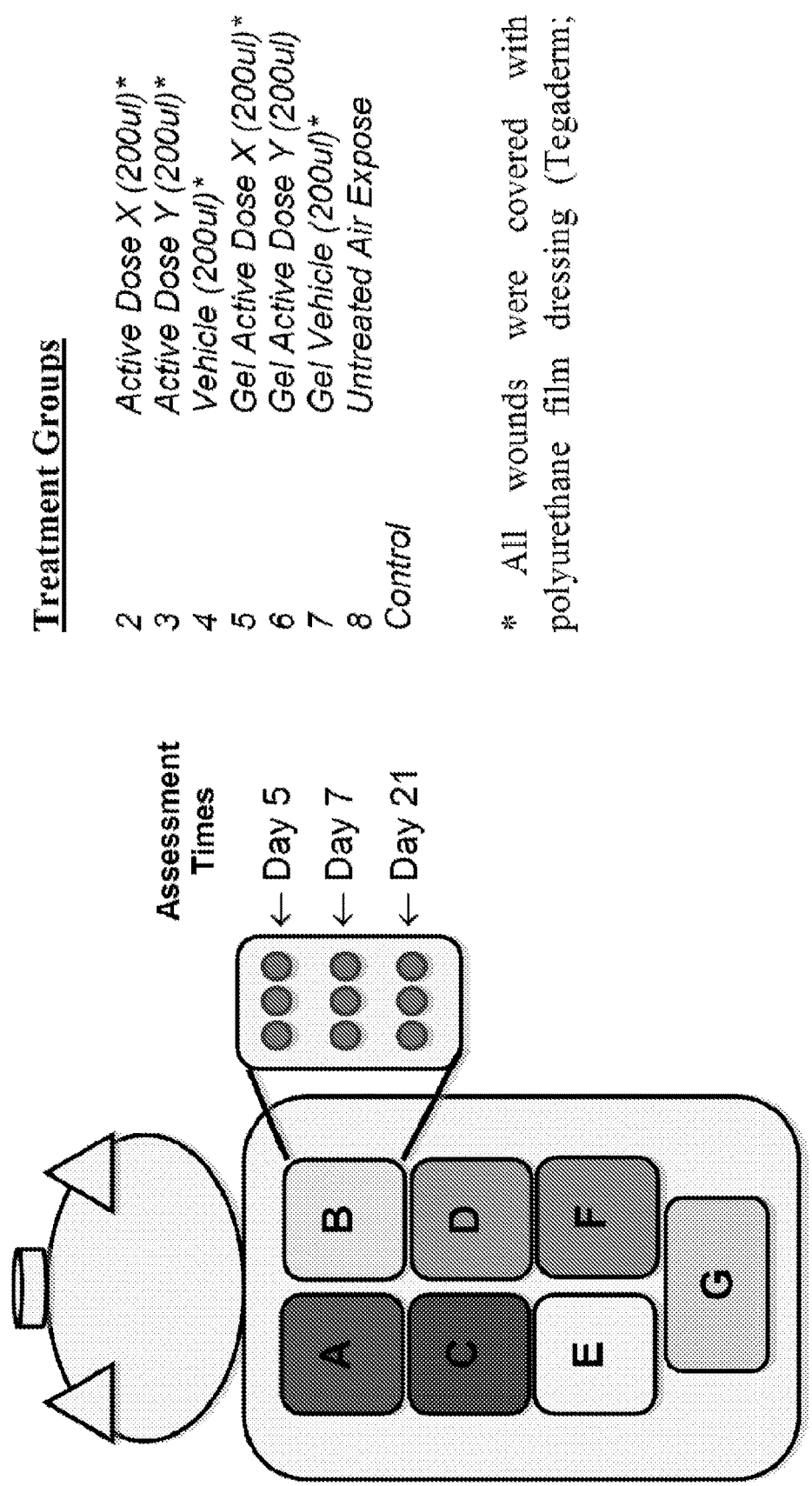

FIG. 14 Experimental study design of porcine burn wound model.

Figure 15:
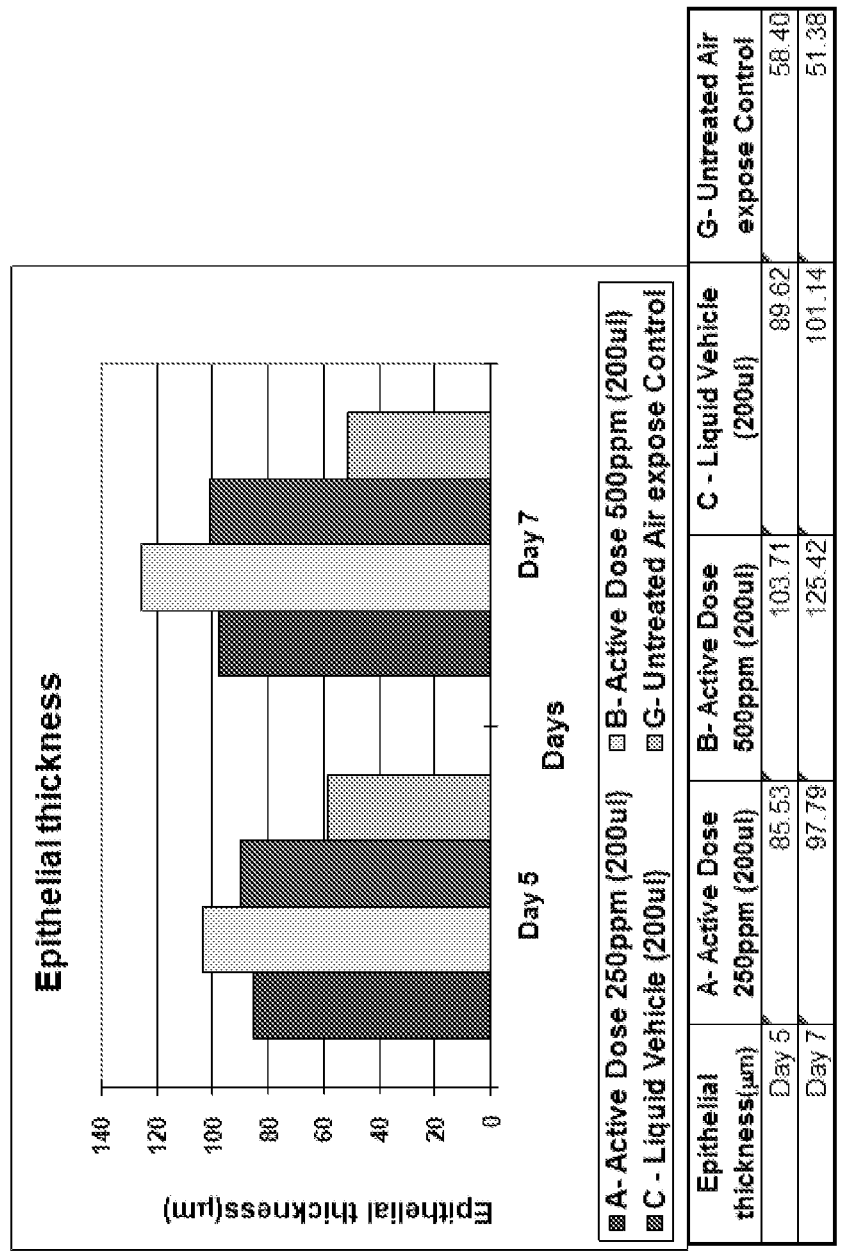

FIG. 15 Epithelial thickness assessed on Day 5 and 7 after PAAG (250 and 500 µg/mL) treatment.

Figure 16:
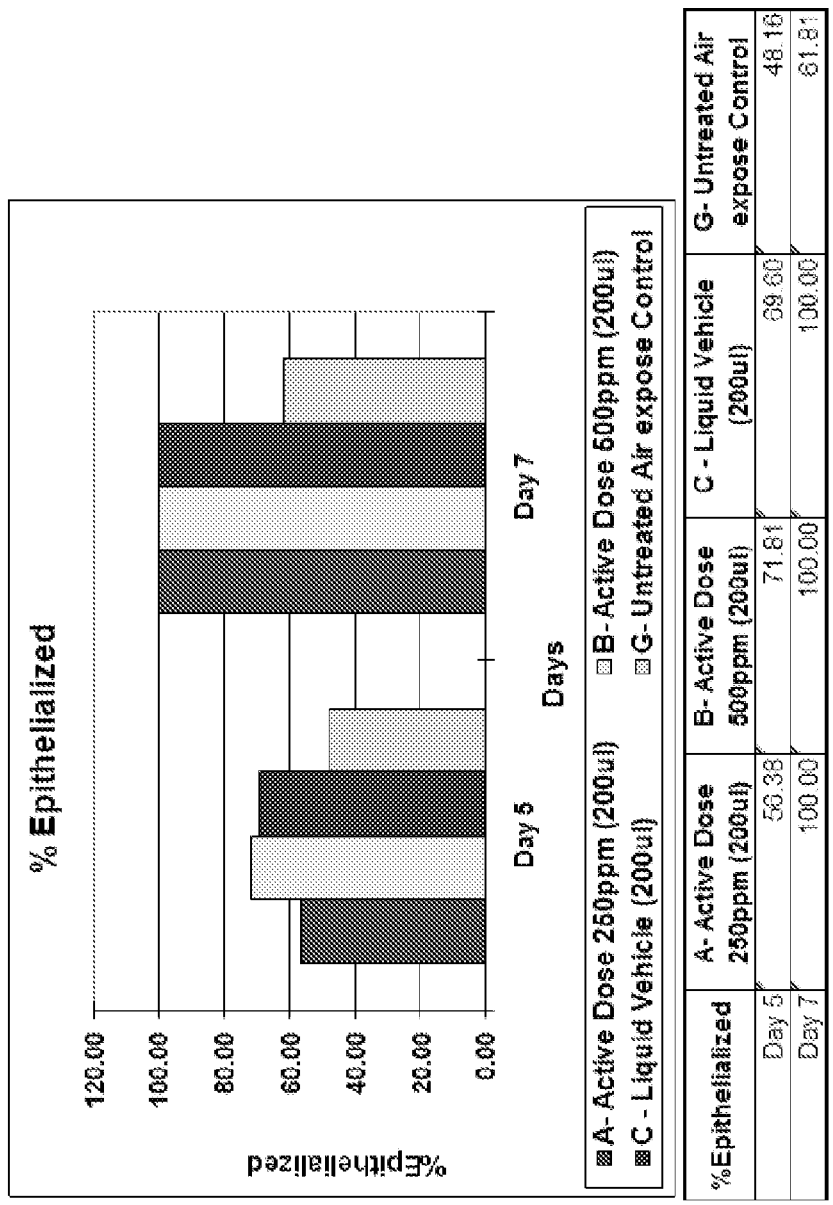

FIG. 16 Percent epithelialization assessed on Day 5 and 7 after PAAG (250 and 500 µg/mL) treatment.

Figure 17:
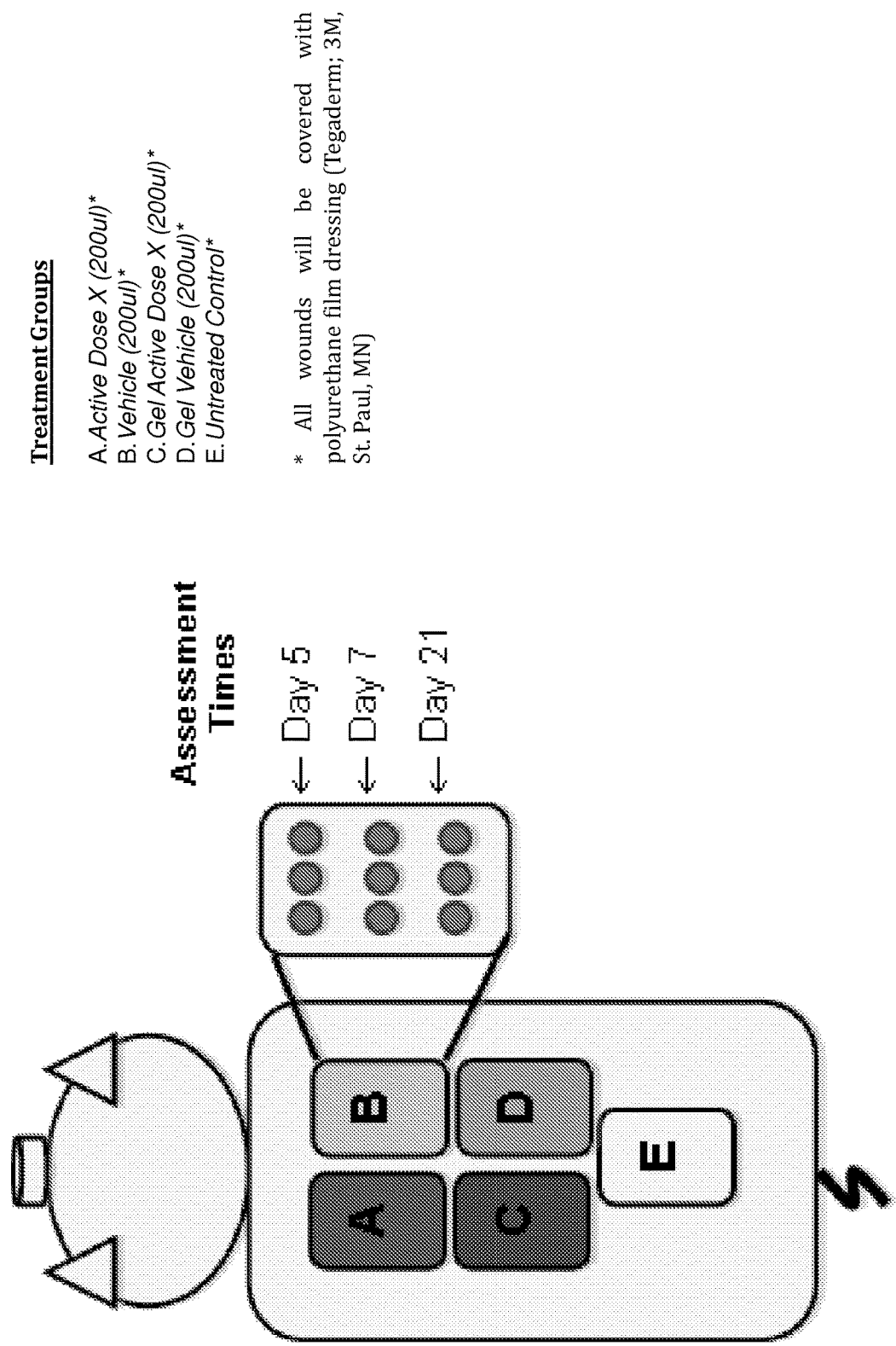

FIG. 17 Experimental study design of porcine punch wound model.

Figure 18:
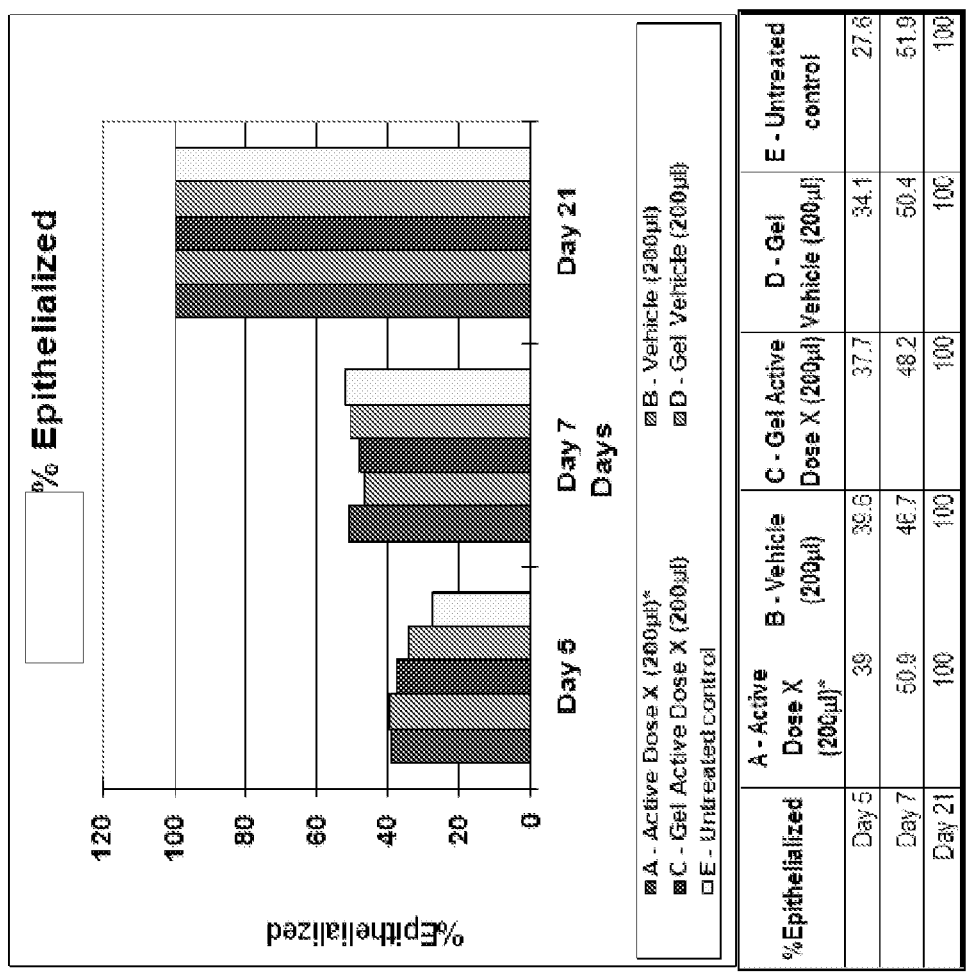

FIG. 18 Percent epithelialization assessed on Days 5, 7, and 21 after PAAG (rinse and gel, 200 µg/mL) treatment.

Figure 19:
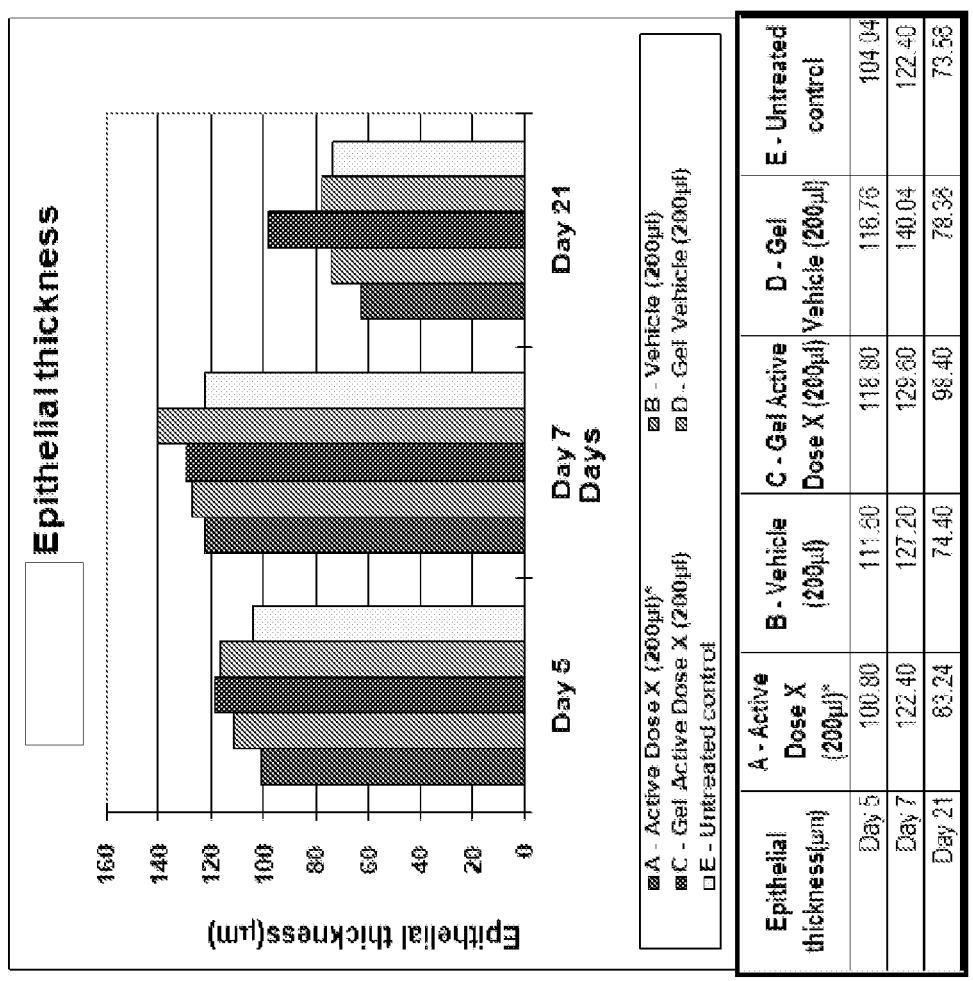

FIG. 19 Epithelial thickness assessed on Days 5, 7, and 21 after PAAG (rinse and gel, 200 µg/mL) treatment.

Figure 20:
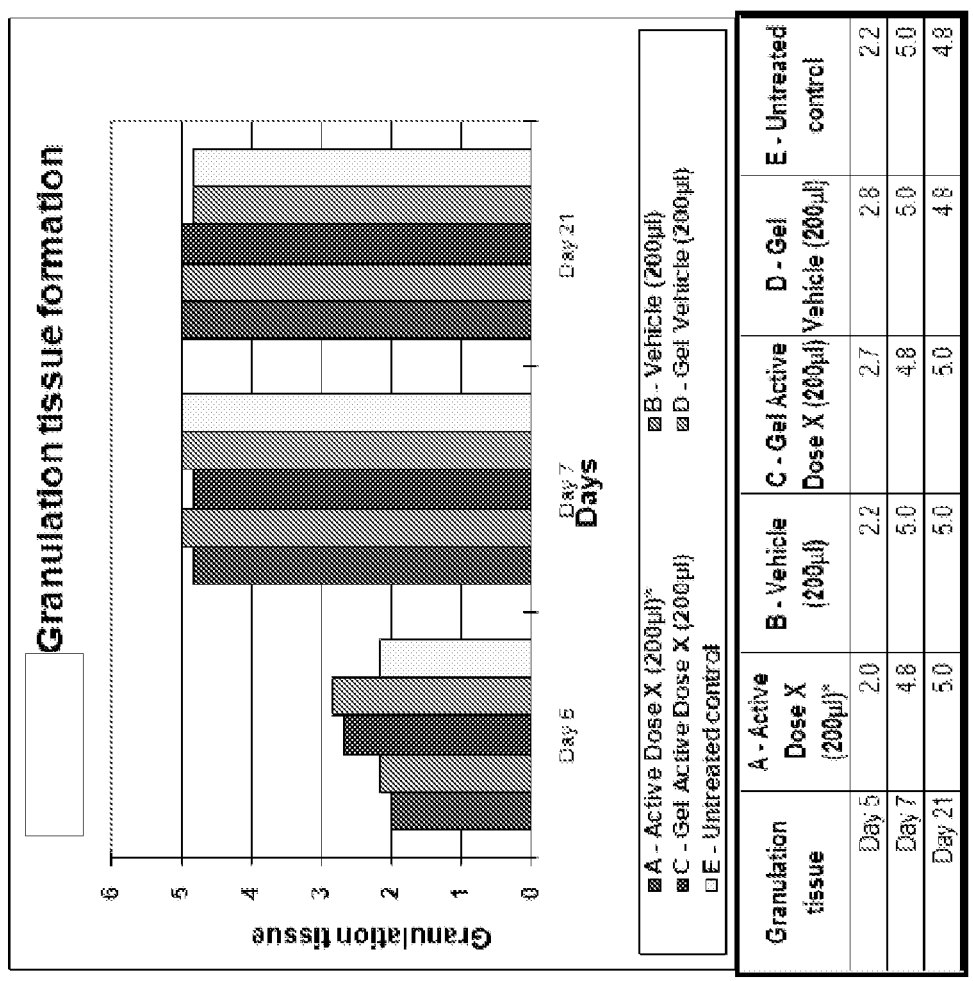

FIG. 20 Granulation tissue formation observed at Days 7 and 21 after PAAG (rinse and gel, 200 µg/mL) treatment.

Figure 21:
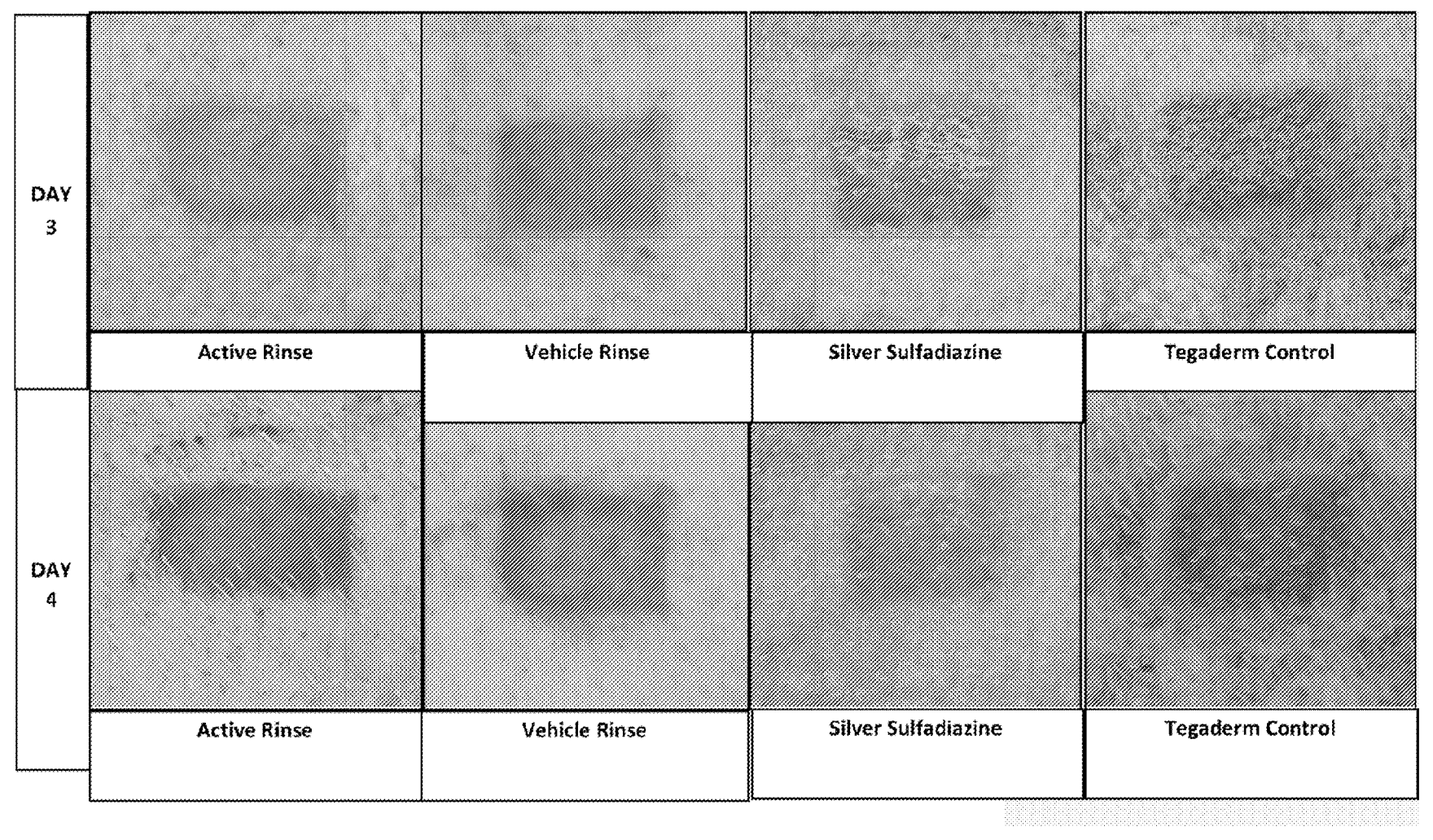

FIG. 21 Representative photos of *Acinetobacter baumannii* infected wounds over an assessment period.

Figure 22:
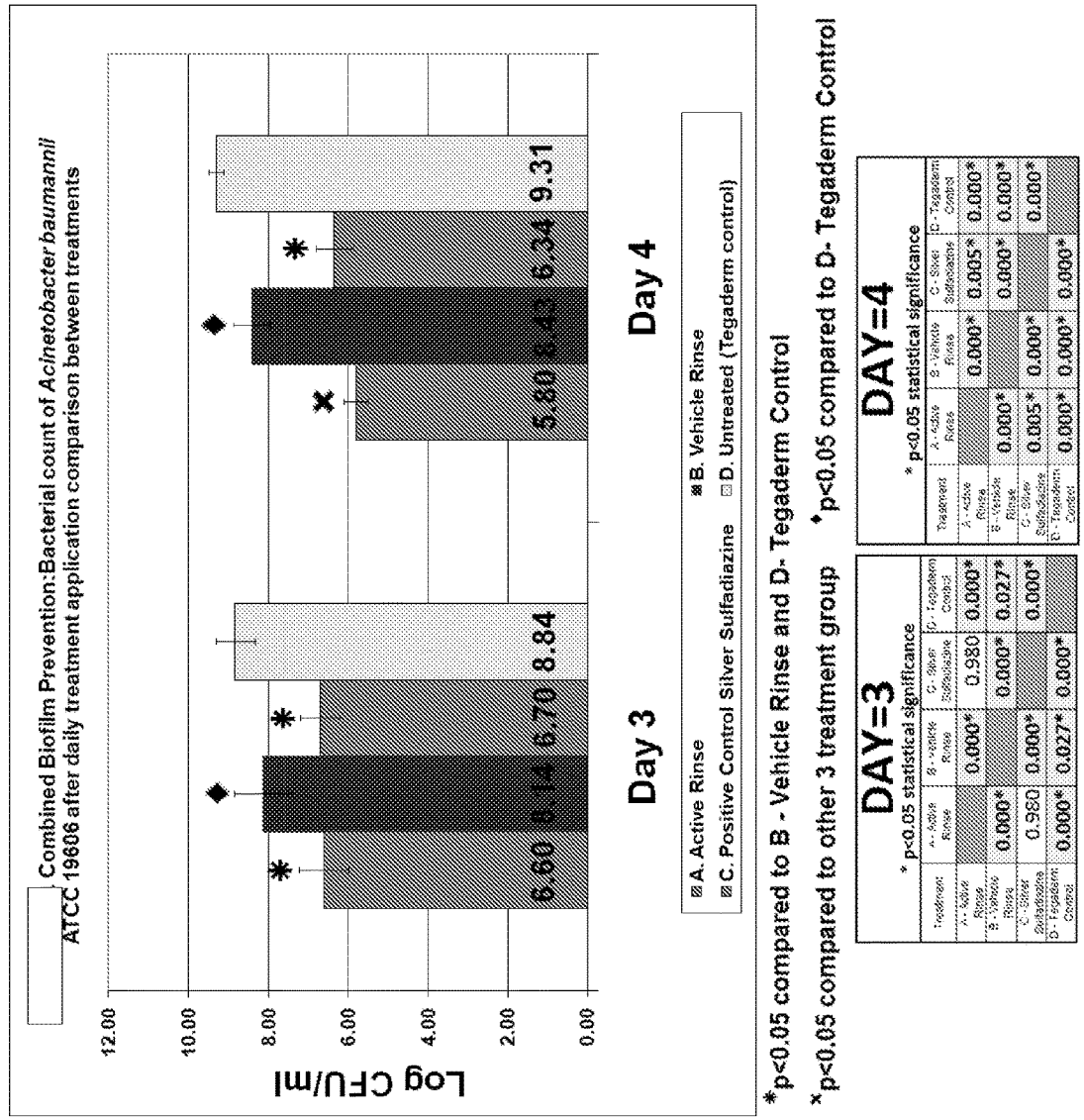

FIG. 22 Bacterial count of *Acinetobacter baumannii* after daily treatment assessed on Days 3 and 4 after PAAG treatment.

Figure 23:
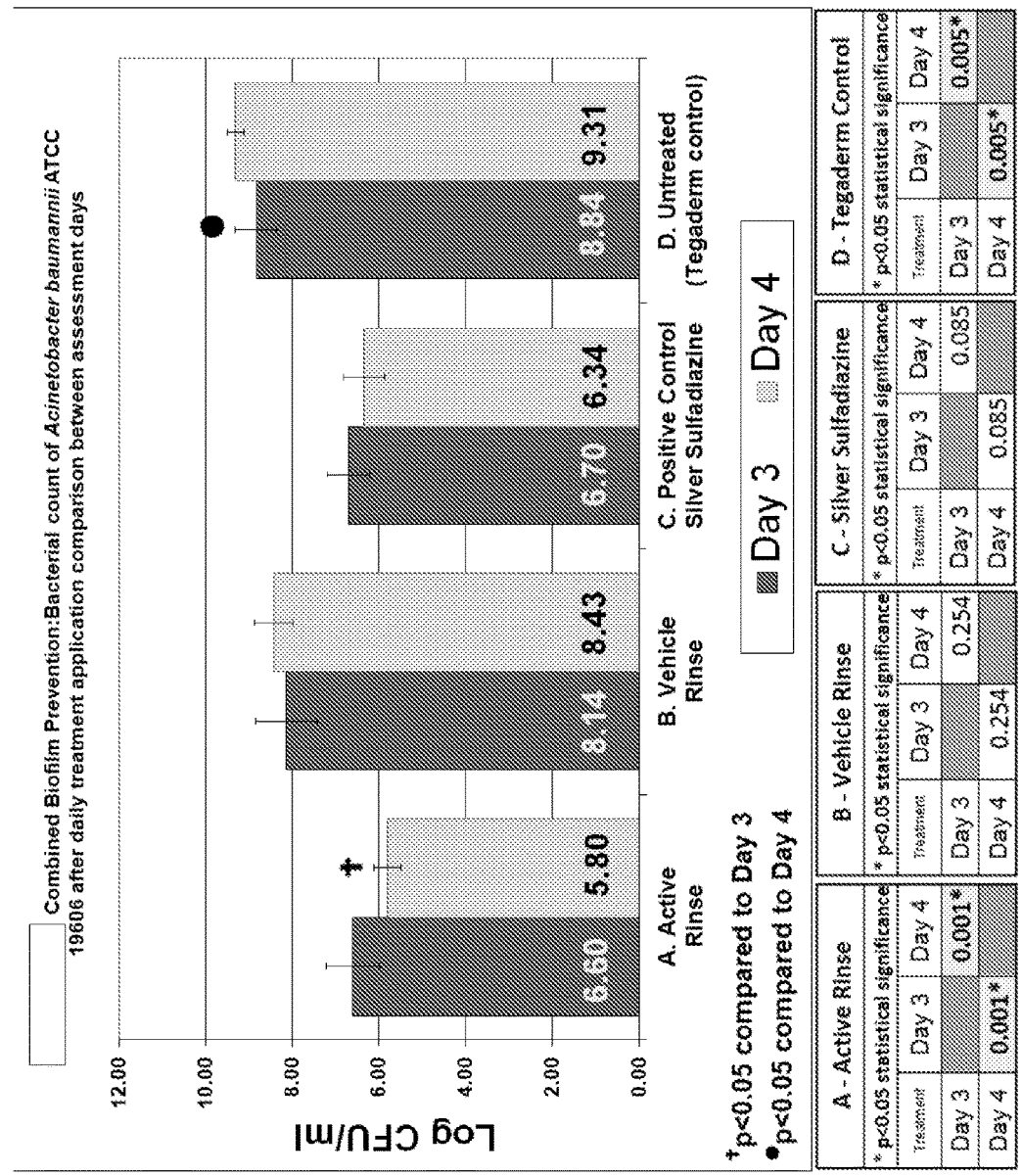

FIG. 23 Comparison of PAAG treated and untreated wounds infected with *Acinetobacter baumannii* across treatment days.

Figure 24:
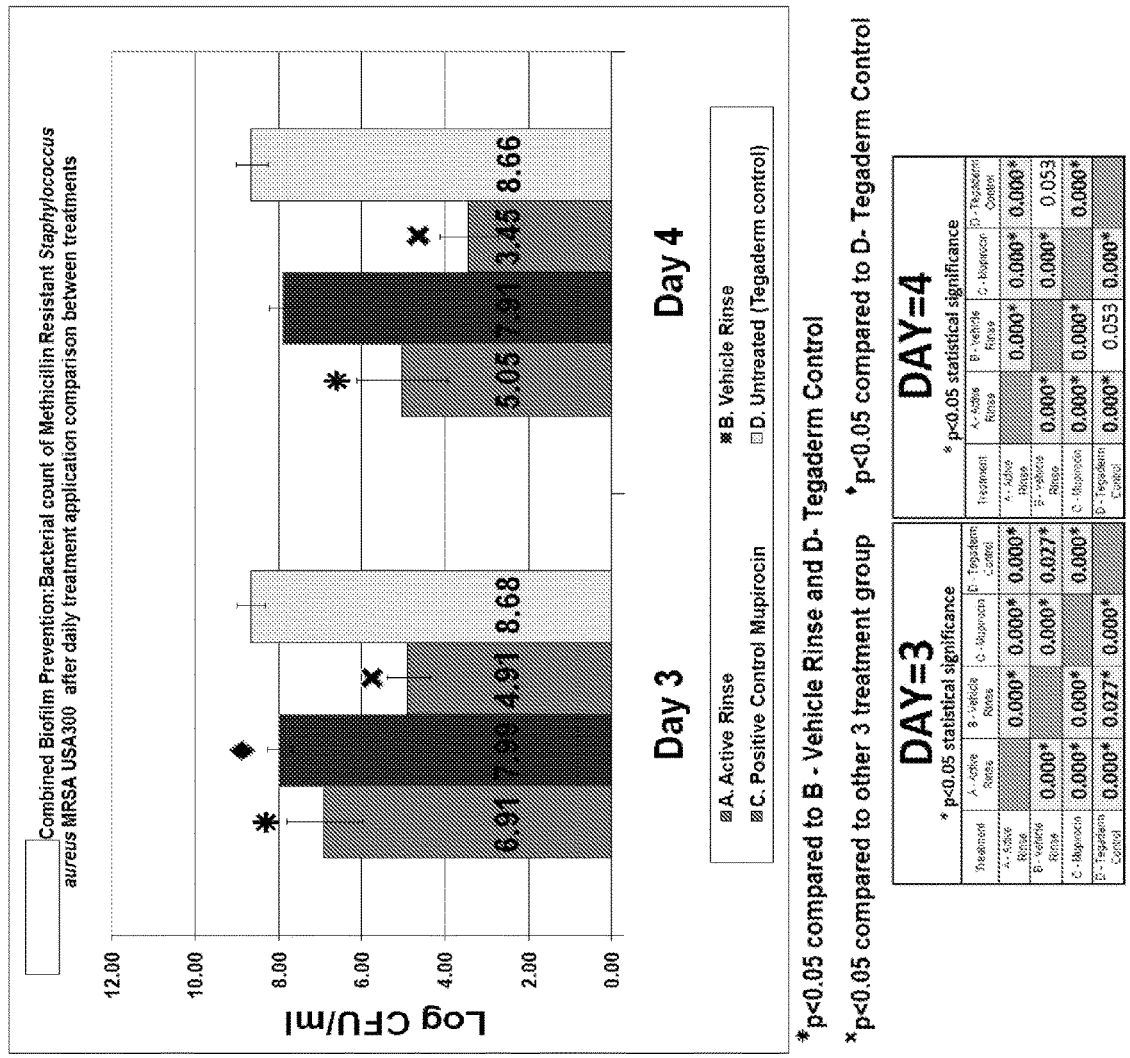

FIG. 24 Bacterial count of MRSA after daily treatment assessed on Days 3 and 4 after PAAG treatment.

Figure 25:
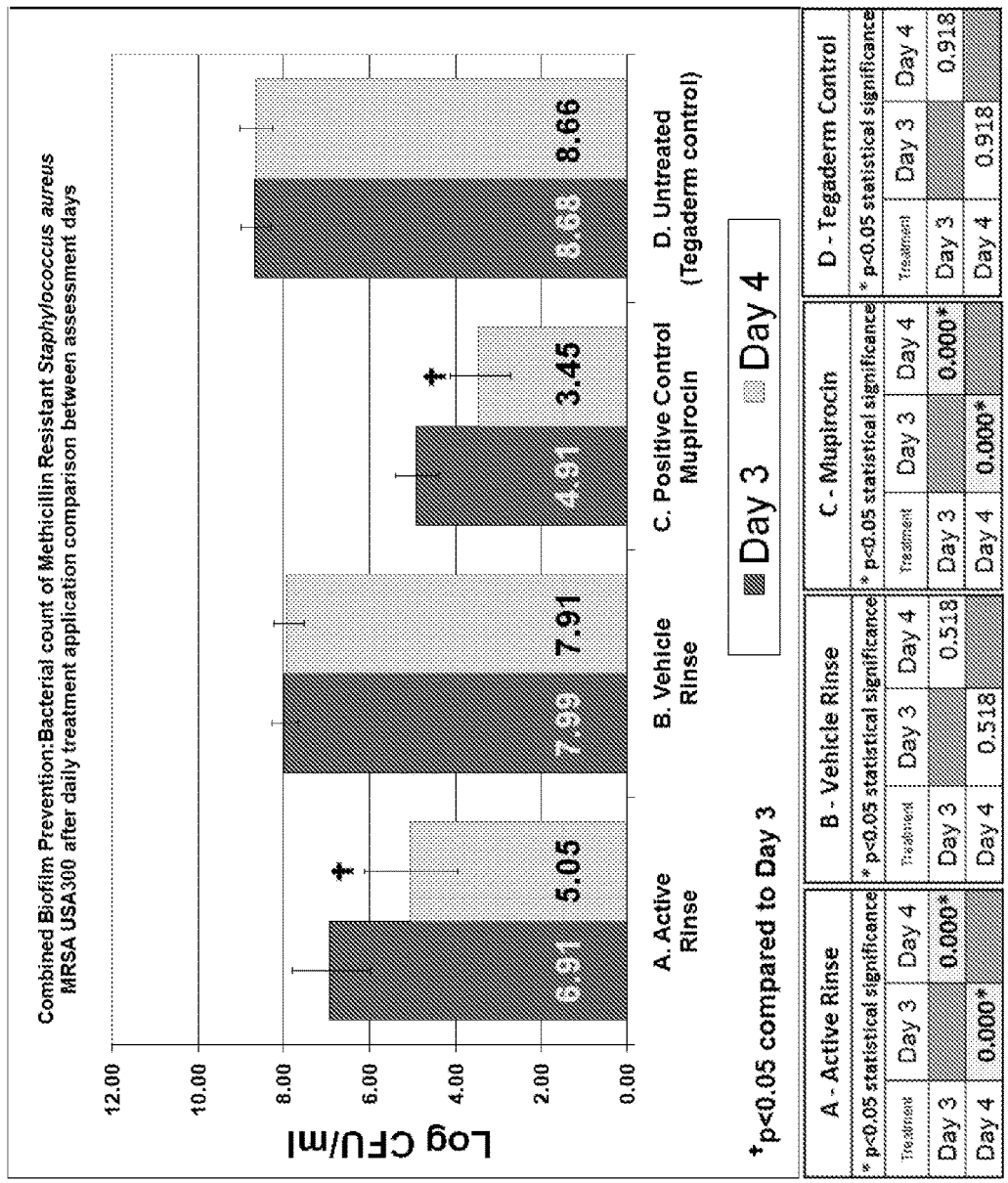

FIG. 25 Comparison of PAAG treated and untreated wounds infected with MRSA across treatment days.

Figure 26:
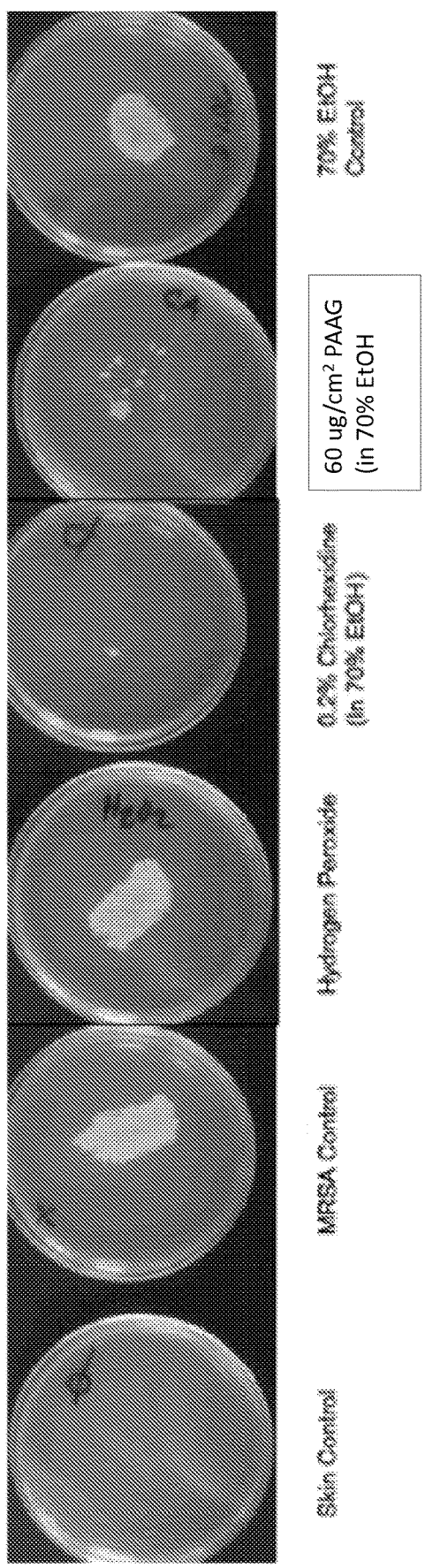

FIG. 26 Residual bactericidal activity of PAAG on pig skin.

FIG. 27 IL-10 concentration (left) and TNF-α (right) concentration in THP-1 human monocyte cells after treatment with PAAG.

Figure 28:
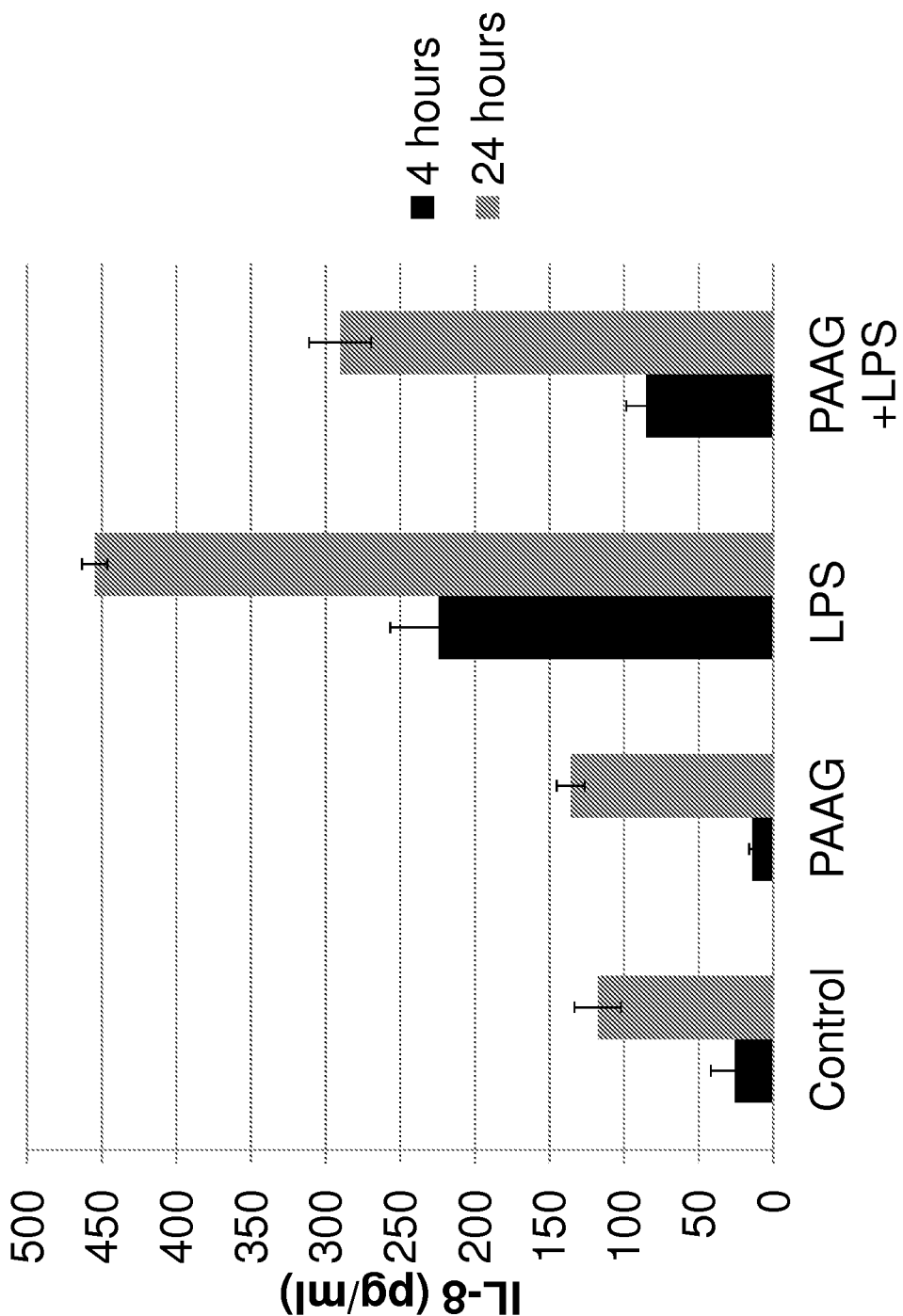
Figure 29:
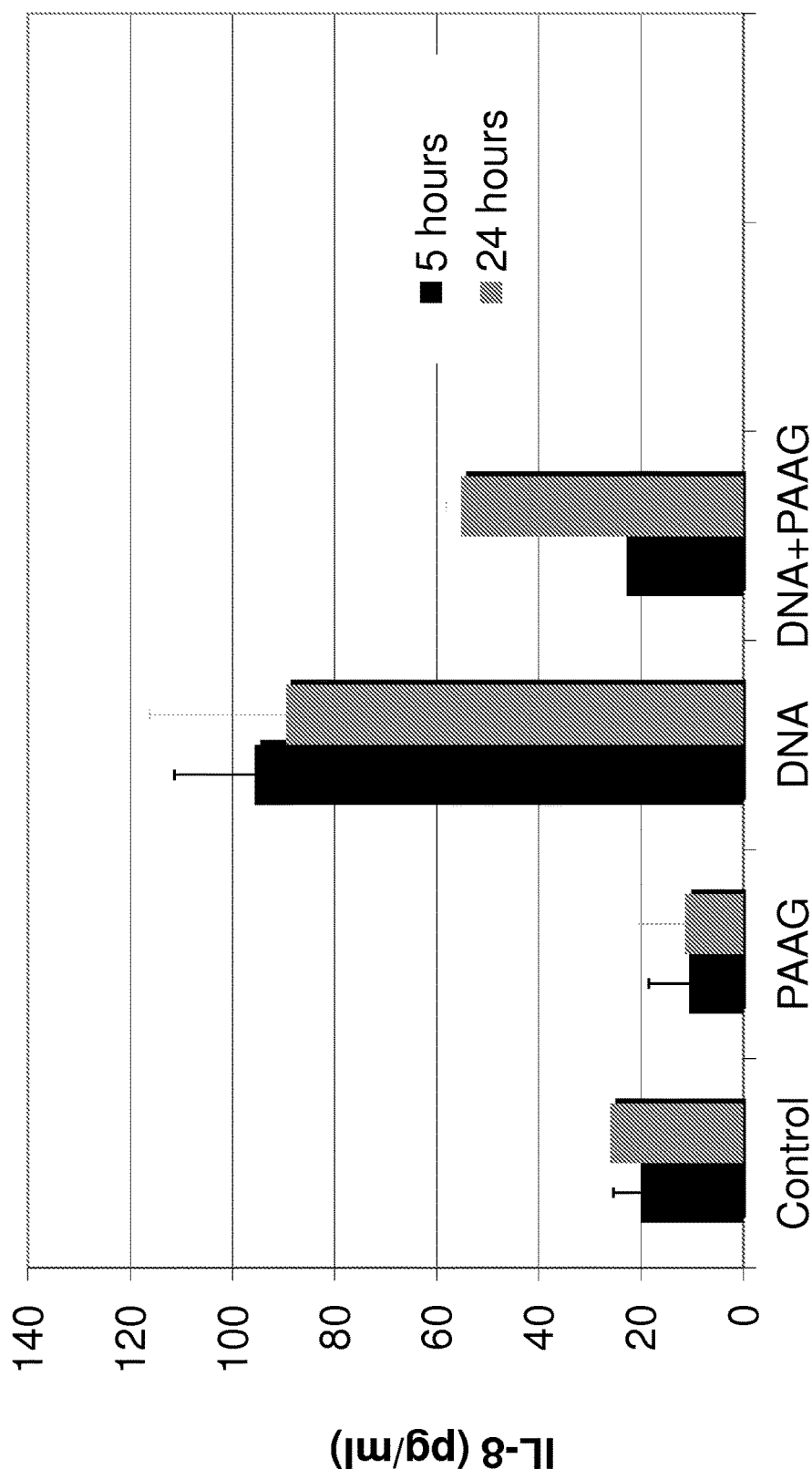
Figure 30:
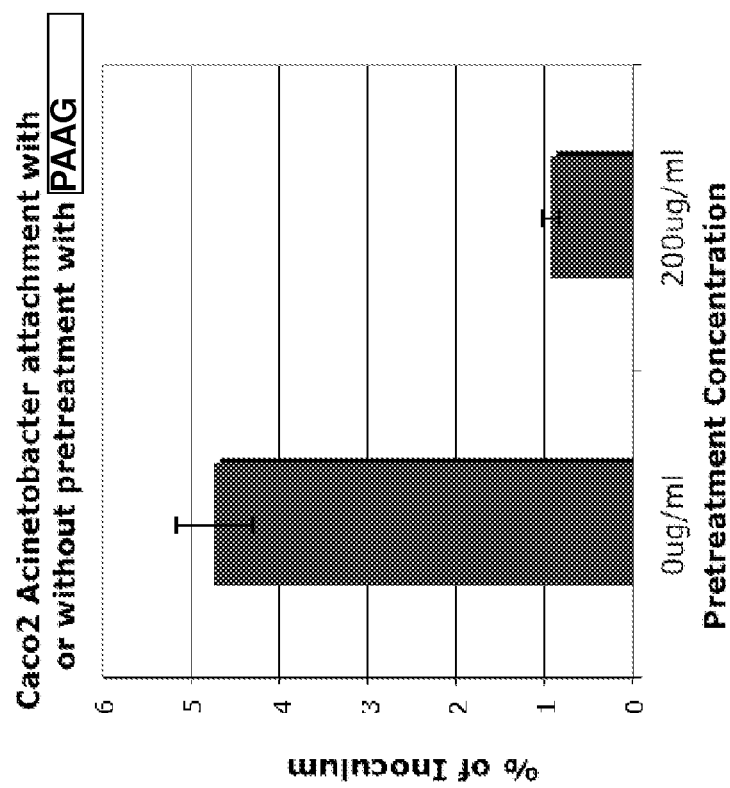

FIG. 28 U937 human macrophage assay measuring LPS stimulated IL-8 production with and without treatment with PAAG FIG. 29 U937 human macrophage assay measuring MRSA DNA stimulated IL-8 production with and without treatment with PAAG FIG. 30 Percent of inoculum of *A. baumannii* attaching to cells after 0 or 200 µg/ml pretreatment with PAAG.

Figure 31:
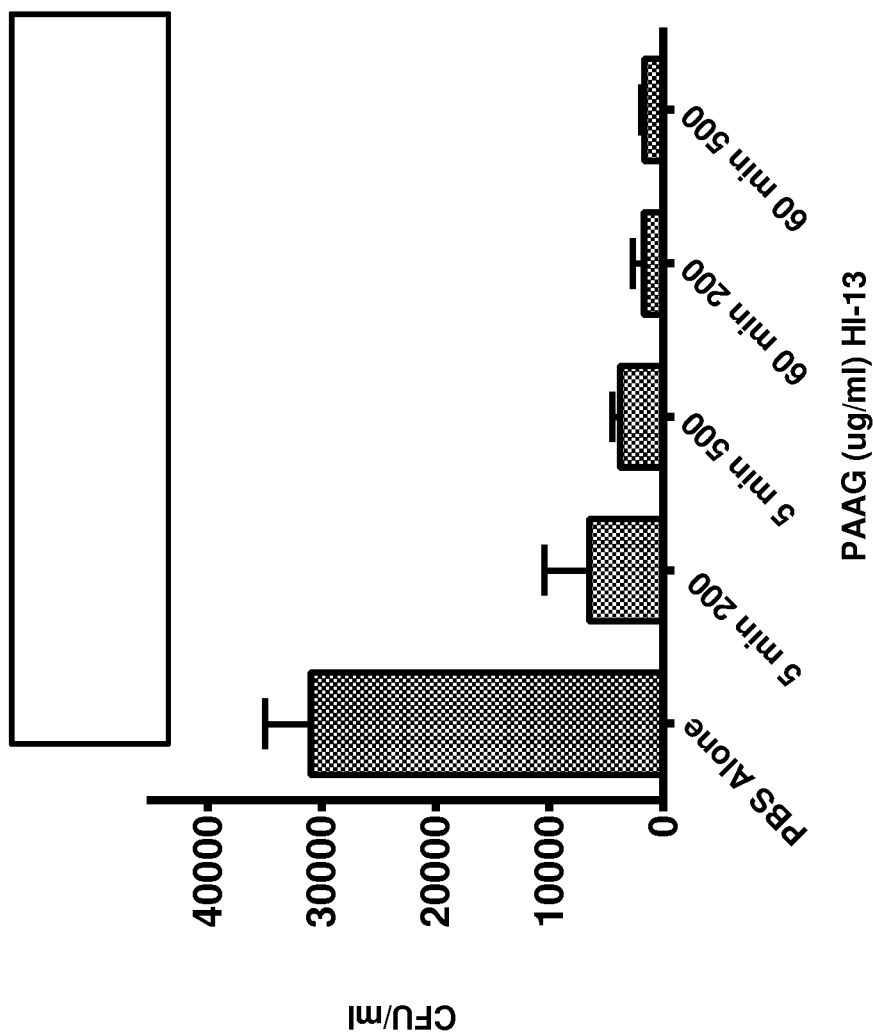

FIG. 31 PAAG in PBS reduced MRSA attachment to nasal Epithelial cells.

Figure 32:
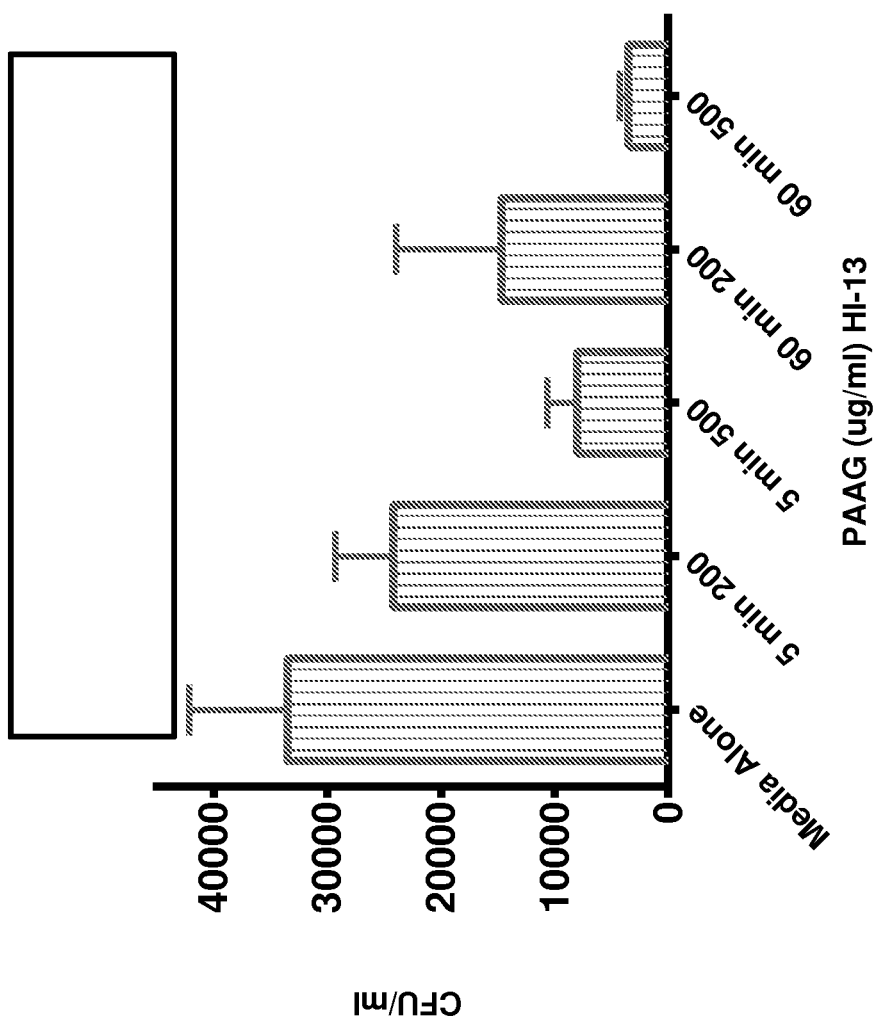

FIG. 32 PAAG in media reduced MRSA attachment to nasal Epithelial cells.

Figure 33:
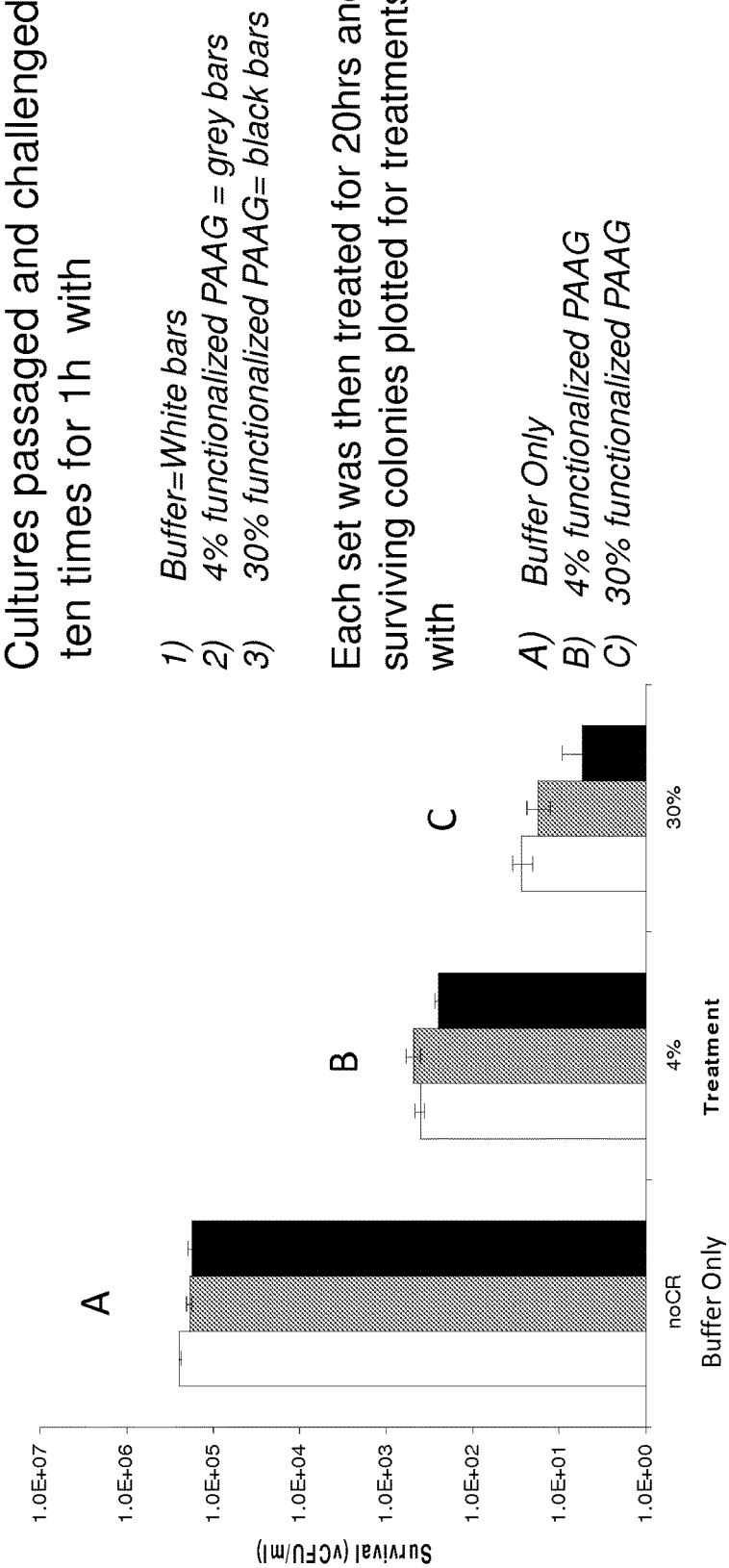

FIG. 33 PAAG does not reduce susceptibility following repeated exposure.

DETAILED DESCRIPTION OF THE INVENTION

The present invention provides methods of treating a wound, e.g., a topical wound, e.g., a wound of the skin, in a subject, wherein the method comprises topically administering to the wound an aqueous composition comprising a polyglucosamine or a derivatized polyglucosamine such as PAAG, to thereby treat the wound in the subject, e.g., a human subject. In some embodiments, the present invention provides methods of treating the wound with an aqueous composition of PAAG at specified concentrations, e.g, at a concentration of about 50 to about 1000 µg/mL (or ppm) (e.g., from about 100 to about 800 µg/mL (or ppm), about 100 to about 600 µg/mL (or ppm)). In some embodiments, the concentration is about 50 µg/mL (or ppm) to about 400 µg/mL (or ppm), about 100 µg/mL (or ppm) to about 300 µg/mL (or ppm), e.g., about 150 µg/mL (or ppm) to about 250 µg/mL (or ppm), e.g., about 200 µg/mL (or ppm). In some embodiments, the concentration is about 200 µg/mL (or ppm). In some embodiments, the concentration is about 300 µg/mL (or ppm) to about 800 µg/mL (or ppm), about 350 µg/mL (or ppm) to about 750 µg/mL (or ppm), about 400 µg/mL (or ppm) to about 700 µg/mL (or ppm), about 450 µg/mL (or ppm) to about 650 µg/mL (or ppm), e.g., about 500 µg/mL (or ppm). In some embodiments, the concentration is about 500 µg/mL (or ppm).

In another aspect, the present invention provides methods of treating an infected wound, e.g., a topical wound, e.g., an infected wound of the skin with a higher concentration of PAAG. In some embodiments, the higher concentration is about 300 µg/mL (or ppm) to about 800 µg/mL (or ppm), about 350 µg/mL (or ppm) to about 750 µg/mL (or ppm), about 400 µg/mL (or ppm) to about 700 µg/mL (or ppm), about 450 µg/mL (or ppm) to about 650 µg/mL (or ppm), e.g., about 500 µg/mL (or ppm). In some embodiments, the concentration is about 500 µg/mL (or ppm).

In some embodiments, the infected wound is a chronic wound. In some embodiments, the infected wound is an acute wound.

In another aspect, the present invention provides methods of treating a non-infected wound, e.g., a topical wound, e.g., a non-infected wound of the skin with a lower concentration of PAAG. In some embodiments, the concentration is about 50 µg/mL (or ppm) to about 400 µg/mL (or ppm), about 100 µg/mL (or ppm) to about 300 µg/mL (or ppm), e.g., about 150 µg/mL (or ppm) to about 250 µg/mL (or ppm), e.g., about 200 µg/mL (or ppm). In some embodiments, the concentration is about 200 µg/mL (or ppm) of PAAG. In some embodiments, the non-infected wound is a chronic wound. In some embodiments, the non-infected wound is an acute wound.

In some embodiments, the polyglucosamine or derivatized polyglucosamine can be one of the following:
(A) Polyglucosamine-arginine compounds;
(B) Polyglucosamine-natural amino acid derivative compounds;
(C) Polyglucosamine-unnatural amino acid compounds;
(D) Polyglucosamine-acid amine compounds;
(E) Polyglucosamine-guanidine compounds; and
(F) Neutral polyglucosamine derivative compounds.

Treatment

The compositions and compounds described herein (e.g., compounds and compositions comprising a water soluble polyglucosamine or a derivatized polyglucosamine such as PAAG) can be administered to a tissue or to a subject to treat a variety of wounds, burns, or disorders, including those described herein below. Wounds can be infected (e.g., by bacteria species (e.g., a bacterial species as described herein), acute infected wounds, chronic infected wounds) or non-infected (e.g., acute non-infected wounds, chronic non-infected wounds). For example, the compounds can be administered, e.g., topically (e.g., by solution (e.g., spray or rinse)). In some embodiments, an aqueous composition comprising PAAG, e.g., a composition described herein is topically applied to a wound of a subject described herein, e.g., a human, large animal such as an elephant, rhinoceros, or tapir, or domesticated animal or pet (e.g., horse, dog, cow, sheep, or cat).

As used herein, the term "treat" or "treatment" is defined as the application or administration of a composition or compound (e.g., a compound described herein (e.g., a soluble or derivatized polyglucosamine) to a subject, e.g., a subject, or application or administration of the composition or compound to an isolated tissue, from a subject, e.g., a subject, who has a wound or disorder (e.g., a wound or disorder as described herein), a symptom of a disorder, or a predisposition toward a disorder, with the purpose to cure, heal, alleviate, relieve, alter, remedy, ameliorate, improve or affect the wound or disorder, one or more symptoms of the disorder or the predisposition toward the disorder (e.g., to prevent at least one symptom of the disorder or to delay onset of at least one symptom of the disorder), and/or a side or adverse effect of a therapy.

As used herein, an amount of a composition or compound effective to treat a disorder, or a "therapeutically effective amount" refers to an amount of the composition or compound which is effective, upon single or multiple dose administration to a subject, in treating a tissue, or in curing, alleviating, relieving or improving a subject with a disorder beyond that expected in the absence of such treatment.

Administration of Compositions

Described herein is topical administration of the pharmaceutical compositions of this invention when the desired treatment involves areas or organs readily accessible by topical application, e.g., the skin, foot pad, nail. Pharmaceutical compositions of this invention include a topical rinse, gel, dry powder, aerosolized liquid, an aerosolized powder, spray, e.g., using a clean application aid, e.g., spray bottle, syringe. In some embodiments, the pharmaceutical compositions of this invention is administered to (e.g., rinses, coats, irrigates, administered by negative pressure therapy to, applied to) the wound. In some embodiments, topical administration is using a spray bottle or syringe, e.g., at a pressure around 4 to around 15 psi.

For application topically to the skin, the pharmaceutical composition is optionally formulated with a suitable ointment containing the active components suspended or dissolved in a carrier. Carriers for topical administration of the compounds of this invention include, but are not limited to, water, an alcohol (e.g., cetearyl alcohol, 2-octyldodecanol, benzyl alcohol), an inert polymer (e.g., an inert polymer present in the composition at an amount of about 0.1% to about 25% w/v, at an amount of about 0.2% to about 10% w/v, most preferably at an amount of about 0.5% to about 5% w/v).

Inert polymers include polyvinylpyrrolidone (PVP) and cross-linked PVP (cross-povidones); neutral polysaccharides (for example, dextran, methyl cellulose and hydroxypropyl methylcellulose (HPMC) (e.g., HPMC of 120 kDa)); linear polyacrylic acid polymers including polymethacrylic acid polymers; cross-linked polyacrylic acid polymers (carbomers); and high molecular weight linear and bridged organic alcohols (for example, linear polyvinyl alcohol).

Alternatively, the pharmaceutical composition can be formulated with a suitable lotion or cream containing the active compound suspended or dissolved in a carrier with suitable emulsifying agents. In some embodiments, the carrier for topical administration of the compounds of this invention is a non-anionic agent. In some embodiments, the pharmaceutical composition comprises a combination of PAAG and a disinfectant and/or antibiotic as disclosed herein.

Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating veterinarian.

Upon improvement of a subject's condition, a maintenance dose of a composition or combination of this invention may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long term basis upon any recurrence of disease symptoms.

In some embodiments, the frequency of administration is once daily. In some embodiments, the frequency of administration is once or twice daily. In some embodiments, the subject is treated for 1, 3, 5, 7, 11, 14, 17, or 20 weeks. In a preferred embodiment, the subject is treated for about 1 week. In some preferred embodiments, the subject is treated for about 1 to about 2 weeks. In some preferred embodiments, the subject is treated for about 2 to about 5 weeks.

Negative Pressure Wound Therapy

Negative pressure wound therapy (NPWT), also known as topical negative pressure, sub-atmospheric pressure dressings or vacuum sealing technique, is a therapeutic technique used to promote healing in acute or chronic wounds, fight infection and enhance healing of burns. A vacuum source is used to create sub-atmospheric pressure in the local wound environment.

NPWT seals the wound to prevent dehiscence with a gauze or foam filler dressing, a drape and a vacuum source that and applies negative pressure to the wound bed with a tube threaded through the dressing. The vacuum may be applied continuously or intermittently, depending on the type of wound being treated and the clinical objectives. Intermittent removal of used instillation fluid supports the cleaning and drainage of the wound bed and the removal of infectious material.

NPWT has two forms which mainly differ in the type of dressing used to transfer NPWT to the wound surface: gauze or foam. For pain sensitive patients with shallow or irregular wounds, wounds with undermining or explored tracts or tunnels, and for facilitating wound healing, gauze may be a better choice for the wound bed, while foam may be cut easily to fit a patient's wound that has a regular contour and perform better when aggressive granulation formation and wound contraction is the desired goal.

A dressing, containing a drainage tube, is fitted to the contours of a deep or irregularly-shaped wound and sealed with a transparent film. The tube is connected to a vacuum source, turning an open wound into a controlled, closed wound while removing excess fluid from the wound bed to enhance circulation and remove waste from the lymphatic system. Fluid or treatments may be circulated to the wound through the foam or dissociated from the foam. The technique can be used with chronic wounds or wounds that are expected to present difficulties while healing (such as those associated with a chronic disease, e.g., diabetes or when the veins and arteries are unable to provide or remove blood adequately).

Compositions Comprising Polyglucosamine or a Derivatized Polyglucosamine

The compositions described herein comprise water soluble polyglucosamine or a derivatized polyglucosamine. In some preferred embodiments, the water soluble polyglucosamine or a derivatized polyglucosamine is poly (acetyl, arginyl) glucosamine or PAAG. In particular, the present invention relates to dried compositions (e.g., lyophilized, spray-dried) and reconstituted compositions.

At neutral pH in solution, PAAG at ambient temperature is very slowly hydrolyzed (e.g. <10% loss of molecular weight in 4 months). PAAG is slightly hygroscopic, therefore a dried composition of PAAG extends the lifetime (e.g., shelf-life) of PAAG relative to PAAG in solution. A dried composition of PAAG is more resistant to hydrolysis than PAAG in solution.

Dried Compositions

The compositions described herein may be present in a dry composition, e.g., a vacuum dried, lyophilized composition or a spray dried composition.

Lyophilization, the technical name for a process often referred to as "freeze-drying" comprising freezing an aqueous mixture or suspension into a frozen solid, then generally subjecting the frozen solid to a vacuum for a substantial period of time. The vacuum causes the water molecules to sublimate. The methods described herein include the step of lyophilizing the active ingredient (e.g., PAAG). In one embodiment, lyophilization occurs after sterilization (e.g., heat sterilization, filtration). In one embodiment, sterilization occurs after lyophilization (e.g., irradiation). In one embodiment, sterilization occurs before and after lyophilization. In one embodiment, the lyophilized product is not sterilized.

In one embodiment, during the lyophilization process, the solvent system used (e.g., sterile water) is substantially removed by sublimation. In another embodiment, less than about 5% residual solvent remains after lyophilization. In another embodiment, less than about 3% residual solvent remains after lyophilization. In another embodiment, less than about 2% residual solvent remains after lyophilization. In another embodiment, less than about 1% residual solvent remains after lyophilization. In another embodiment, less than about 0.1% residual solvent remains after lyophilization.

In some embodiments, the lyophilization process provides a composition comprising an active compound (e.g., PAAG) that can be stored at room temperature for extended periods of time.

Lyophilized forms of compositions described herein provide for a substantially more stable form, which, when needed, can be reconstituted in an acceptable solvent system (e.g., sterile water). The embodiments described herein provide a reconstituted form within a relatively short period of time (e.g., 20 seconds shaking a vial containing the lyophile formulation and acceptable solvent). Such stable forms as described herein are, in other embodiments, stable at various temperatures for extended periods of time.

Spray drying is a method of producing a dry powder from a liquid or slurry by rapidly drying with a hot gas (e.g., air, nitrogen). Spray dryers use some type of atomizer or spray nozzle to disperse the liquid or slurry into a controlled drop size spray. The most common of these are rotary disks and single-fluid high pressure swirl nozzles. Alternatively, for some applications, two-fluid or ultrasonic nozzles are used. With most common spray dryers, called single effect, gas (e.g., air, nitrogen) is blown in co-current of the sprayed liquid. Conventional spray drying provides fine particles of powder, which may clump together when dissolved or dispersed in liquids. Spray dried particles may be less than 150 μm in diameter.

Methods for preparation of lyophilized compositions are known in the art. In one aspect, the method of preparation is vacuum-drying. In an embodiment, the method of preparation is vacuum evaporation (e.g., using a flat evaporator, rotating evaporator, bed evaporator, vacuum oven).

In one aspect, the method of preparation is freeze drying (e.g., lyophilization).

In another aspect, the method of preparation is spray drying.

In some embodiments, the method of preparation yields a powder of the active ingredient plus any additional desired ingredient from a previously sterile-filtered solution thereof. In a preferred embodiment, the method of preparation yields a powder of the active ingredient substantially free of impurities.

Reconstituted Compositions

The dried compositions of the water soluble polyglucosamine or a derivatized polyglucosamine composition such as PAAG can be reconstituted as needed with a suitable diluent (e.g., sterile water). A reconstituted composition is a resolubilized dry composition comprising the water soluble polyglucosamine or a derivatized polyglucosamine such as PAAG to a desired concentration.

In some embodiments, the lyophilized compositions described herein readily reconstitute once contacted with a sufficient amount of a pharmaceutically acceptable carrier. For example, in some embodiments, the lyophilized composition is mixed in the vial it is contained in, e.g., shaken for about 1 to about 3 minutes, with a pharmaceutically acceptable carrier, e.g., sterile water, to provide a reconstituted composition suitable for topical administration (e.g., surface spray). In one embodiment, the lyophilized composition is reconstituted in a relatively short period of time, e.g., less than 1 minute, less than 30 seconds, and in other embodiments, about 20 seconds. In certain embodiments, the lyophilized compositions reconstitute in a time of less than 2 minutes. These short reconstitution times provide an advantage in that the therapeutic agent has not decomposed from exposure in a solution for an extended period of time prior to administration. In one embodiment, the reconstituted composition is suitable for topical administration (e.g., surface spray or rinse). In another embodiment, the reconstituted form is a non-suspension. In a further embodiment, the reconstituted form is a clear solution and remains substantially clear prior to administration.

A feature of the subject matter described herein is a dried (e.g., lyophilized, spray-dried) composition (e.g., comprising PAAG) that is formulated substantially free of impurities (e.g., surfactants) and that is amenable to full reconstitution with a carrier or diluents in a short period of time.

In some embodiments, the reconstituted composition is around 100 μg/mL (or ppm) to around 1000 μg/mL (or ppm) PAAG. In some embodiments, the reconstituted composition is around 500 μg/mL (or ppm) PAAG. In some embodiments, the reconstituted composition is around 200 μg/mL (or ppm) PAAG.

Suitable diluents include biocompatible media, e.g., sterile water, buffered aqueous media, saline, buffered saline, optionally buffered solutions of sugars, optionally buffered solutions of vitamins, optionally buffered solutions of synthetic polymers, and osmotically balanced solutions containing non-ionic osmols. In a preferred embodiment, the diluent is sterile water.

The lyophilized composition may be reconstituted to produce a composition that has a desired therapeutic concentration. In a preferred embodiment, the concentration of the PAAG in the final liquid composition is around 100 to around 700 μg/mL (or ppm). In a preferred embodiment, the concentration of the PAAG in the final liquid concentration is around 500 μg/mL (or ppm). In another preferred embodiment, the concentration of the PAAG in the final liquid composition is 200 μg/mL (or ppm).

In a preferred embodiment, the composition comprises water (e.g., sterile water) and PAAG. In some embodiments, the composition also comprises a disinfectant and/or antibiotic. Exemplary disinfectants include chlorhexidine or betadine. Exemplary antibiotics include silver containing compounds (e.g., nanoparticle silver or ionic silver), hydrogen peroxide or a hydrogen peroxide source (e.g., honey-based products containing glucose oxidase), or iodine products (e.g., betadine). In some embodiments, the composition is substantially free of components other than a diluent (e.g., water e.g., sterilized water) and PAAG.

In a preferred embodiment, the composition comprises water (e.g., sterile water) and PAAG at around 10 to around 1000 μg/mL (or ppm). In an embodiment, the composition comprises PAAG at around 500 μg/mL (or ppm). In an embodiment, the composition comprises PAAG at around 200 μg/mL (or ppm).

In accordance with aspects of the invention, dried composition (e.g., lyophilized, spray-dried, agglomerated powder) is added to water. There should be enough water to completely dissolve the powder. In some embodiments, the concentration of the PAAG in the final liquid composition is around 100 to around 700 μg/mL (or ppm). In a preferred embodiment, the concentration of the PAAG in the final liquid concentration is around 500 μg/mL (or ppm). In another preferred embodiment, the concentration of the PAAG in the final liquid composition is 200 μg/mL (or ppm).

Subjects

The subject can be a human or a non-human animal. Suitable human subjects includes, e.g., a human patient having a wound, e.g., a wound described herein or a normal subject. The term "non-human animals" of the invention includes all vertebrates, e.g., non-mammals (such as chickens, amphibians, reptiles) and mammals, such as non-human primates, e.g., elephant, sheep, dog, cat, cow, pig, etc. Suitable animal subjects include: but are not limited to, wild animals, farm animals, zoo animals, circus animals, companion (pet) animals, domesticated and/or agriculturally useful animals. Suitable animal subjects include primates, rodents, and birds. Examples of said animals include, but not limited to, rhinoceros, elephants, tapirs, guinea pigs, hamsters, gerbils, rat, mice, rabbits, dogs, cats, horses, pigs, sheep, cows, goats, deer, rhesus monkeys, monkeys, tamarinds, apes, baboons, gorillas, chimpanzees, orangutans, gibbons, fowl, e.g., pheasant, quail (or other gamebirds), a waterfowl, ostriches, chickens, turkeys, ducks, and geese or free flying bird.

In some preferred embodiments, the subject is a human. In other preferred embodiments, the subject is an elephant, rhinoceros, or tapir. In other preferred embodiments, the subject is a dog, cat, horse, pig or other domesticated or companion animal.

Wound

As used herein, a wound refers to a type of injury which damages a part or tissue of the body, for example, skin (e.g., epidermis, dermis, and hypodermis) and/or underlying tissue, mucous membrane (e.g., oral mucous membrane), or other epithelia (e.g., corneal epithelium).

Wounds can be classified as open wounds. Wounds can also be classified as chronic or acute wounds. Wounds can be non-healing wounds. Wounds can be infected wounds.

An open wound refers to a type of injury in which a tissue, e.g., skin or mucous membrane, is torn, cut or punctured. Open wounds can be further classified according to the object that caused the wound. The types of open wound include, e.g., incisions or incised wounds, caused by a clean, sharp-edged object such as a knife, a razor or a glass splinter; lacerations, which are irregular tear-like wounds caused by some blunt trauma; abrasions (grazes), which are superficial wounds in which the topmost layer of the skin (the epidermis) is scraped off, often caused by a sliding fall onto a rough surface; puncture wounds, caused by an object puncturing the skin or mucous membrane, such as a nail or needle; penetration wounds, caused by an object such as a knife entering and coming out from the skin or mucous membrane; gunshot wounds (e.g., one at the site of entry and one at the site of exit), caused by a bullet or similar projectile driving into or through the body.

A closed wound refers to a type of injury without broken of the tissue (e.g., skin or mucous membrane), e.g., caused by a blunt force trauma. The types of closed wounds include, e.g., contusions or bruises, caused by a blunt force trauma that damages tissue under the skin or mucous membrane; hematomas or blood tumor, caused by damage to a blood vessel that in turn causes blood to collect under the skin or mucous membrane; crush injury, caused by a great or extreme amount of force applied over a long period of time; acute or traumatic wounds, which are the result of injuries that disrupt the tissue; and chronic wounds (e.g., pressure, venous, oral, peptic, or diabetic ulcers), caused by a relatively slow process that leads to tissue damage, often when an insufficiency in the circulation or other systemic support of the tissue causes it to fail and disintegrate. Infection can then take hold of the wound site and becomes a chronic abscess. Once the infection hits a critical point, it can spread locally or become systemic (sepsis).

Wound healing, or wound repair, refers to an intricate process in which the tissue, e.g., skin or mucous membrane, repairs itself after injury. In normal skin, the epidermis and dermis exist in a steady-state equilibrium, forming a protective barrier against the external environment. Once the protective barrier is broken, the physiologic process of wound healing is immediately set in motion. The wound healing process is restricted and slowed by bacterial infection or by local acute or chronic inflammation.

Chronic Wound

A chronic wound is a wound that does not heal in a orderly and/or predictable amount of time (e.g., within three months). Chronic wounds may never heal or take years to heal.

In a preferred embodiment, the wound comprises a chronic non-healing wound, e.g., a chronic foot disease, e.g., cracked nails, abscesses, lesions, ulcers, fissures, and/or chronic non-healing dermal or a subdermal wound, e.g., an abscess or pressure sore. In some aspects of these embodiments, the wound is infected. In some other aspects of these embodiments, the wound is not infected.

As used herein, a chronic disease refers to a disease in which the symptom of the disease includes at least one wound. The chronic diseases described herein can be the result of infection, e.g., bacterial infection, and the infection might no longer be present when the chronic disease or wound is treated. The symptoms of chronic diseases can sometimes be less severe than those of the acute phase of the same disease, but persist over a long period. Chronic diseases may be progressive, result in complete or partial disability, or even lead to death.

Examples of chronic diseases that can be associated with poor or slow wound healing include a wound caused by chronic inflammation or bacterial species (e.g., an aerobic or facultative anaerobic gram positive and/or gram negative bacteria, sensitive and drug resistant bacteria, e.g., multidrug resistant forms). Examples include chronic foot disease, e.g., cracked nails, abscesses, lesions, ulcers, fissures or chronic non-healing or dermal or subdermal wounds, e.g., abscesses, pressure sores, impacted temporal glands.

Acute Wound

An acute wound is a wound wherein there is a balance between the production and degradation of molecules such as collagen (e.g., not substantially more degradation than production). In some aspects of these embodiments, the wound is infected. In some other aspects of these embodiments, the wound is not infected.

In some preferred embodiments, the wound comprises an acute wound, e.g., incisions or incised wounds, caused by a clean, sharp-edged object such as a knife, a razor or a glass splinter; lacerations, which are irregular tear-like wounds caused by some blunt trauma; abrasions (grazes), which are superficial wounds in which the topmost layer of the skin (the epidermis) is scraped off, often caused by a sliding fall onto a rough surface; puncture wounds, caused by an object puncturing the skin or mucous membrane, such as a nail or needle; penetration wounds, caused by an object such as a knife entering and coming out from the skin or mucous membrane; gunshot wounds (e.g., one at the site of entry and one at the site of exit), caused by a bullet or similar projectile driving into or through the body. In some aspects of these embodiments, the wound is infected.

Examples of acute wounds that can be associated with poor or slow wound healing include a wound caused by inflammation or bacterial species (e.g., an aerobic or facultative anaerobic gram positive and/or gram negative bacteria, sensitive and drug resistant bacteria, e.g., multi-drug resistant forms).

Burn

A burn refers to a type of skin injury caused by heat, electricity, chemicals, light, radiation, or friction. Burns can affect the skin (epidermal tissue and dermis) and/or deeper tissues, such as muscle, bone, and blood vessels. Burn injuries can be complicated by shock, infection, multiple organ dysfunction syndrome, electrolyte imbalance and respiratory distress.

Burns can be classified as first-, second-, third-, or fourth-degree. First-degree burns can involve only the epidermis and be limited to redness (erythema), a white plaque and minor pain at the site of injury. For example, most sunburns are included as first-degree burns. Second-degree burns manifest as erythema with superficial blistering of the skin, and can involve more or less pain depending on the level of nerve involvement. Second-degree burns involve the superficial (papillary) dermis and may also involve the deep (reticular) dermis layer. Third-degree burns occur when the epidermis is lost with damage to the subcutaneous tissue. Burn victims will exhibit charring and severe damage of the epidermis, and sometimes hard eschar will be present. Third-degree burns result in scarring and victims will also exhibit the loss of hair shafts and keratin. Fourth-degree burns can damage muscle, tendon, and ligament tissue, thus result in charring and catastrophic damage of the hypodermis. In some instances the hypodermis tissue may be partially or completely burned away as well as this may result in a condition called compartment syndrome.

The burn depths are described as superficial, superficial partial-thickness, deep partial-thickness, or full-thickness.

Burns can also be assessed in terms of total body surface area (TBSA), which is the percentage affected by partial thickness or full thickness burns (erythema/superficial thickness burns are not counted). The rule of nines can be used as a quick and useful way to estimate the affected TBSA. More accurate estimation can be made using Lund & Browder charts which take into account the different proportions of body parts in adults and children.

Burns can be caused by a number of substances and external sources such as exposure to chemicals (e.g., strong acids or bases, caustic chemical compounds), friction, electricity (e.g., workplace injuries, being defibrillated or cardioverted without a conductive gel, lightening), radiation (e.g., protracted exposure to UV light, tanning booth, radiation therapy, sunlamps, X-rays) and heat (e.g., scalding).

The treatments of burns include, e.g., stopping the burning process at the source, cooling the burn wound, intravenous fluids, debridement (removing devitalized tissue and contamination), cleaning, dressing (e.g., biosynthetic dressing), pain management (e.g., analgesics (e.g., ibuprofen, acetaminophen), narcotics, local anesthetics), hyperbaric oxygenation, surgical management, control of infection, control of hyper-metabolic response.

Guidance for the determination of the dosage that delivers a therapeutically effective amount of the composition described herein to treat burns may be obtained from animal models of burns, e.g. as described in Santos Heredero F X et al., *Annals of Burns and Fire Disasters*, IX-n. 2 (June 1996); and Stevenson J M et al., *Methods Mol Med.* 2003; 78:95-105.

Chronic Diseases

As used herein, a chronic disease refers to a disease in which the symptom of the disease includes at least one wound. The chronic diseases described herein can be the result of infection, e.g., bacterial infection, and the infection might no longer be present when the chronic disease or wound is treated. The symptoms of chronic diseases can sometimes be less severe than those of the acute phase of the same disease, but persist over a long period. Chronic diseases may be progressive, result in complete or partial disability, or even lead to death.

Secondary Wound Therapy

In an embodiment, the method further comprises administering to the subject a second wound therapy, e.g., antibiotic or antibacterial use, debridement, irrigation, negative pressure wound therapy (vacuum-assisted closure), warming, oxygenation, moist wound healing, removing mechanical stress, and/or adding cells (e.g., keratinocytes) or other materials (e.g., artificial skin substitutes that have fibroblasts and/or keratinocytes in a matrix of collagen) to secrete or enhance levels of healing factors (e.g., vascular endothelial growth factor (VEGF), insulin-like growth factor (IGF), platelet-derived growth factor (PDGF), transforming growth factor-β (TGF-β), and epidermal growth factor (EGF)).

In an embodiment, the second wound therapy comprises a negative pressure wound therapy (vacuum-assisted closure).

In an embodiment, the second wound therapy comprises an antibiotic. In an embodiment, the composition overcomes (e.g., reduces, decreases, prevents) a deleterious effect of the antibiotic in wound healing.

In an embodiment, the second wound therapy comprises a steroidal or non-steroidal anti-inflammatory drug (NSAID). In an embodiment, the composition acts additively or synergistically with the steroidal or non-steroidal anti-inflammatory drug. In an embodiment, the composition is administered topically or orally, e.g., by topical rinse, gel, spray, oral, enema, inhalation, dry powder, aerosolized liquid, aerosolized powder, or eye drop. In some embodiments, the composition is administered orally to treat a wound (e.g., damaged mucosa) in the gastrointestinal tract and/or an inflammatory gastrointestinal disorder. In some embodiments, the composition is administered topically to treat a wound and/or reduce or prevent a scar, e.g., in the eye.

Compounds

Soluble Polyglucosamines and Polyglucosamines Derivatives

Compounds and compositions (e.g., vacuum-dried, lyophilized, spray-dried, reconstituted) containing a soluble polyglucosamine or a derivatized polyglucosamine such as PAAG for treating wounds in a subject (e.g., a subject as described herein) are described herein.

Polyglucosamines can be derived from chitin or chitosan. Chitosan is an insoluble polymer derived from the deacetylation of chitin, which is a polymer of N-acetylglucosamine, that is the main component of the exoskeletons of crustaceans (e.g., shrimp, crab, lobster). Chitosan is generally a β(1→4)polyglucosamine that is less than 50% acetylated while chitin is generally considered to be more than 50% acetylated. Polyglucosamines are also found in various fungi and arthropods. Synthetic sources and alternate sources of β(1→4)polyglucosamines may serve as the starting material for polyglucosamine derivatives. Polyglucosamines, as opposed to polyacetylglucosamines, are defined herein to be less than 50% acetylated. If greater than 50% of the amino groups are acetylated, the polymer is considered a polyacetylglucosamine.

A soluble polyglucosamine described herein refers to a neutral pH, water soluble polyglucosamine or polyglucosamine that is not derivatized on the hydroxyl or amine moieties other than with acetyl groups. A soluble polyglucosamine is comprised of glucosamine and acetylglucosamine monomers. Generally, a water soluble polyglucosamine (at neutral pH) has a molecular weight of less than or equal to about 5,000 kDa and a degree of deacetylation equal to or greater than 80%.

A polyglucosamine derivative described herein is generated by functionalizing the free hydroxyl or amine groups with positively charged or neutral moieties. The percent of functionalization is defined as the total percent of monomers on the polyglucosamine backbone that have been functionalized with a positively charged or neutral moiety. The degrees of deacetylation and functionalization impart a specific charge density to the functionalized polyglucosamine derivative. The resulting charge density affects solubility and effectiveness of treatment. Thus, in accordance with the present invention, the degree of deacetylation, the functionalization and the molecular weight must be optimized for optimal efficacy. The polyglucosamine derivatives described herein have a number of properties which are advantageous, including solubility at physiologic (neutral) pH. In some embodiments, the polyglucosamine derivative is soluble up to a pH of 10. In some embodiments, the molecular weight of the polyglucosamine derivative is between 5 and 1,000 kDa. In some embodiments, the molecular weight of the polyglucosamine derivative is between 15 and 1,000 kDa. In some embodiments, the molecular weight of the polyglucosamine derivative is between 20 and 350 kDa. In some embodiments, the molecular weight of the polyglucosamine derivative is between 20 and 150 kDa. In some embodiments, the molecular weight of the polyglucosamine derivative is between 20 and 120 kDa. In some embodiments, the molecular weight of the polyglucosamine derivative is between 30 and 120 kDa. In some embodiments, the molecular weight of the polyglucosamine derivative is between 50 and 100 kDa. In some embodiments, the molecular weight of the polyglucosamine derivative is between 20 and 80 kDa. The polyglucosamine derivative described herein is soluble at pH 2 to pH 11.

Polyglucosamines with any degree of deacetylation (DDA) greater than 50% are used in the present invention, with functionalization between 2% and 50% of the total monomers on the polyglucosamine backbone. The degree of deacetylation determines the relative content of free amino groups to total monomers in the polyglucosamine polymer. Methods that can be used for determination of the degree of deacetylation of polyglucosamine include, e.g., ninhydrin test, linear potentiometric titration, near-infrared spectroscopy, nuclear magnetic resonance spectroscopy, hydrogen bromide titrimetry, infrared spectroscopy, and first derivative UV-spectrophotometry. Preferably, the degree of deacetylation of a soluble polyglucosamine or a derivatized polyglucosamine described herein is determined by quantitative infrared spectroscopy.

Percent functionalization by active derivitization of the amines is determined relative to the total number of monomers on the polyglucosamine polymer. Preferably, the percent functionalization of a derivatized polyglucosamine described herein is determined by H-NMR or quantitative elemental analysis. The degrees of deacetylation and functionalization impart a specific charge density to the functionalized polyglucosamine derivative. The resulting charge density affects solubility, and strength of interaction with tissue, biofilm components and bacterial membranes. The molecular weight is also an important factor in a derivatized polyglucosamine's mucoadhesivity and biofilm disrupting capability. Thus, in accordance with the present invention, these properties must be optimized for optimal efficacy. Exemplary polyglucosamine derivatives are described in U.S. Pat. No. 8,119,780, which is incorporated herein by reference in its entirety.

The polyglucosamine derivatives described herein have a range of polydispersity index (PDI) between about 1.0 to about 2.5. As used herein, the polydispersity index (PDI), is a measure of the distribution of molecular weights in a given polymer sample. The PDI calculated is the weight averaged molecular weight divided by the number averaged molecular weight. This calculation indicates the distribution of individual molecular weights in a batch of polymers. The PDI has a value always greater than 1, but as the polymer chains approach uniform chain length, the PDI approaches unity (1). The PDI of a polymer derived from a natural source depends on the natural source (e.g. chitin or chitosan from crab vs. shrimp vs. fungi) and can be affected by a variety of reaction, production, processing, handling, storage and purifying conditions. Methods to determine the polydispersity include, e.g., gel permeation chromatography (also known as size exclusion chromatography); light scattering measurements; and direct calculation from MALDI or from electrospray mass spectrometry. Preferably, the PDI of a soluble polyglucosamine or a derivatized polyglucosamine described herein is determined by HPLC and multi angle light scattering methods.

The polyglucosamine derivatives (i.e., derivatized polyglucosamines) described herein have a variety of selected molecular weights that are soluble at neutral and physiological pH, and include for the purposes of this invention molecular weights ranging from 5-1,000 kDa. Derivatized polyglucosamines are soluble at pH up to about 10. Embodiments described herein are feature medium range molecular weight of derivatized polyglucosamines (20-150 kDa, e.g., from about 20 to about 150 kDa). In some embodiments, the molecular weight of the derivatized polyglucosamine is between 15 and 1,000 kDa. In some embodiments, the molecular weight of the derivatized polyglucosamine is between 20 and 150 kDa. In some embodiments, the molecular weight of the derivatized polyglucosamine is between 20 and 120 Da. In some embodiments, the molecular weight of the polyglucosamine derivative is between 30 and 120 kDa. In some embodiments, the molecular weight of the polyglucosamine derivative is between 50 and 100 kDa. In some embodiments, the molecular weight of the functionalized polyglucosamine is between 20 and 80 kDa.

The functionalized polyglucosamine derivatives described herein include the following:

(A) Polyglucosamine-arginine compounds;
(B) Polyglucosamine-natural amino acid derivative compounds;
(C) Polyglucosamine-unnatural amino acid compounds;
(D) Polyglucosamine-acid amine compounds;
(E) Polyglucosamine-guanidine compounds; and
(F) Neutral polyglucosamine derivative compounds.

(A) Polyglucosamine-Arginine Compounds

In some embodiments, the present invention is directed to polyglucosamine-arginine compounds, where the arginine is bound through a peptide (amide) bond via its carbonyl to the primary amine on the glucosamines of polyglucosamine:

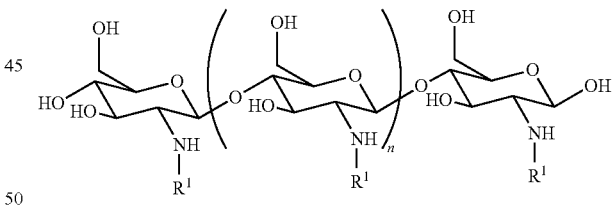

wherein each $R^1$ is independently selected from hydrogen, acetyl, and a group of the following formula:

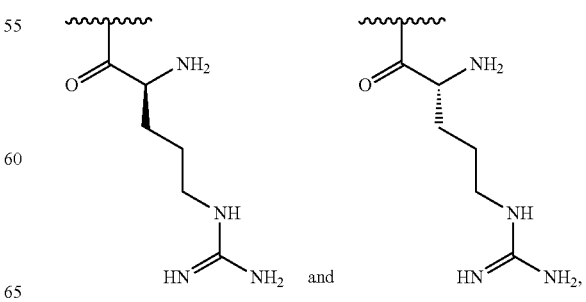

or a racemic mixture thereof, wherein at least 25% of $R^1$ substituents are H, at least 1% are acetyl, and at least 2% are a group of the formula shown above.

In some embodiments, a polyglucosamine-arginine compound is of the following formula

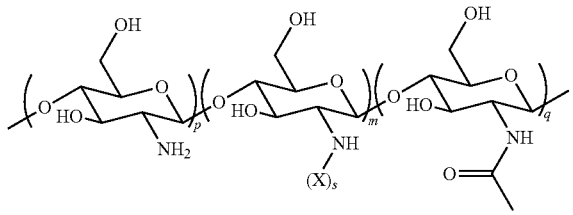

where m is 0.02-0.50; q is 0.50-0.01; s is 1; p+q+m=1; the percent degree of functionalization is m·100%; and X is selected from the group consisting of:

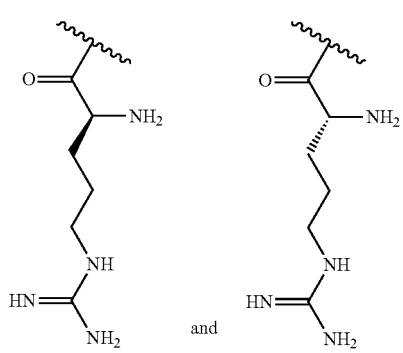

wherein the preparation is substantially free of compounds having a molecular weight of less than 5 kDa.

(B) Polyglucosamine-Natural Amino Acid Derivative Compounds

In some embodiments, the present invention is directed to polyglucosamine-natural amino acid derivative compounds, wherein the natural amino acid may be histidine or lysine. The amino is bound through a peptide (amide) bond via its carbonyl to the primary amine on the glucosamines of polyglucosamine:

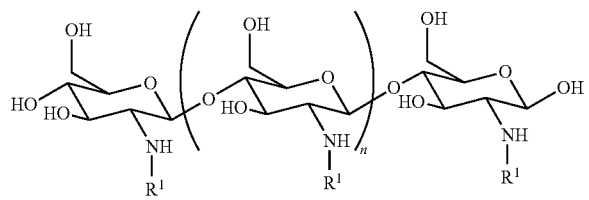

wherein each $R^1$ is independently selected from hydrogen, acetyl, and a group of the following formula:

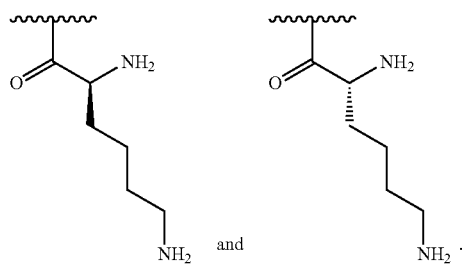 [SMILES: *C(=O)[C@@H](N)CCCCN ; *C(=O)[C@H](N)CCCCN]

or a racemic mixture thereof, wherein at least 25% of $R^1$ substituents are H, at least 1% are acetyl, and at least 2% are a group of the formula shown above; or a group of the following formula:

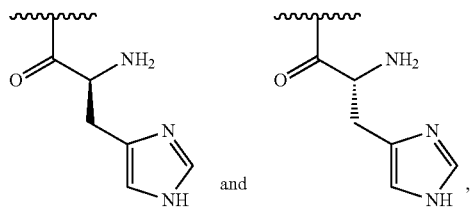 [SMILES: *C(=O)[C@@H](N)Cc1c[nH]cn1 ; *C(=O)[C@H](N)Cc1c[nH]cn1]

or a racemic mixture thereof, wherein at least 25% of $R^1$ substituents are H, at least 1% are acetyl, and at least 2% are a group of the formula shown above.

(C) Polyglucosamine-Unnatural Amino Acid Compounds

In some embodiments, the present invention is directed to polyglucosamine-unnatural amino acid compounds, where the unnatural amino acid is bound through a peptide (amide) bond via its carbonyl to the primary amine on the glucosamines of polyglucosamine:

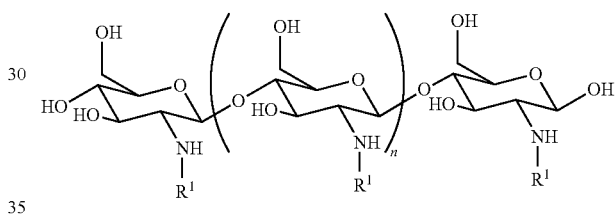

wherein each $R^1$ is independently selected from hydrogen, acetyl, and a group of the following formula:

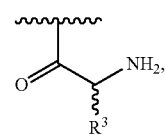

wherein $R^3$ is an unnatural amino acid side chain, and wherein at least 25% of $R^1$ substituents are H, at least 1% are acetyl, and at least 2% are a group of the formula shown above.

Unnatural amino acids are those with side chains not normally found in biological systems, such as ornithine (2,5-diaminopentanoic acid). Any unnatural amino acid may be used in accordance with the invention. In some embodiments, the unnatural amino acids coupled to polyglucosamine have the following formulae:

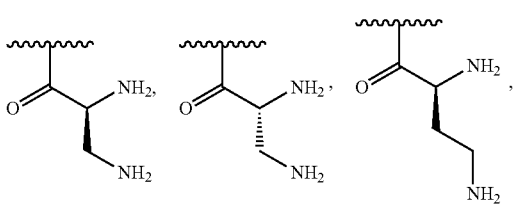

-continued

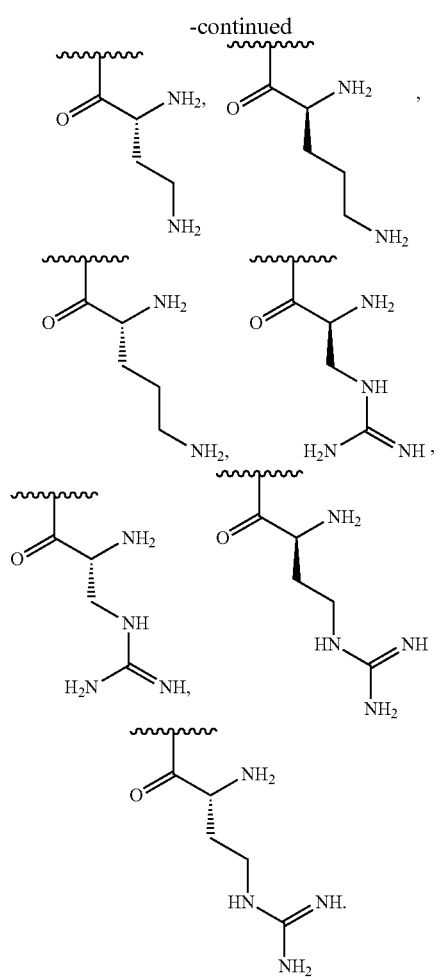

(D) Polyglucosamine-Acid Amine Compounds

In some embodiments, the present invention is directed to polyglucosamine-acid amine compounds, or their guanidylated counterparts. The acid amine is bound through a peptide (amide) bond via its carbonyl to the primary amine on the glucosamines of polyglucosamine:

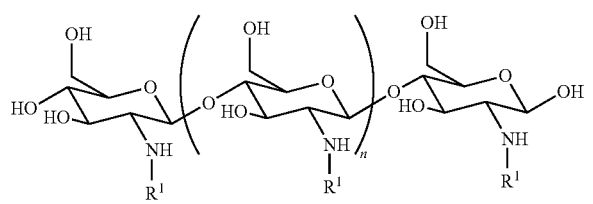

wherein each $R^1$ is independently selected from hydrogen, acetyl, and a group of the following formula:

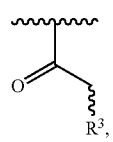

wherein $R^3$ is selected from amino, guanidino, and $C_1$-$C_6$ alkyl substituted with an amino or a guanidino group, wherein at least 25% of $R^1$ substituents are H, at least 1% are acetyl, and at least 2% are a group of the formula shown above In some embodiments, $R^1$ is selected from one of the following:

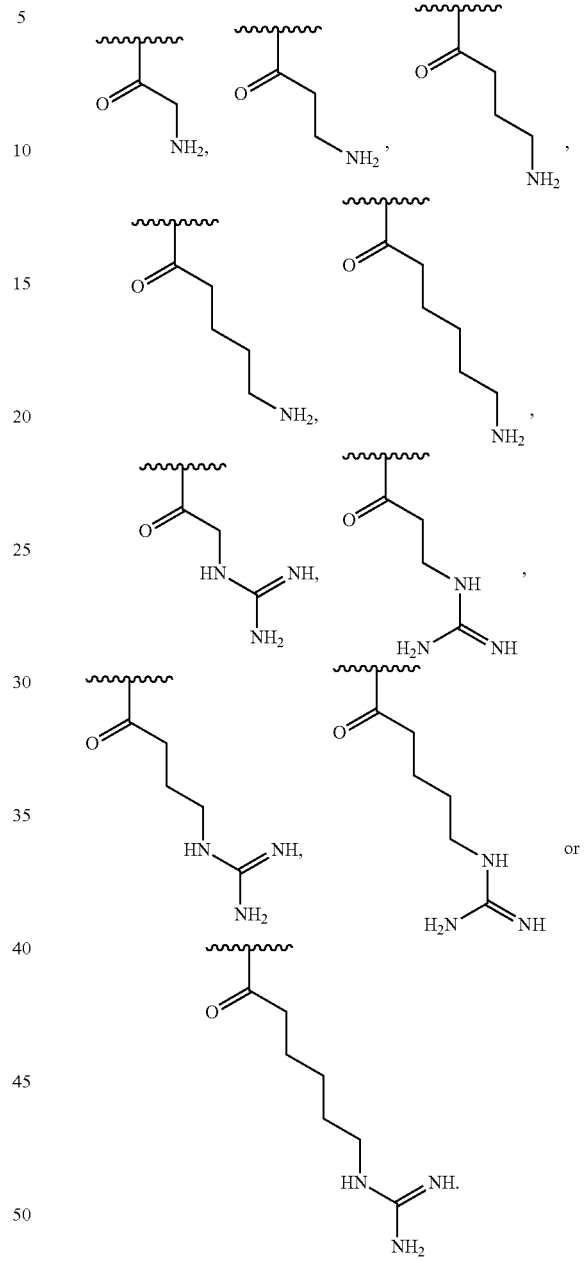

(E) Polyglucosamine-Guanidine Compounds

In some embodiments, the present invention is directed to polyglucosamine-guanidine compounds.

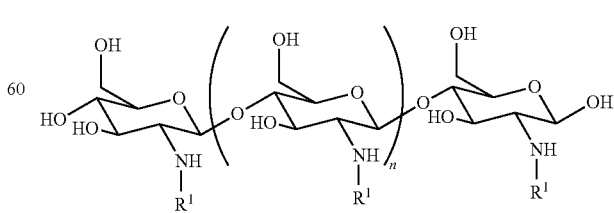

wherein each $R^1$ is independently selected from hydrogen, acetyl, and a group in which $R^1$, together with the nitrogen to which it is attached, forms a guanidine moiety; wherein at least 25% of $R^1$ substituents are H, at least 1% are acetyl, and at least 2% form a guanidine moiety together with the nitrogen to which it is attached.

(F) Neutral Polyglucosamine Derivative Compounds

In some embodiments, the present invention is directed to neutral polyglucosamine derivative compounds. Exemplary neutral polyglucosamine derivative compounds include those where one or more amine nitrogens of the polyglucosamine have been covalently attached to a neutral moiety such as a sugar:

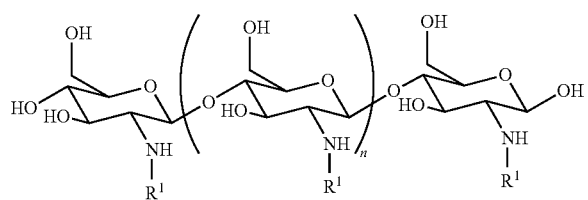

wherein each $R^1$ is independently selected from hydrogen, acetyl, and a sugar (e.g., a naturally occurring or modified sugar) or an α-hydroxy acid. Sugars can be monosaccharides, disaccharides or polysaccharides such as glucose, mannose, lactose, maltose, cellobiose, sucrose, amylose, glycogen, cellulose, gluconate, or pyruvate. Sugars can be covalently attached via a spacer or via the carboxylic acid, ketone or aldehyde group of the terminal sugar. Examples of α-hydroxy acids include glycolic acid, lactic acid, and citric acid. In some preferred embodiments, the neutral polyglucosamine derivative is polyglucosamine-lactobionic acid compound or polyglucosamine-glycolic acid compound. Exemplary salts and coderivatives include those known in the art, for example, those described in US 2007/0281904, the contents of which is incorporated by reference in its entirety.

In some embodiments, a compound or composition described herein, e.g., a compound or composition comprising PAAG, is administered in combination with another agent. Exemplary agents include disinfectants and antibiotics. In some embodiments, the disinfectant is chlorhexidine or betadine. In some embodiments, the antibiotic is chlorhexidine, betadine, hydrogen peroxide, honey, silvadene, silver sufadiazene, sulfacetamide sodium, erythromycin, neomycin, polymyxin b, mafenide (e.g. sulfamylon) bacitracin/neomycin/polymyxin b (triple antibiotic), mupirocin (e.g. Bactroban) retapamulin (Altaba), or tetracycline (e.g. topicycline).

As used herein, "administered in combination" or a combined administration of two agents means that two or more agents (e.g., compositions and compounds described herein) are administered to a subject at the same time or within an interval such that there is overlap of an effect of each agent on the subject. Preferably they are administered within 60, 15, 10, 5, or 1 minute of one another. Preferably the administrations of the agents are spaced sufficiently close together such that a combinatorial (e.g., a synergistic) effect is achieved. The agents can be administered simultaneously, for example in a combined unit dose (providing simultaneous delivery of both agents). Alternatively, the agents can be administered at a specified time interval, for example, an interval of minutes, hours, days or weeks. Generally, the agents are concurrently bioavailable, e.g., detectable, in the subject.

Antibacterials and Antiseptics

The compositions and methods described herein can be used in combination of one or more of antibiotics, to treat one or more diseases and conditions described herein. General classes of antibiotics include, e.g., aminoglycosides, bacitracin, beta-lactam antibiotics, cephalosporins, chloramphenicol, glycopeptides, macrolides, lincosamides, penicillins, quinolones, rifampin, glycopeptide, tetracyclines, trimethoprim and sulfonamides. In some embodiments, the administrations of a combination of agents and therapeutics are spaced sufficiently close together such that a synergistic effect is achieved. Exemplary antibiotics within the classes recited above are provided as follows. Exemplary aminoglycosides include Streptomycin, Neomycin, Framycetin, Parpmycin, Ribostamycin, Kanamycin, Amikacin, Dibekacin, Tobramycin, Hygromycin B, Spectinomycin, Gentamicin, Netilmicin, Sisomicin, Isepamicin, Verdamicin, Amikin, Garamycin, Kantrex, Netromycin, Nebcin, and Humatin. Exemplary carbacephems include Loracarbef (Lorabid). Exemplary carbapenems include Ertapenem, Invanz, Doripenem, Finibax, Imipenem/Cilastatin, Primaxin, Meropenem, and Menem. Exemplary cephalosporins include Cefadroxil, Durisef, Cefazolin, Ancef, Cefalotin, Cefalothin, Keflin, Cefalexin, Keflex, Cefaclor, Ceclor, Cefamandole, Mandole, Cefoxitin, Mefoxin, Cefprozill, Cefzil, Cefuroxime, Ceftin, Zinnat, Cefixime, Suprax, Cefdinir, Omnicef, Cefditoren, Spectracef, Cefoperazone, Cefobid, Cefotaxime, Claforan, Cefpodoxime, Fortaz, Ceftibuten, Cedax, Ceftizoxime, Ceftriaxone, Rocephin, Cefepime, Maxipime, and Ceftrobiprole. Exemplary glycopeptides include Dalbavancin, Oritavancin, Teicoplanin, Vancomycin, and Vancocin. Exemplary macrolides include Azithromycin, Sithromax, Sumamed, Zitrocin, Clarithromycin, Biaxin, Dirithromycin, Erythromycin, Erythocin, Erythroped, Roxithromycin, Troleandomycin, Telithromycin, Ketek, and Spectinomycin. Exemplary monobactams include Aztreonam. Exemplary penicillins include Amoxicillin, Novamox, Aoxil, Ampicillin, Alocillin, Carbenicillin, Coxacillin, Diloxacillin, Flucloxacillin Floxapen, Mezlocillin, Methicillin, Nafcillin, Oxacillin, Penicillin, and Ticarcillin. Exemplary polypeptides include Bacitracin, Colistin, and Polymyxin B. Exemplary quiniolones include Ciproflaxin, Cipro, Ciproxin, Ciprobay, Enoxacin, Gatifloxacin, Tequin, Levofloxacin, Levaquin, Lomefloxacin, Moxifloxacin, Avelox, Norfloxacin, Noroxin, Ofloxacin, Ocuflox, Trovafloxacin, and Trovan. Exemplary sulfonamides include Mefenide, Prontosil (archaic), Sulfacetamide, Sulfamethizole, Sulfanilamide (archaic), Sulfasalazine, Sulfisoxazole, Trimethoprim, Trimethoprim-Sulfamethoxazole (cotrimoxazole), and Bactrim. Exemplary tetracyclines include Demeclocyline, Doxycycline, Vibramycin, Minocycline, Minocin, Oxytetracycline, Tenacin, Tetracycline, and Sumycin. Other exemplary antibiotics include Salvarsan, Chloamphenicol, Chloromycetin, Clindamycin, Cleocin, Linomycin, Ethambutol, Fosfomycin, Fusidic Acid, Fucidin, Furazolidone, Isoniazid, Linezolid, Zyvox, Metronidazole, Flagyl, Mupirocin, Bactroban, Nitrofurantion, Macrodantin, Macrobid, Platensimycin, Pyrazinamide, Quinupristin/Dalfopristin (Syncerid), Rifampin (Rifampicin), and Tinidazole. Exemplary antibiotics also include xylitol.

Kits

A compound or composition described herein can be provided in a kit. The kit includes (a) a composition that includes a compound described herein, and, optionally (b) informational material. The informational material can be descriptive, instructional, marketing or other material that relates to the methods described herein and/or the use of the compound described herein for the methods described herein.

The informational material of the kits is not limited in its form. In one embodiment, the informational material can include information about production of the compound, molecular weight of the compound, concentration, date of expiration, batch or production site information, and so forth. In one embodiment, the informational material relates to use of the compound described herein to treat a disorder described herein.

In one embodiment, the informational material can include instructions to administer the compound described herein in a suitable manner to perform the methods described herein, e.g., in a suitable dose, dosage form, or mode of administration (e.g., a dose, dosage form, or mode of administration described herein). In some embodiments, the doses, dosage forms, or mode of administration can be, e.g., transdermal or transmucosal. In some embodiments, the doses, dosage forms, or modes of administration are e.g., topical (e.g., epicutaneous, intradermal, subcutaneous, sublingual, bucosal, inhalational, eye drops, ear drops). In another embodiment, the informational material can include instructions to administer the compound described herein to a suitable subject, e.g., an animal, e.g., a large animal having or at risk for a disorder described herein. For example, the material can include instructions to administer the compound described herein to such a subject.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as computer readable material, video recording, or audio recording. In another embodiment, the informational material of the kit is contact information, e.g., a physical address, email address, website, or telephone number, where a user of the kit can obtain substantive information about a compound described herein and/or its use in the methods described herein. The informational material can also be provided in any combination of formats.

In addition to a compound described herein, the composition of the kit can include other ingredients, such as a solvent or buffer, a stabilizer, a preservative, and/or a second compound for treating a condition or disorder described herein. Alternatively, the other ingredients can be included in the kit, but in different compositions or containers than the compound described herein. In such embodiments, the kit can include instructions for admixing the compound described herein and the other ingredients, or for using a compound described herein together with the other ingredients.

The kit can include one or more containers for the composition containing the compound described herein. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of a compound described herein. For example, the kit includes a plurality of syringes, ampules, foil packets, or blister packs, each containing a single unit dose of a compound described herein. The containers of the kits can be sealed, air tight, waterproof (e.g., impermeable to changes in moisture or evaporation), and/or light-tight.

The kit optionally includes a device suitable for administration of the composition, e.g., a hand held pump irrigator, spray, syringe, pipette, dropper, swab (e.g., a cotton swab or wooden swab), or any such delivery device.

EXAMPLES

Unless otherwise indicated, PAAG as used in the Examples below (including in PAAG Active Rinse) is 18 to 30% functionalized, 20 to 150 kDa PAAG. Also, unless otherwise indicated, PAAG Active Rinse is a solution formulation of PAAG in water. Also, unless otherwise indicated, PAAG Active Gel is a gel formulation of PAAG in 0.5% by weight or 1% by weight of HPMC in water.

Zoo studies (Examples 1-6). Zoo studies demonstrate the effectiveness of PAAG Active Rinse when used to treat elephant and rhinoceros foot disease, pressure ulcers, abscesses, and impacted temporal glands. The ability of PAAG Active Rinse and PAAG Active Gel (1% w/v HPMC) formulation to enhance the healing of infected wounds augments standard treatment and addresses a common problem with wound treatments in that they are constantly exposed to the environment and prone to bacterial infection. The healing wounds were generally described as smoothed out and having better epithelial adherence along the margins. Veterinarians noted that the healing process continued to progress faster than normal with the use of PAAG Active Rinse.

Porcine partial thickness wound model studies (Examples 7-12). The purpose of these study was to examine the activity of a new PAAG wound rinse formulation on Methicillin Resistant *Staphylococcus aureus* (MRSA) using a porcine partial thickness wound model (Davis et al., 2005; Davis and Bouzari, 2004; Mertz et al., 2003; Mertz et al., 1999). A porcine model was used for our experimental research animal since swine skin is morphologically similar to human skin (Meyer et al., 1975). Wound healing data from porcine models have also been shown to correlate more closely to humans than rodents (Sullivan et al., 2001).

Example 1

Effectiveness of PAAG Active Rinse in Elephant Foot Pad Wound Healing

Elephant #1
History:
A male 13,000 lbs Asian elephant had a traumatic injury in 2009 resulting in avulsion of his left front foot pad approximately 6" in diameter as a superficial wound.
Protocol:
The foot pad was irrigated vigorously with tap water for gross debridement. General wound trimming with rongeur was completed if necessary. PAAG Active Rinse (21.3 kDa, 25.0% functionalized PAAG) 200 µg/mL aqueous suspension was applied with hand held pump irrigator for final wound irrigation and debridement. Debridement and wound irrigation was performed daily for a period of 2 months (FIG. 1).

Observations:

The foot pad wound did not exhibit inflammation or infection associated with PAAG Active Rinse use and was well tolerated. There was no indication of pain or other irritation exhibited during irrigation. A reduction in odor typically associated with foot infection was noticed after a few days. The wound irrigated with PAAG Active Rinse appeared to have less adherent exudate and fibrin debris than wounds irrigated with tap water or 0.05% chlorhexidine solution. Clinical impressions were that the wounds were cleaner and better managed with PAAG Active Rinse than other lavage solutions. The wound resolved with no other treatments necessary.

Example 2

Effectiveness of PAAG Active Rinse on a Chronic Lesion on the Left Front Nail of an Elephant Elephant #2
History:
A female 7,000 lb Asian elephant had a chronic fistula/ulcer on the bottom of her left front #4 nail since the 1980's. Due to the location of the wound, it was considered a chronic wound and was still undergoing treatment.
Protocol:
The wound was treated cyrosurgically to debride the necrotic and infected tissue prior to the first treatment with PAAG Active Rinse. The rinse was used daily. The ulcer was first irrigated vigorously with tap water for gross debridement. General wound trimming with rongeur and equine hoof knives was completed followed by final irrigation of 200 µg/mL PAAG Active Rinse (21.3 kDa, 25.0% functionalized PAAG) applied with a hand held pump. Debridement and wound irrigation was performed at daily intervals for a period of 2 months. (FIG. 2).
Observations:
The chronic wound lost the odor associated with infection and the cavity size was reduced and stayed cleaner. The transition between granulation and re-epithelialization was faster than normal after 3 weeks of treatment. The wound demonstrated a slowly accumulating granulation bed with rapid proliferating epithelium around the perimeter of the wound. Further, it appeared that the epithelium migrated fairly deeply into the wound. Treatment with PAAG Active Rinse made this chronic lesion more similar to typical wounds in the nail region. No loose granulation tissue after 1 week of treatment resulted in the lack of necessity to debride the wound. The elephant still has a smaller, milder, manageable wound without infection, which is addressed every 1 to 3 weeks as needed.

Example 3

Effectiveness of PAAG Active Rinse on the Right Temporal Gland Impacted with Exudate of an Elephant Elephant #2
History:
Elephant number two had her right temporal gland impacted with exudate. No other treatment was attempted prior to PAAG Active Rinse.
Protocol:
The abscess on the facial scent gland was instilled with PAAG Active Rinse (21.3 kDa, 25.0% functionalized PAAG) at 200 µg/mL and gently agitated as a flush. (FIG. 3).

Observations:
PAAG Active Rinse loosened up the material and helped to break up the cohesion of the material in the blocked gland. The blocked gland fully resolved after treatment of over a week.

Example 4

Effectiveness of PAAG Active Rinse on a Chronic Ulcer on the Bottom of Left Rear #4 Nail of an Elephant Elephant #3
History:
A 43 year-old female Asian elephant has a chronic ulcer on the bottom of her left rear #4 nail. She has a history of foot/nail disease over the last 10 years.
Protocol:
The wound was treated with Epsom salt soaks for the first 10 days prior to the treatment with 500 µg/mL PAAG Active Rinse (27.6 kDa, 22.0% functionalized PAAG). The ulcer was first irrigated vigorously with tap water for gross debridement. PAAG Active Rinse (approximately 50 ml) was applied with a hand held pump once in the morning and once in the evening, from December 2010 through August 2011. (FIG. 4).
Observations:
PAAG Active Rinse resolved the wound with no other treatments necessary.

Example 5

Effectiveness of PAAG Active Rinse on a Deep Abscess on the Front Left Foot of a Rhinoceros Rhinoceros #1
History:
A female 3,300 lb, 34 year-old rhinoceros suffers from a deep abscess on her front left foot.
Protocol:
The abscess was cleaned daily and debrided if necessary prior to PAAG Active Rinse treatment. 200 µg/mL PAAG Active Rinse (86.4 kDa, 26.8% functionalized PAAG) was applied with a hand held pump daily for 5 weeks.
Observations:
Daily treatment with PAAG Active Rinse showed excellent progress in healing (FIG. 5). The front left foot abscess was resolved.

Example 6

Effectiveness of PAAG Active Rinse on Pressure Ulcers on Both Hips of a Rhinoceros Rhinoceros #1
History:
A female 3,300 lb 34 year-old rhinoceros suffers from pressure ulcers on both hips for several months. They changed nature, becoming very wet, active and inflamed on Nov. 10, 2010. MRSA was isolated from both hips (a different bacterial strain from each hip) reported on Nov. 22, 2010.
Protocol:
Uniprim treatment (Equine TMPS powder dosed for 3,300 lbs) was administered once daily per rectum. The ulcers were trimmed for debridement and rinsed daily with PAAG Active Rinse at 500 µg/mL (37.0 kDa, 22.8% functionalized PAAG). On Dec. 2, 2010 the rinse was replaced with a PAAG Active Gel (1% HPMC) in order to provide continuous leave-on treatment.

Observations:

Daily treatment with the PAAG Active Rinse (rinse) showed excellent progress in healing in both the left hip (FIG. 6-7) and the right (FIG. 8).

Example 7

Wound Care Treatments Prevent Biofilm Formation

Procedure:

One animal was used for this study. The young female (approximately 2-3 months old) specific pathogen free (SPF: Looper Farms, North Carolina) pig weighing 25-30 kg was kept in-house for two weeks prior to initiating the experiment. The animal was fed a basal diet ad libitum and housed individually in our animal facilities (American Association for Accreditation of Laboratory Animal accredited) with controlled temperature (19-21° C.) and lights (12 h/12 h LD).

Forty-two (42) rectangular wounds measuring 10 mm×7 mm×0.5 mm deep were made in the paravertebral and thoracic area with a specialized electrokeratome fitted with a 7 mm blade. These wounds were separated from one another by 15 mm of unwounded skin. Three (3) wounds were randomly assigned to one of fourteen (14) treatment groups and then inoculated and treated as described in the FIG. 9.

A fresh culture of Methicillin Resistant *Staphylococcus aureus* (NRS 384/USA 300) served as the pathogen in this study. The challenge inoculum suspension was prepared by scraping the overnight growth from a culture plate into 4.5 ml of normal saline. This resulted in a suspension concentration of approximately $10^{10}$ colony forming units/ml (CFU/ml). Serial dilutions were made until a concentration in the order of $10^6$ CFU/ml was achieved as determined by optical density measurements. Additional serial dilutions of the suspension were plated onto culture media and the plates incubated aerobically overnight (16-24 hours) at 37° C. in order to quantify the exact concentration of viable organisms. This suspension was vortexed and 25 µl was inoculated into each wound, followed by 30 seconds of scrubbing with a sterile spatula to promote bacterial penetration of the skin. After inoculation, wounds were covered individually with a polyurethane film dressing for 24 hours to allow for biofilm formation.

After 24 hour biofilm formation, the polyurethane film dressings were removed and each wound was irrigated with PAAG functionalized 30.1% and 86.4 kDa at 1000 µg/mL either twice (×2) or four times (×4) using 10 ml syringes with 1.5" long 21 gauge needles held at a 45 degree angle over the wound. All wounds in groups B2, E2, and F2, as well as wounds 5 and 6 of group A2, were wiped once with sterile gauze soaked in 3 ml of sterile saline prior to treatment. Within 5 minutes after irrigation, these wounds were recovered. The wounds receiving PAAG Active Gel (1% w/v HPMC, 1% w/v PAAG, 30.1% functionalized and 86.4 kDa) treatments (groups C, G and H) were treated with enough material to completely cover the wounded area and surrounding normal skin. All wounds in these groups were covered with polyurethane film dressings immediately after treatment application and left alone for 24 hours until recovery. Groups G and H were treated with 200 µl of unknown active doses in order to prevent experimenter bias. Groups E and F received treatments made up of only the rinse vehicle while D and J were left completely untreated. These final four groups served as negative controls.

Three (3) wounds were harvested from groups A, B, E, F, and J immediately after treatment rinse application (FIG. 10). The remaining wounds from the other treatment groups (C, D, G, H, and I) were recovered 24 hours after application. To extract bacteria from the wounds, a sterile cylinder (22 mm inside diameter) was placed around the wound area. One (1) ml of all-purpose neutralizer solution was pipetted into the cylinder and the site scrubbed with a sterile Teflon spatula for 30 seconds. Serial dilutions were made from all culture samples and the extent of microbiological contamination was assessed using the Spiral Plater System (Spiral Biotech, Norwood, Mass.). This system deposits a 50 µl aliquot of scrub bacterial suspension over the surface of a rotating agar plate. Oxicillin Resistance Screening Agar (ORSAB) was used to isolate MRSA USA 300. All plates were incubated aerobically overnight (16-24 hours) at 37° C., after which the number of viable colonies was counted.

After counting the colonies, the data was tabulated and the Log of colony forming units/ml (Log CFU/ml) for MRSA USA 300 in each wound was determined. The mean of the Log CFU/ml and standard deviation was calculated for each time and treatment.

Results:

For wounds assessed 24 hours after treatment, those which received a debridement wipe plus a rinse with PAAG functionalized 30.1% and 86.4 kDa at 1000 µg/mL and the 1% PAAG/1% HPMC gel (Group I) had the lowest counts of MRSA at 7.93±0.14 Log CFU/ml. These experienced a 96.45% (1.45±0.08 Log CFU/ml) reduction in bacteria compared to the untreated wounds (FIG. 10). Wounds that received only the gel vehicle unaccompanied by an active component, a preliminary wipe, or a rinse (Group C) had the least amount of reduction in bacterial counts. This count (8.73±0.46 Log CFU/ml), however, was still a significant 77.95% lower than that of the untreated wounds. The gel with 1% PAAG/1% HPMC gel alone (Group H) exhibited slightly more effective activity than the 1% PAAG/0.5% HPMC gel alone (Group G). Wounds receiving the former treatment had an overall 90.23% (1.01±0.02 Log CFU/ml) reduction in MRSA USA300 microbes. While those treated with the latter experienced an 84.75% (0.82±0.27 Log CFU/ml) reduction (FIG. 10).

The treatment used in group B2 (wipe+four rinses of active A) was the overall most effective regimen in wounds assessed immediately after application, with a 95.77% reduction in bacterial counts with respect to untreated wounds. In terms of the wounds assessed 24 hours after treatment, the 1% PAAG/1% HPMC (gel Active Dose Y) had 5.55% reduction than the 1% PAAG/0.5% HPMC (gel Active Dose X). When combined with the debridement wipe and two 10 ml rinses of active component A, counts of MRSA USA300 were further reduced another 6.15%. This provided an overall reduction of 96.45% (FIG. 11).

In this porcine partial thickness wound model, wounds infected with Methicillin Resistant *Staphylococcus aureus* (MRSA) were treated with various PAAG formulations and demonstrated an average of a 95.77% reduction in bacterial counts with respect to untreated wounds immediately after application. Wounds assessed 24 hours after treatment combined with a debridement wipe showed MRSA counts reduced another 6.15%, providing an average overall reduction of 96.45% after only 1 day of treatment.

Example 8

Wound Care Treatments to Reduce *Acinetobacter baumannii* Biofilm Infection

Summary:

PAAG has been demonstrated to reduce established biofilm infections in wounds as well or better than the standard of care. In a deep partial thickness wound, porcine study of *A. baumannii* biofilm infection, rinse formulations of PAAG reduced bioburden to levels statistically significantly better than that of Silvadene® (silver sulfadiazine), which served as the positive control for the study. Furthermore, continued use of PAAG completed disinfection of the wound while not contributing to bacterial resistance. The objective of this study was to evaluate the microbiocidal prevention and treatment abilities of a novel rinse and gel on *Acinetobacter baumannii* ATCC19606 (AB) biofilm formation using a porcine partial-thickness wound model. In this experiment, 30.1% functionalized, 86.4 kDa PAAG was used. Active Gel is 1% w/v HPMC and 1% w/v PAAG in water, and Active Rinse is 1000 μg/mL PAAG in water. The animal was prepared and wounded as previously described. A fresh culture of *Acinetobacter baumannii* ATCC 19606 (AB) was used as the infectious agent in this study. The challenge inoculum suspension was prepared by scraping the overnight growth from a culture plate into 5 ml of normal saline. This resulted in a suspension concentration of approximately $10^{10}$ colony forming units/ml (CFU/ml). Serial dilutions were made until a concentration of $10^6$ CFU/ml was achieved, as determined by optical density. In addition, serial dilutions were plated onto selective media and plates were incubated aerobically overnight (16-24 hours) at 37° C. in order to quantify the exact concentrations of viable organisms used for this experiment. Immediately after wounding (day 0), 25 μl of the $10^6$ CFU/ml bacterial suspension was inoculated into each wound. All wounds were randomly assigned to one of the fourteen treatments groups (see experimental design FIG. 12) and then either treated and covered (Treatments A-H Biofilm Prevention) or only covered with a polyurethane film dressing to allow for biofilm formation (Treatment I-N Biofilm Elimination). All dressings were covered and secured by wrapping the animal with self-adherent elastic bandages (Coban; 3M, St. Paul, Minn.). Treatments were reapplied for all wounds and re-covered daily (FIG. 12). Wounds in treatment groups A-H were treated within 30 minutes after inoculation and those in treatment groups I-N were treated 24 hours after inoculation to allow for biofilm formation. Treatments were applied in various manners according to their makeup. With regard to gel compounds, enough test material to completely cover the wound and surrounding normal skin was applied approximately 2004 Wounds receiving the rinsing agent were each rinsed twice (×2) using 10 ml syringes with 1.5" long 21 gauge needles held at a 45 degree angle over the wound. During each rinse, two of the three wounds in the group were covered with sterile 1½" metal caps to prevent the liquid from flowing into them. After irrigation, excess fluid was wiped up with sterile gauze (outside of encircled wounding and un-wounded area).

In a 3 day porcine partial thickness wound model using *Acinetobacter baumannii* infection, formulations of PAAG reduced bioburden by 99.98% after 3 days of treatment, to levels similar to that of Sulfamylon® at 5%, which served as the positive control for the study (FIG. 13). At this concentration, Sulfamylon has been observed to delay wound healing.

Example 9

Wound Care Treatments are Persistent

Background:

PAAG is mucoadhesive and has residual activity, providing long-term protection even after the rinse is completed. PAAG adheres to tissues and prevents bacterial colonization longer than standard disinfectants. The persistence of its activity is critical in a treatment delivered at the time of injury to prevent subsequent infection.

Summary:

The objective of this study was to examine the effect of a topical formulation on second-degree burn wound healing using a porcine model. Laboratories have used porcine models for over 20 years to examine the effect of various materials on wound healing. The animals were prepared as previously described. Sixty three (63) second-degree burn wounds were made in the paravertebral and thoracic area by using six specially designed cylindrical brass rods weighing 358 g each, that were each heated in a boiling water bath to 100° C. A rod was removed from the water bath and wiped dry before application to the skin surface, to prevent water droplets from creating a steam burn on the skin. The brass rod was held at a vertical position on the skin (six seconds), with all pressure supplied by gravity, to make a burn wound 8.5 mm (diameter)×0.8 mm (deep). Immediately after burning, the roof of the burn blister was removed with a sterile spatula. The wounds were randomly assigned to seven treatment regimens (nine wounds per treatment). All burn wounds were treated with the appropriate treatment as described in "treatment regimen" section below. The experimental design is shown in FIG. 14. In these experiments, 54 kDa, 23% functionalized PAAG was used. Active Dose X is 250 μg/mL PAAG, Active Dose Y is 500 μg/mL PAAG, Active Gel dose X is 1% w/v PAAG and 0.5% w/v HPMC in water, and Active Gel dose Y is 1% w/v PAAG and 0.5% w/v HPMC in water.

Nine (9) wounds were assigned to each treatment group. Treatment groups were randomly assigned to different anatomical areas on each pig. Wounds were treated within 20 minutes after wound creation (on day 0). Enough gel treatment, liquid treatment or vehicle were applied directly on the wound to cover the entire wound (approximately 200 μl) and were then covered with polyurethane film dressing (Tegaderm; 3M, St. Paul, Minn.). Treatments were applied once daily for the next six days. Polyurethane film dressings were changed daily after treatment application. All dressings will be covered and secured by wrapping the animal with self-adherent elastic bandages (Coban; 3M, St. Paul, Minn.). After 7 days of treatment application, the experiment was stopped.

Three biopsies were taken from each treatment group on days 5 and 7 after wounding (note: on day 21, biopsies were not taken since on days 3-6, gel treated wounds demonstrated marked to exuberant irritation: see clinical observations below). The wedge biopsy was obtained through the center of the wounds including normal adjacent skin on both sides. These specimens were placed in formalin then stained with hematoxylin and eosin (H&E). One section per block was analyzed. The specimens were evaluated blinded via light microscopy and examined for the following elements to determine a potential treatment response:

1) Percent of wound epithelialized (%)—Measurement of the length of the wound surface that has been covered with epithelium, and 2) Epithelial thickness (cell layers μm)—The epithelial thickness may vary from area to area within the biopsy. The thickness of the epithelium in μm was be measured on five equal distance points from each other in the biopsy and averaged.

Results:

The safety, tolerability and wound healing capabilities of PAAG were assessed in a porcine, second-degree burn model. The epithelial thickness is a measure of an average thickness of five points of newly formed epithelium. This measurement reflects the process of keratinocyte proliferation, differentiation, and epidermal maturation. At day 5 and 7 post-wounding, group B had thicker epidermis than the other 3 groups on A. Untreated air exposed group had thicker epidermis than the other 3 groups in both assessment days. The percent of re-epithelialization represents the percent of the wound area covered by newly formed epidermis with one or more layers of keratinocytes, which is a good index for the speed of keratinocyte migration and the first step of the re-epithelialization (FIG. 15). On day 5, the early stage of wound repair, groups B and C were more re-epithelialized than group G. On day 7, all groups were 100% re-epithelialized, except untreated wounds (FIG. 16).

The treatment effect on epithelialization and epithelial thickness were improved by the 500 μg/mL daily treatment of PAAG, although the lower dose and sterile rinse with vehicle both showed improvements in wound healing over no treatment. These studies demonstrate that the treatment itself is not detrimental to the wound, and in fact promotes wound healing.

Example 10

Wound Care Treatments Stimulate Healing

Background:

PAAG aggregates bacterial pathogens and provides a barrier to colonization. Although current wound rinses may contain disinfectants such as chlorhexidine or silver, these disinfectants damage tissues and limit healing. PAAG does not limit healing and has in some cases enhanced the healing rate relative to saline. In a full thickness porcine wound, PAAG stimulated epithelialization relative to control, demonstrating that PAAG is not only safe for tissues, but also provides enhanced regeneration.

Summary:

The objective of this study was to determine the effects of a new formulation on the healing of full thickness wounds using a porcine model. The animals were prepared as previously described. Forty-five (45) full thickness wounds were made on the paravertebral and thoracic area with a 10 mm circular biopsy punch. The wounds were separated from one another by 15 mm of unwounded skin. The wounds were randomly assigned to five treatment regimens, nine wounds per treatment (FIG. 17). In this experiment, Active Dose X is 200 μg/mL PAAG (81 kDa, 21% functionalized), Gel Active Dose X is 5,000 μg/mL PAAG (81 kDa, 21% functionalized).

Nine (9) wounds were assigned to each treatment group. Treatment groups were randomly assigned to different anatomical areas on each pig. Wounds were first treated within 20 minutes (OR once hemostasis was achieved) after wound creation on day 0 and then once daily for the following 7 days. Treatments were applied once daily for the seven days and were covered with polyurethane film dressing (Tegaderm; 3M, St. Paul, Minn.). Enough of the rinse treatment was applied to cover each wound, and all wounds were covered with polyurethane film dressings. On day 7, all wounds were then covered with a non-adherent gauze dressing. All dressings were covered and secured by wrapping the animal with self-adherent elastic bandages (Coban; 3M, St. Paul, Minn.).

Three biopsies were taken from each treatment group on days 5, 7 and 21 after wounding. Biopsies were wedge excisional biopsies. The wedge biopsy was obtained through the center of each wound, making sure to include normal adjacent skin on both sides. These specimens were placed in formalin, then stained with hematoxylin and eosin (H&E). One section per block was analyzed. The specimens were evaluated blinded via light microscopy and examined for the following elements to determine a potential treatment response:

1) Percent of wound epithelialized (%)—Measurement of the length of the wound surface that has been covered with epithelium;
2) Epithelial thickness (cell layers μm)—The epithelial thickness may vary from area to area within the biopsy. The thickness of the epithelium in Σm was measured on five equal distance points from each other in the biopsy and averaged;
3) White cell infiltrate—Measured by the presence and amount of subepithelial mixed leukocytic infiltrates. Mean Score: 1=absent, 2=mild, 3=moderate, 4=marked, 5=exuberant;
4) Granulation Tissue Formation—The approximate amount of new granulation tissue formation (dermis) was graded as follows: 1=<5%, 2=6-25%, 3=26-50%, 4=51-75%, 5=76-100%, and;
5) New Blood Vessel Formation—Presence of new blood vessels (non-quantitative). Mean Score: 1=absent, 2=mild, 3=moderate, 4=marked, 5=exuberant. Digital photographs were taken of representative wounds at each assessment time to document any signs of erythema, infection or wound closure.

Results:

The percent of re-epithelialization represents the percent of the wound area covered by newly formed epidermis with one or more layers of keratinocytes, which is a good index for the speed of keratinocyte migration and the first step of re-epithelialization. At early stage of wound repair of day 5, all treatments groups (Active Dose, Vehicle, Gel Active and Gel Vehicle Dose) were more re-epithelialized than group Untreated control group. At day 7, Active dose treatment group had slightly more reepithelialization than wounds treated with Vehicle, or Gel (with either Active or Vehicle Dose), but no difference as seen compared with untreated wounds remaining. At day 21, all groups 100% re-epithelialized (FIG. 18).

The epithelial thickness is a measure of an average thickness of five points of newly formed epithelium. This measurement reflects the process of keratinocyte proliferation, differentiation, and epidermal maturation. At day 5 post-wounding, wounds treated with Gel (with either active or vehicle) formulation had thicker epidermis than other 3 groups. At day 7, wounds treated with Gel (with Vehicle) had thicker epidermis than all other 4 groups, while Gel (with active dose) treatment groups had thicker epidermis than the other 4 groups at day 21 (FIG. 19).

Dermal reconstitution begins about 3 to 4 days of following injury, a hallmark beginning granulation tissue formation, which includes new blood vessel formation (angiogenesis) and accumulation of fibroblasts and collagen extracellular matrices. The granulation tissue formation measures the percent of wound bed filled with newly formed granulation tissue. At early stage of wound healing day 5, groups C and D Gel (Active Dose) and Gel (Vehicle) had more granulation tissue formation than other three groups. No difference was observed at days 7 and 21 between all treatment groups (FIG. 20).

All treatments appeared to enhance the rate of epithelialization early in comparison to untreated control, however by day 7, no major differences were noted. No adverse effects with regards to irritation as measured by white cell infiltrate were noted with any of the treatments. The gel formulations (both active and vehicle) appeared to have a slight increase in the amount of granulation early on (day 5), however by day 7, all treatment groups appeared equal. Due to the small sample size, no statistical differences among treatments were seen. Overall, the agents examined appeared not to be detrimental to healing, and in fact may promote the rate of epithelialization (as seen during the early assessment times).

Example 11

Effectiveness of Antimicrobial Rinse on Proliferation of *Acinetobacter baumannii* and MRSA in a Deep Partial Thickness Biofilm Prevention Porcine Wound Model Summary:

The animals were prepared as described (above). Ninety-six (96) rectangular wounds measuring 10 mm×7 mm×0.5 mm deep were made in the paravertebral and thoracic area with a specialized electrokeratome fitted with a 7 mm blade. The wounds were separated from one another by 15 mm of unwounded skin and individually dressed. The wounds were then inoculated and treated. A fresh culture of *Acinetobacter baumannii* ATCC 19606 or Methicillin Resistant *Staphylococcus aureus* (NRS 384/USA 300) was used in these studies. The challenge inoculum suspension was prepared by scraping the overnight growth from a culture plate into 5 ml of normal saline. This resulted in a suspension concentration of approximately $10^{10}$ colony forming units/ml (CFU/ml) for each bacteria. Serial dilutions were made until a concentration of $10^6$ CFU/ml was achieved. The inoculum was vortexed and 25 ml of the suspension inoculated into each wound. In addition, serial dilutions of the suspension were plated onto selective media and the plates were incubated aerobically overnight (16-24 hours) at 37° C., in order to quantify the exact concentration of viable organisms used for this experiment. In this experiment, Active Rinse is 1000 μg/mL PAAG (30.1% functionalized, 86.4 kDa PAAG) in water.

All wounds were treated within 30 minutes after inoculation. Treatments A and B were rinsed twice (×2) using 10 ml syringes with 1.5" long 21 gauge needles held at a 45 degree angle over the wounds. Wounds were then treated one and two days following initial treatment. During each treatment, the wounds in each group were covered with sterile 1½" metal caps to prevent the rinse from flowing into the other wounds. The positive control wounds were treated by applying enough test material (≅200 mg) to completely cover the wound and surrounding normal skin, and were spread out gently with a sterile Teflon spatula. After the treatment application, all wounds were covered with polyurethane film dressing (Tegaderm; 3M, St. Paul, Minn.). The polyurethane film dressings were secured along the edges using surgical tape. All dressings were covered and secured by wrapping the animal with self-adherent elastic bandages (Coban; 3M, St. Paul, Minn.).

Each wound was irrigated using two (×2) rinses of 10 ml of fluid. After irrigation, excess fluid was wiped up with sterile gauze (outside of encircled wounding and un-wounded area).

Twelve (12) wounds were recovered from each treatment group on each assessment day (days 3 and 4). To recover bacteria from the wounds, a sterile surgical steel cylinder (22 mm inside diameter) was placed around the wound area. One (1) ml of all-purpose neutralizer solution was pipetted into the cylinder and the site was scrubbed with a sterile Teflon spatula for thirty (30) seconds. Serial dilutions were made from all culture samples, and the extent of microbiological contamination was assessed using the Spiral Plater System (Spiral Biotech, Norwood, Mass.). Leeds *Acinetobacter* medium was used to isolate *Acinetobacter baumannii* (ATCC 19606) from the wounds. Oxicillin Resistance Screening Agar (ORSAB) was used to isolate MRSA USA 300. All plates were incubated aerobically overnight 24 hours at 37° C., after which time the number of viable colonies were counted.

Results:

Representative photos of AB infected wounds were taken during the study. Observations were made during treatment applications and on assessment times. Descriptive terms for swelling and erythema: absent<slight<mild<moderate< marked<exuberant. No erythema or swelling were observed during the study. See Photos (FIG. 21) for assessment days.

After counting the colonies, the CFU data was tabulated and the Log of Colony Forming Units/ml (Log CFU/ml) determined. The mean of the Log (CFU/ml) and standard deviations were then calculated for each time and treatment. The data was then combined with the previous study's results and analyzed for significance using ANOVA, which analyzed the mean Log CFU/ml for the combined animal data between all treatments. The Students T-test for the data compared between assessment days. On day 3, wounds treated with active rinse showed significant biofilm prevention of *Acinetobacter baumannii* (AB). Results demonstrated the ability of active rinse to reduce the bacterial count (6.60±0.61 Log CFU/ml) in comparison to other treatment regimen (the differences were significant ($p<0.05$)) only compared with Vehicle rinse and untreated control (FIG. 22). Active Rinse significantly reduced ($p<0.05$) the bacterial counts by 1.53±0.11 and 2.24±0.13 Log CFU/ml compared with Vehicle rinse and untreated control, respectively. These values represent a 97.07 and 99.42% percentage of reduction AB in the wounds. Similar bacteria count was observed in wounds treated with Active Rinse and Silver sulfadiazine (6.60±0.61 and 6.70±0.51, respectively) (There were no significant differences ($p<0.05$)). Wounds treated with Vehicle Rinse showed a 8.14±0.72 Log CFU/ml of AB on day 3 (with a significant differences ($p<0.05$)) compared with the bacterial count recovered from wounds untreated (8.84±0.49 Log CFU/ml). (FIG. 22).

Positive control, (Silver Sulfadiazine (SSD)) treated wounds exhibited the second most significant ($p<0.05$) bacterial reduction of AB on day 3 with a reduction amount of 2.14±0.01 Log CFU/ml compared to the polyurethane control. This value represents a 99.28% reduction in comparison to the untreated wounds. In addition, the wounds treated with the SSD control significantly reduced ($p<0.05$) the bacterial counts by 1.44±0.23 Log CFU/ml in comparison to the wounds treated with Vehicle Rinse (a 96.38% reduction between these groups on this day). (FIG. 22).

On day 4, the exhibited trends were similar to the trends observed on the $3^{rd}$ assessment day. The Active Rinse wounds harbored 5.80±0.31 Log CFU/ml of AB, eliminating the most AB. The Active Rinse significantly (p<0.05) reduced 3.51±0.12 Log CFU/ml of bacteria (99.97% reduction) in comparison to the untreated wounds. Furthermore, the Active Rinse also significantly (p<0.05) reduced AB compared to the Vehicle Rinse and exhibited a reduction value of 2.62±0.15 Log CFU/ml (99.76% bacteria reduction). And finally, the Active Rinse significantly (p<0.05) reduced 0.54±0.17 Log CFU/ml (70.99% reduction) *Acinetobacter baumannii* in comparison to the SSD control on day 4 (FIG. 22).

The SSD control significantly reduced (p<0.05) the bacterial counts by 2.97±0.29 Log CFU/ml (99.89% reduction) in comparison to the untreated control wounds thereby harboring a total of 6.34±0.47 Log CFU/ml of AB. Furthermore, the SSD control significantly (p<0.05) reduced 2.09±0.02 Log CFU/ml (99.18% reduction) of bacteria in comparison to the Vehicle Rinse treated wounds that harbored 8.43±0.45 Log CFU/ml of bacteria. And finally, the Vehicle Rinse treatment significantly reduced (p<0.05) the bacterial counts by 0.89±0.27 Log CFU/ml (87.04% reduction) in comparison to the untreated control wounds (FIG. 23).

When comparing the various treatments reductive capabilities across the assessment days, it became apparent that the Active Rinse treatment successfully eliminated the greatest amount of microorganisms from day 3 to day 4. The Active Rinse significantly (p<0.05) reduced 0.80±0.31 Log CFU/ml AB bacteria and exhibited 84.21% of bacteria reduction. The Active Rinse treatment was the only treatment group to significantly reduce (p<0.05) the bacteria counts from day 3 to day 4. The SSD treated wounds exhibited a 0.36±0.02 Log CFU/ml reduction (56.01% reduction) of AB between days 3 and 4 and was the only other treatment group that was able to reduce the colonies between assessment days as the other groups had an increase in the amount of bacteria from day 3 to day 4. The Vehicle Rinse exhibited an increase in the amount of bacteria by 0.29±0.27 Log CFU/ml (48.52% increase) by day 4 and the untreated wounds demonstrated a significant increase (p<0.05) in the amount of AB by day 4 with 0.47±0.30 Log CFU/ml (66.44% increase) more bacteria represented (FIG. 23).

The Active Rinse was the most effective treatment in reducing the overall bacterial counts, when considering the amount reduced between assessment days and, in comparison to the untreated wounds. A total of 99.42% of AB was reduced by day 3 assessment with this treatment and a total of 99.97% was reduced by the end of the study (day 4).

The Silver Sulfadiazine cream (positive control) reduced the second greatest amount of bacteria out of all the different treatment groups, and was the only other treatment to significantly (p<0.05) reduce the amounts of bacteria on both assessments days in comparison to the untreated wounds (99.28% day 3) and (99.89% day 4) and the Vehicle Rinse (96.38% day 3) and (99.18% day 4).

The Vehicle Rinse reduced the amounts of AB by 80.12% for day 3 and 87.04% for day 4 in comparison to the untreated wounds, and did not reduce enough microorganisms to obtain statistical significance. Despite the reduction accounted for on day 3, there was actually an increase in the amount of bacteria infecting the wounds from day 3 to day 4 (of by 48.52%).

Similar studies examining MRSA show that similar observations were observed with Gram-positive bacteria at showing the positive control the antibiotic mupirocin) and Active Rinse significantly reduced biofilm infection (FIG. 24). This study also indicated that a significant reduction in biofilm infection assessed at day 3 compared to day 4 was achieved in the positive control group and Active Rinse treatment day (FIG. 25).

Example 12

Residual Antibacterial Activity on Porcine Skin

Background:

While many topical antibacterial treatments work on contact, the ability to retain residual antibacterial activity is a significant advantage. A prophylactic treatment helps to prevent infection if applied prior to or early in the colonization process before infection is established. The maintenance of antibacterial activity after initial treatment can reduce the number of treatments and thus limit the disturbance of a healing wound that might increase the opportunity for further infections.

Protocol

The residual antibacterial activity of PAAG (25%, 43 kDa) and other topical products was evaluated against MRSA strain MW-2 contaminated pigskins. The pigskins were obtained from Sinclair Research Center, Inc. (Colombia, Mo.). They were shaved and cleaned, divided into 1-inch square sections and placed in sterile Petri dishes to prepare for testing. The pig skins (1×1 inch pieces, three per treatment group) were sterilized with UV radiation to sterilize the surface, then treated with; nothing, 70% ethanol, 60 ug/cm$^2$ PAAG in 70% ethanol, hydrogen peroxide, or ChloraPrep (commercial product consisting of 2% chlorhexidine in 70% ethanol. The volume of each treatment to cover the surface evenly was approximately 0.3 mL. Three pieces of pigskin were left untreated for controls to indicate sterilization of the skin had occurred. The treatments were allowed to dry on the surface of the skin for 1-hour then approximately 10$^3$ CFU of MRSA strain MW-2 was added to the surface. The bacteria were allowed to remain on the surface of the skin for 1-hour. Then the skin surface was pressed onto an agar plate and grown up for 24-hours at 37° C. to obtain a qualitative indication of the amount of bacteria remaining on the skin surface Results:

PAAG maintains prophylactic activity on pig skin as observed in the reduced recovery of CFU on agar following exposure to the skin surface (FIG. 26).

Example 13

Modulation of Inflammatory Response

Background:

Research into multiple sources of induced damage to tissues suggests that there are common downstream biological pathways that arise from physical, chemical, radiative or pathogenic mediators. The healing is limited by the downstream activation of inflammatory pathways, stimulated by an initial release of reactive oxygen species. [Sonis, 2010] This inflammatory activation leads to further tissue damage that limits healing, and in some cases, results in chronic inflammation and substantial scarring. Recent studies suggest that the mechanisms of mucosal, tissue and epithelial damage after initiation are mediated by some of the most primitive innate immune responses, such as those mediated by the toll-like receptors (TLR's) and Nod-like receptors (NLR's). [Sonis, 2004] The fundamental mediators of inflammation are linked through a common pathway that can be induced by the pathogen associated molecular pattern molecules (PAMP's), damage associated molecular patterns molecules (DAMP's) and chemical and radiation associated molecular pattern molecules (CRAMP's). The molecules likely actuate the process through interaction with TLR's and are responsible for the activation of common pathways associated with inflammation, damage and inability to heal. [Sonis, 2010].

Protocol:

The THP-1 human monocytic cell line was derived from one-year old male with acute lymphocytic leukemia. The cells are grown in suspension culture and can be differentiated to more macrophage-like cells using calcitriol, a vitamin D analog, or the phorbol ester PMA (phorbol 12-myristate 13-acetate). When PMA is used the cells become adherent and the literature suggests that cells are more differentiated than when treated with calcitriol. THP-1 cells were differentiated in the presence of PMA for 48 hours before being stimulated by the addition of LPS, an endotoxin that results in the expression of the pro inflammatory cytokine TNFa.

In a similar study, human U937 macrophages were seeded at $10^7$ cells/ml and activated with PMA for 24 hours. The supernatant was exchanged and after 24 hours the macrophages were treated with media alone or 200 µg/mL PAAG for 1 hour. The media was exchanged and the macrophages were stimulated with either bacterial DNA (5 hours) or LPS (4 hours). The IL-8 produced by the macrophage was measured by ELISA at 4, 5 and 24 hours.

Results:

In the presence of PAAG (18 kD, 25% functionalized), the expression of TNFa in THP-1 human monocyte cell line is reduced compared to cells treated with LPS alone (FIG. 27). We also examined the expression of an anti-inflammatory cytokine, IL-10, and found that its expression is increased in the presence of PAAG (FIG. 27). These data suggest that PAAG can affect the balance of cytokine production from activated macrophages.

Human U937 macrophage IL-8 production 4 and 24 hours after treatment with LPS (FIG. 28) or MRSA DNA (FIG. 29). Macrophages pre-treated with 200 µg/mL PAAG for 1-hour secreted significantly less IL-8 (p<0.002) after 4 and 24 hours compared to LPS treatment alone.

Example 14

Adhesion to Human Intestinal Epithelial Cells Indicates Mucoadhesion

Protocol:

PAAG reduces attachment and invasion of bacteria to epithelia and to epidermal cells in vitro. As one example, CaCo2 cells were grown to confluence and treated with 0 or 200 µg/mL of PAAG (23% functionalized, 37 kDa) for 1 hour. The cells were rinsed twice with media to remove PAAG in solution and then incubated with *Acinetobacter baumannii* for 3 hours.

Results:

FIG. 30 shows the percent (%) of bacterial inoculum that attached to a confluent monolayer of CaCo2 cells in culture after the hour co-culture incubation. Note that the PAAG has a protective effect against adhesion of bacteria and has a mucoadhesive substantively that remains after simple rinsing.

Example 15

Adhesion to Nasal Epithelial Cells Indicates Mucoadhesion

Protocol:

The ability of *S. aureus* (MW2) to adhere to RPMI 2560 nasal epithelium cells was assessed. The RPMI 2650 cell line (American Type Culture Collection) was seeded in 24-well cell culture plates at $2.5 \times 10^5$ cells per well. Cells were grown in Eagle's Minimal Essential Medium (EMEM) containing 10% fetal calf serum, 2 mM L-glutamine without antibiotics for 24 hours at 37° C. in atmosphere containing 5% $CO_2$. Confluent monolayer was washed once with DPBS and replaced with EMEM without serum 2 hours prior to start of experiment. Cells were pretreated for 5 minutes or 1 hour with either 200 µg/ml or 500 µg/ml of PAAG (30.1% functionalized, 86.4 kDa) in either DPBS or EMEM without serum or antibiotics. After the pretreatment of PAAG, each well was rinsed once with DPBS and replaced with EMEM without serum or antibiotics. The day prior to experiment, an overnight culture was initiated for *S. aureus* MW2, subsequently the overnight culture optical density was measured at the time of inoculation to provide an MOI of 1:100. Bacteria was given 1 hour from the start of the inoculation to adhere to epithelium monolayer, non-adherent cells were washed away with 2× rinses of DPBS to prevent nonspecific binding. Epithelium monolayer was lysed with 0.1% Triton X-100. Bacteria were quantified by plating serial dilutions of the lysate. All quantitative adherence assays were performed in triplicate.

Results:

At higher concentrations and longer treatment times, PAAG significantly prevented the attachment of MW2 onto nasal epithelium cells. PAAG dissolved in either (EMEM) media (FIG. 32) or PBS (FIG. 31) showed significantly decreased attachment, although PAAG dissolved in PBS was more effective. The increased amount of buffers, nutrients and proteins in EMEM seem to reduce the activity of PAAG but is still effective at blocking binding of bacteria to the epithelial cells.

Example 16

PAAG does not Develop Resistance

Protocol:

MRSA strain MW-2 was repeatedly passaged in PAAG (30% functionalized, 35 kDa or 4% functionalized, 59 kDa) to examine the ability of the strain to acquire resistance to PAAG. MRSA were grown in Todd Hewitt broth overnight and resuspended to approximately $10^5$ CFU/ml. The MRSA was then treated with buffer alone or 100 µg/ml PAAG for 1-hour. The surviving bacteria were grown up in Todd Hewitt broth overnight. This process was repeated 10 times. Three single colonies were isolated from each treated culture, grown up and subjected to a final 20-hour treatment with either buffer or PAAG.

Results:

MRSA strain MW-2 was tested for development of resistance after 10 daily 1-hour treatments with 100 µg/ml PAAG (either 4% or 30% functionalized) of surviving bacteria. Three colonies were isolated and a final 20-hour treatment with PAAG or buffer was completed, showing MRSA strain MW-2 maintained susceptibility to PAAG after this level of repetitive exposure (FIG. 33). No alteration of susceptibility in strain MW-2 was observed.

The invention claimed is:

1. A method of treating a dermal wound in a subject, the method comprising topically administering to the wound an aqueous pharmaceutical gel comprising
   hydroxypropyl methylcellulose in an amount of about 0.5% to about 5% by weight per volume of the pharmaceutical gel;

a compound of formula (I)

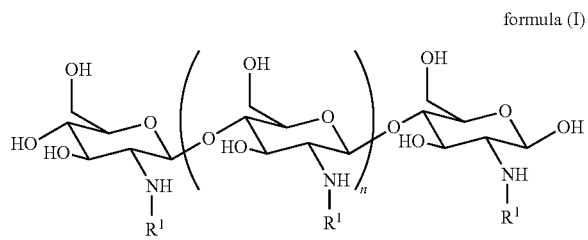

formula (I)

wherein:
n is an integer between 20 and 6000; and
each $R^1$ is independently selected for each occurrence from hydrogen, acetyl,

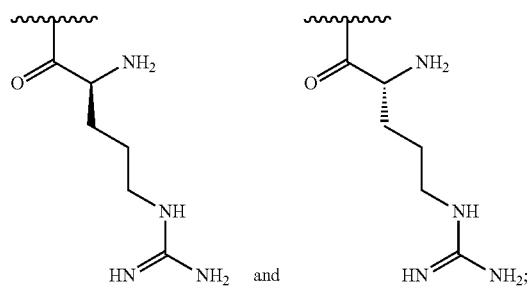 [SMILES: *C(=O)[C@@H](N)CCCNC(=N)N ; *C(=O)[C@H](N)CCCNC(=N)N]

wherein at least 25% of $R^1$ substituents are H, at least 1% of $R^1$ substituents are acetyl, and at least 2% of $R^1$ substituents are

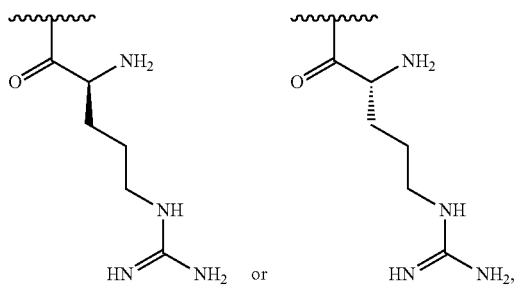 [SMILES: *C(=O)[C@@H](N)CCCNC(=N)N ; *C(=O)[C@H](N)CCCNC(=N)N]

a preservative; and
sterile water, wherein the compound of formula (I) is present in an amount of 0.5% by weight in the pharmaceutical gel;

wherein 21 days after administration of the aqueous pharmaceutical gel, the dermal wound has a thicker epidermis compared to an untreated wound, thereby treating the wound in the subject.

2. The method of claim 1, wherein the subject is a human.

3. The method of claim 1, wherein the subject is in the family Elephantidae, Rhinocerotidae, or tapirs.

4. The method of claim 1, wherein the subject is a domesticated animal or pet.

5. The method of claim 1, wherein the pharmaceutical gel is administered in a volume sufficient to moisten the wound.

6. The method of claim 1, wherein the wound is caused by a chronic disease.

7. The method of claim 1, wherein the wound is a chronic and non-healing dermal or subdermal wound.

8. The method of claim 1, wherein the wound is infected with bacteria.

9. The method of claim 1, wherein the wound is a chronic wound.

10. The method of claim 1, wherein the wound is an acute wound.

11. The method of claim 1 wherein the pharmaceutical gel is administered 1, 2, or 3 times a day.

12. The method of claim 1, wherein the method reduces the healing time or increases the healing rate of the wound.

13. The method of claim 12, wherein the healing time of the wound is reduced by at least about 10% compared to the healing time of the wound that has not been contacted with the pharmaceutical gel.

14. The method of claim 1, wherein the method improves the healing of the wound, wherein healing of the wound results in inflammation, and wherein the inflammation resulting from the healing of the wound is reduced.

15. The method of claim 1, wherein the method decreases the magnitude or extent of scarring.

16. The method of claim 1, wherein the wound, upon treatment, has a reduced bacterial load.

17. The method of claim 1, wherein the method comprises rinsing the wound to provide a covering of the wound with a thin layer of a compound of formula (I), wherein the thin layer of a compound of formula (I) reduces the ability of bacteria to bind to the wound relative to a control.

18. The method of claim 1, wherein the wound is a puncture, abrasion, laceration, incision, scrape, or excision.

* * * * *